(12) United States Patent
Prat et al.

(10) Patent No.: US 8,293,468 B2
(45) Date of Patent: Oct. 23, 2012

(54) MCAM MODULATION AND USES THEREOF

(75) Inventors: Alexandre Prat, Outremont (CA); Romain Cayrol, Montreal (CA); Nathalie Arbour, Outremont (CA); Catherine Larochelle, Montreal (CA)

(73) Assignee: Centre Hospitalier de l'Université de Montréal, Montreal (CA)

( * ) Notice: Subject to any disclaimer, the term of this patent is extended or adjusted under 35 U.S.C. 154(b) by 120 days.

(21) Appl. No.: 12/797,055

(22) Filed: Jun. 9, 2010

(65) Prior Publication Data
US 2011/0014183 A1 Jan. 20, 2011

Related U.S. Application Data

(60) Provisional application No. 61/185,707, filed on Jun. 10, 2009.

(30) Foreign Application Priority Data

Aug. 25, 2009 (AU) ................................ 2009212789
Aug. 25, 2009 (CA) .................................... 2,676,962

(51) Int. Cl.
*C12Q 1/68* (2006.01)
(52) U.S. Cl. ............................ 435/6; 435/325; 435/375
(58) Field of Classification Search ........................ None
See application file for complete search history.

(56) References Cited

U.S. PATENT DOCUMENTS

| 6,025,155 | A | 2/2000 | Hadlaczky et al. |
| 6,077,677 | A | 6/2000 | Hodgson et al. |
| 6,204,023 | B1 | 3/2001 | Robinson et al. |
| 2002/0160970 | A1 | 10/2002 | Hadlaczky et al. |
| 2003/0083293 | A1 | 5/2003 | Hadlaczky et al. |
| 2004/0156826 | A1* | 8/2004 | Dangond et al. ............. 424/93.2 |

FOREIGN PATENT DOCUMENTS

WO WO2004/007550 1/2004

OTHER PUBLICATIONS

Bar Eli, M. (2001) Gene Regulation in Melanoma Progression by the AP-2 Transcription Factor. Pigment Cell Research, V.14:78-85.*
Lee, et al. (2008) "Lymphocyte Transmigration in the Brain: A New Way of Thinking" Nature Immunology, v.9(2):117-8.*
C. F. Lacy et al., Drug information handbook 8th Edition, 2001, pp. 549-551.
Karin N. et al., "Reversal of experimental autoimmune encephalomyelitis by a soluble peptide variant of a myelin basic protein epitope: T cell receptor antagonism and reduction of interferon y and tumor necrosis factor a production", (1994) J Exp Med. 180(6): 2227-37.
Binz and Plückthun, "Engineered proteins as specific binding reagents", 2005, Curr. Opin. Biotech. 16: 1-11.
Prat et al., "Kirin B1 receptor expression and function on human brain endothelial cells", J Neuropathol Exp Neurol. 2000 59(10):896-906.
Biernacki et al., "Regulation of Th1 and Th2 lymphocyte migration by human adult brain endothelial cells", J Neuropathol Exp Neurol. 2001 60(12): 1127-36.
Prat et al., "Migration of multiple sclerosis lymphocytes through brain endothelium", Arch Neurol. 2002 59(3): 391-7.
Bardin et al., "CD146 and its soluble form regulate monocyte transendothelial migration", Arterioscler Thromb Vasc Biol. May 2009;29(5):746-53. Epub Feb. 19, 2009.
Mangahas et al., "Endothelin-1 upregulates MCAM in melanocytes", J. Invest. Dermatol. (2004) 123: 1135-1139.
Mills et al., "Fully human antibodies to MCAM/MUC18 inhibit tumor growth and metastasis of human melanoma", Cancer Research 62, 5106-5114, Sep. 1, 2002.
Kebir et al., "Human Th17 lymphocytes promote blood-brain barrier disruption and central nervous system inflammation", Nat Med. 2007 13(10):1173-5. Epub Sep. 9, 2007.
Cayrol et al., "Activated leukocyte cell adhesion molecule promotes leukocyte trafficking into the central nervous system", Nat Immunol. 2008 9(2):137-45. Epub Dec. 23, 2007.
Ifergan et al., "The blood-brain barrier induces differentiation of migrating monocytes into Th17-polarizing dendritic cells", Brain. 2008 131(Pt 3): 785-99. Epub Dec. 20, 2007.

\* cited by examiner

*Primary Examiner* — Jennifer Pitrak McDonald
(74) *Attorney, Agent, or Firm* — Goudreau Gage Dubuc; S. Serge Shahinian; Alain Dumont

(57) ABSTRACT

Methods, uses, agents and compositions useful for the diagnosis, prevention and/or treatment of inflammatory conditions, such as neuroinflammatory conditions such as multiple sclerosis, and for the identification and selection of inflammatory cytokine-secreting T cell or a precursor thereof, based on the expression and/or modulation of melanoma cell adhesion molecule (MCAM) are disclosed.

9 Claims, 42 Drawing Sheets

Table 1: Ex vivo MCAM+ human peripheral blood lymphocyte associated markers

| | Ex vivo expression level |
|---|---|
| CD2 | +++ |
| CD3 | +++ |
| CD4 | ++ |
| CD8 | --- |
| CD45RO | +++ |
| CD45RA | --- |
| g-d TCR | --- |
| CD14 | --- |
| CD19 | -- |
| CD25 | --- |
| CD27 | --- |
| CD28 | ++ |
| CD56 | --- |
| CD62L | -- |
| CD69 | --- |
| CD161 | + |
| CD95 | ++ |
| CD107a | --- |
| CCR6 | ++ |
| CCR7 | -- |
| NKG2D | --- |
| GranA | --- |
| GranB | --- |
| IL-4 | --- |
| IL-10 | --- |
| IL-17 | --- |
| IL-22 | --- |
| IFN-gamma | --- |

| | |
|---|---|
| +++ | expressed by at least 90% of MCAM + cells |
| ++ | expressed by at least 75% of MCAM + cells |
| + | expressed by at least 50% of MCAM + cells |
| --- | expressed by less than 10% of MCAM + cells |
| -- | expressed by less than 25% of MCAM + cells |
| - | expressed by less than 50% of MCAM + cells |

Assesed on n > 4 healthy donors

Fig. 4G

Ex vivo
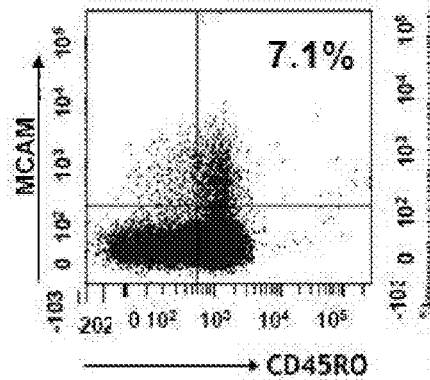 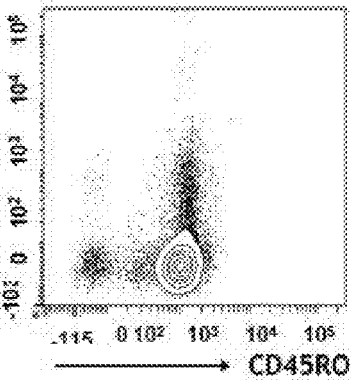
FIG. 6A  FIG. 6B
In vitro
activated
(anti-CD3, IL-2, APC
for 3 days)
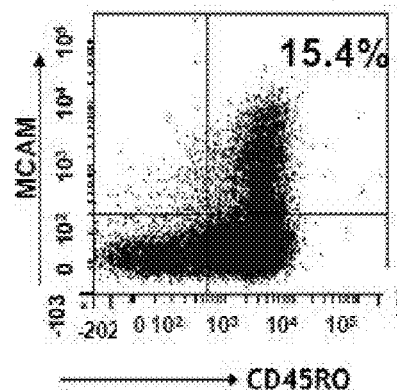 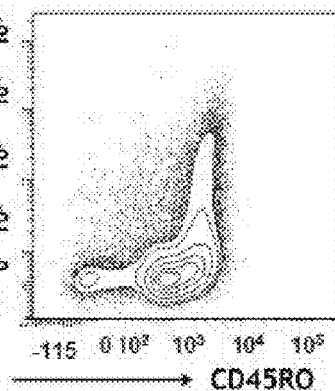
FIG. 6C  FIG. 6D

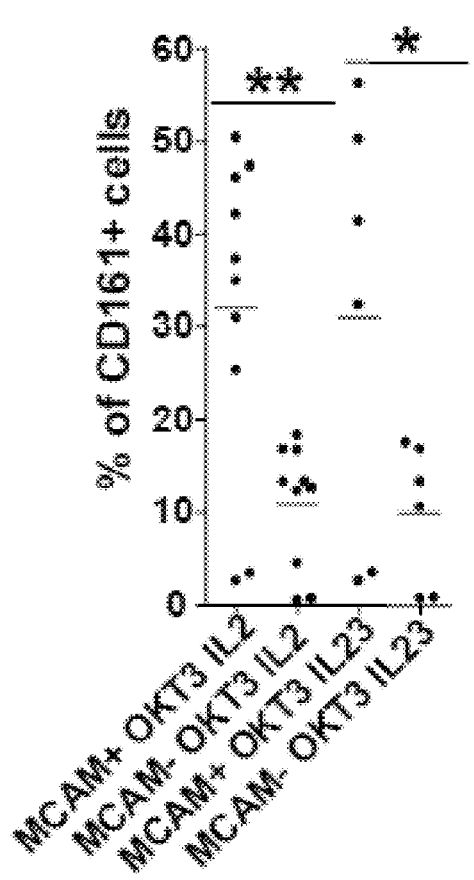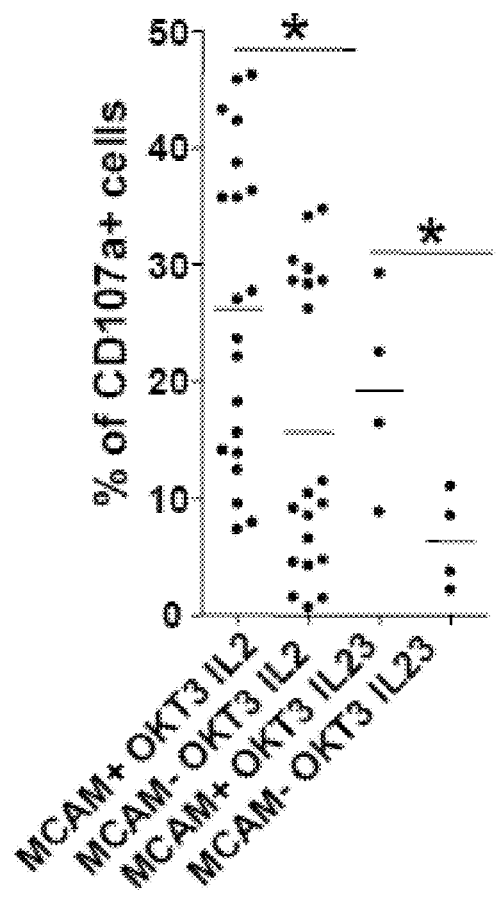
FIG. 7A  FIG. 7B

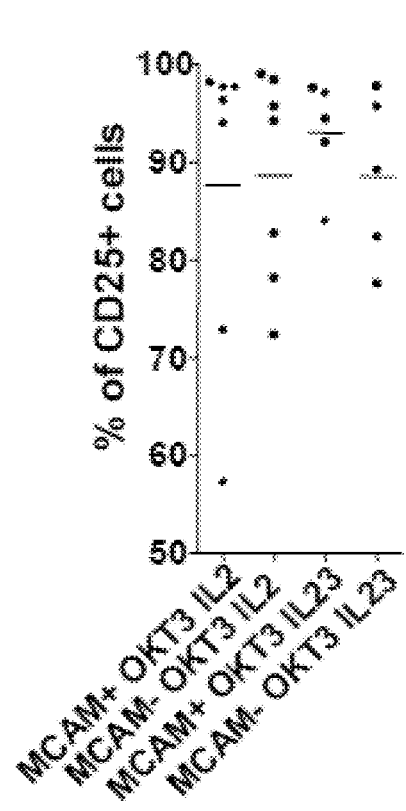 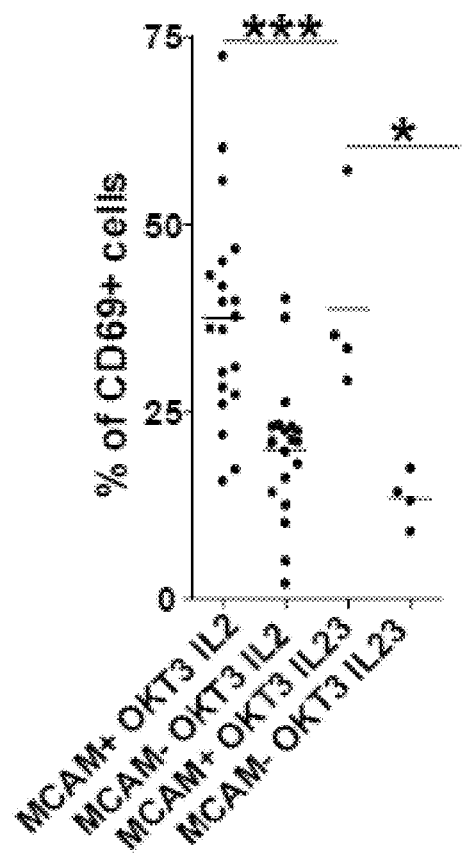
FIG. 7C  FIG. 7D

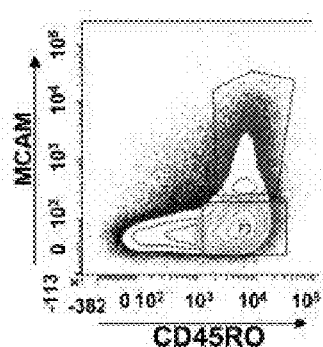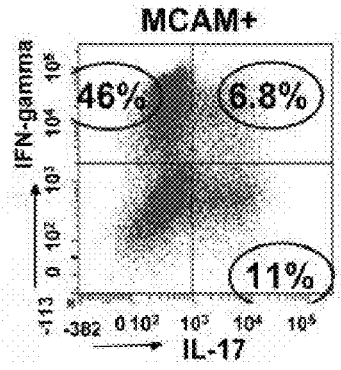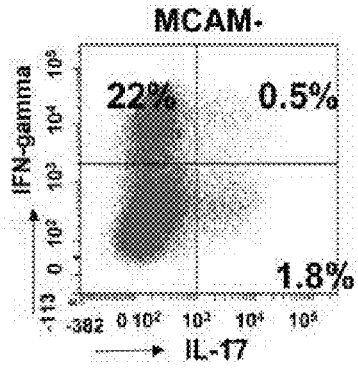
FIG. 8A    FIG. 8B    FIG. 8C
*In vitro* activated
Gated on CD4+ MCAM+
And CD4+ MCAM- cells
(anti-CD3, IL-2, APC)
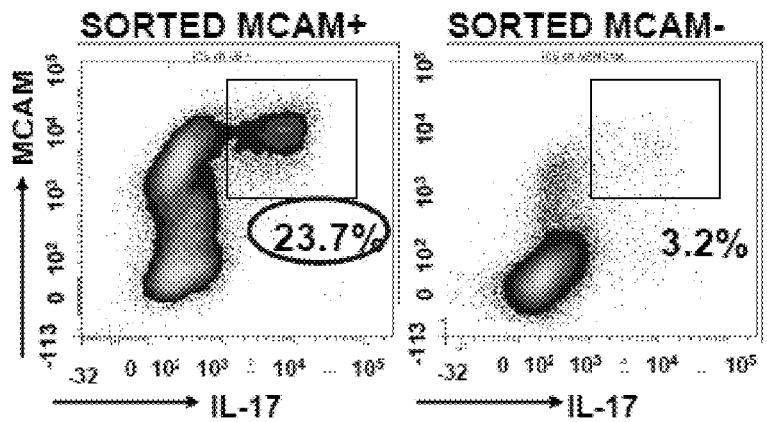
FIG. 8D    FIG. 8E
*In vitro* activated
CD4 CD45RO MCAM+
vs CD4+ CD45RO+ MCAM-
(anti-CD3, IL-2, APC)

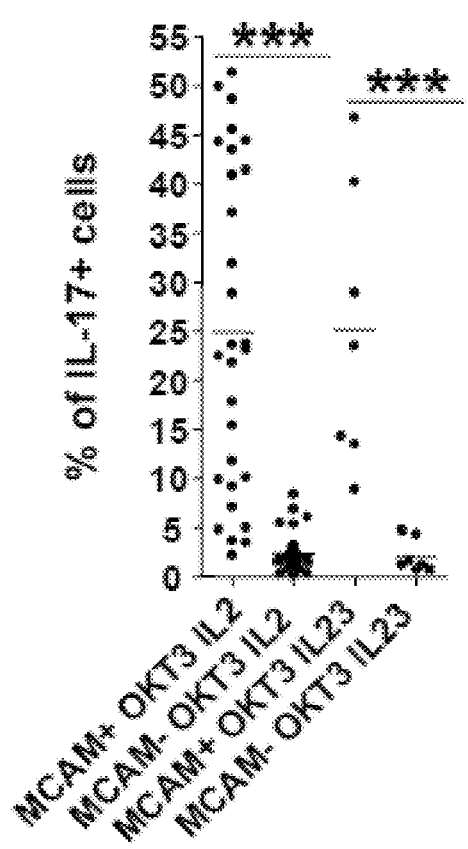 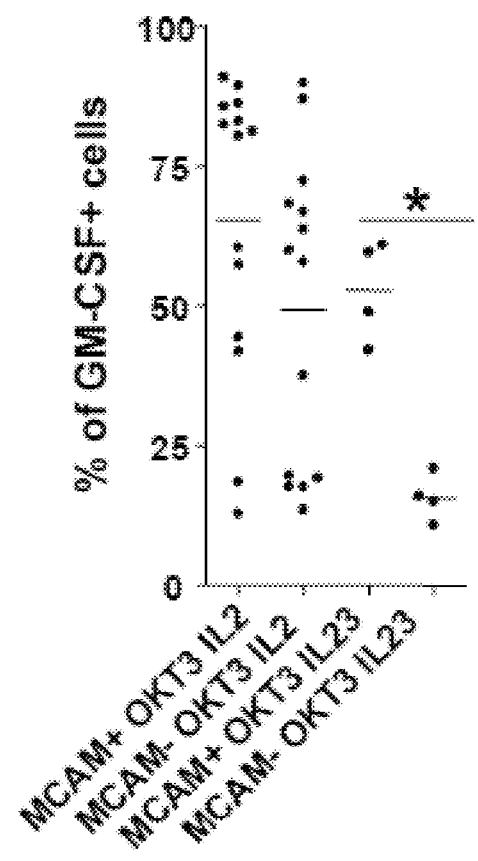
FIG. 9A    FIG. 9B

|          | anti-CD3 and IL-2 | | | anti-CD3 and IL-23 | | |
|----------|-------|-------|-----|-------|-------|-----|
|          | MCAM+ | MCAM- |     | MCAM+ | MCAM- |     |
| CD69     | 37.5  | 19.9  | *** | 38.7  | 13.4  | *   |
| CD161    | 32.5  | 10.9  | **  | 31.5  | 9.9   | *   |
| CD107a   | 26.2  | 15.6  | *   | 19.2  | 6.3   | *   |
| CD25     | 89.9  | 85.5  |     | 88    | 91.3  |     |
| HLA-DR   | 20.4  | 14.5  |     | 25.5  | 14.5  |     |
| IL-4     | 42.3  | 45.1  |     | 50.2  | 47.3  |     |
| IL-17    | 24.9  | 2.4   | *** | 29.14 | 2     | *** |
| TNF      | 54.4  | 38.1  | *   | 65.5  | 16.8  | *   |
| GM-CSF   | 65.2  | 49.3  |     | 52.8  | 15.6  | *   |
| IFN-gamma| 50.4  | 26.8  | *** | 43.5  | 8.2   | **  |

Isolated CD4+ CD45RO+ MCAM+ and MCAM- were activated in vitro with autologous CD14+ cells, anti-CD3, with either IL-2 (n > 7) or IL-23 + anti-IFN-gamma + anti-IL-4 (n > 4). In vitro culture was done for 5 days.

* $p < 0.05$
** $p < 0.01$
*** $p < 0.001$
Statistical significance was calculated using a non-parametric student t-test.

FIG. 10

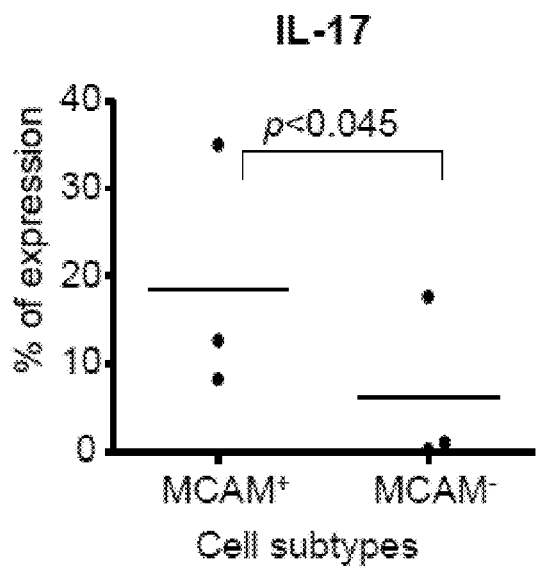
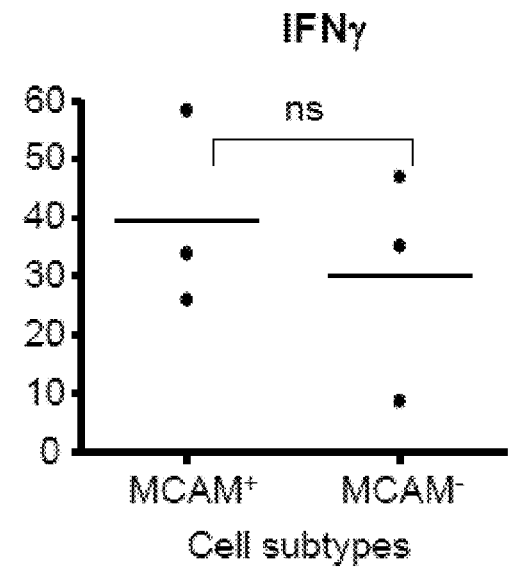
FIG. 14A
FIG. 14B
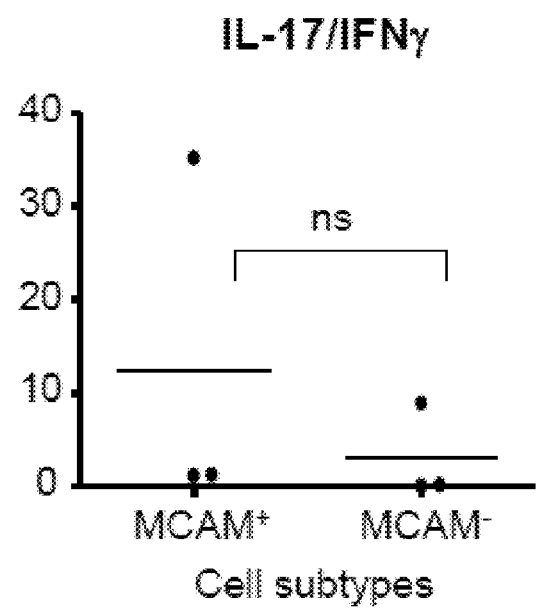
FIG. 14C

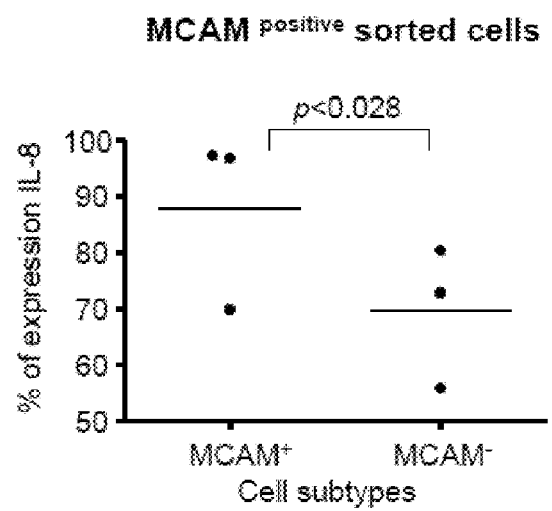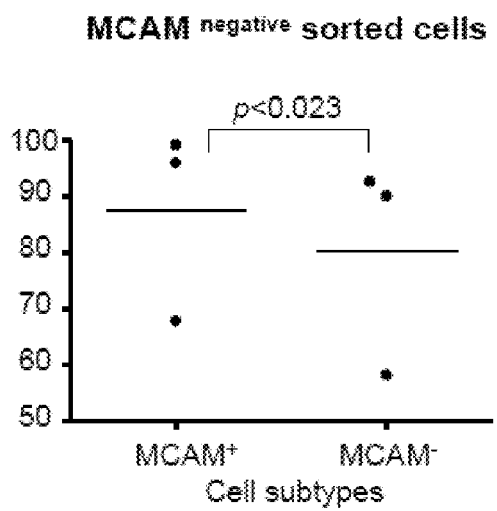
FIG. 15A
FIG. 15B

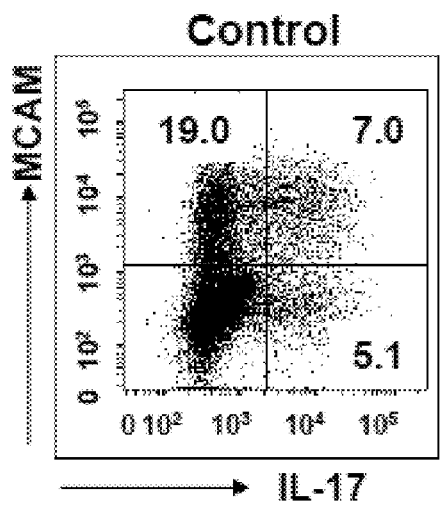
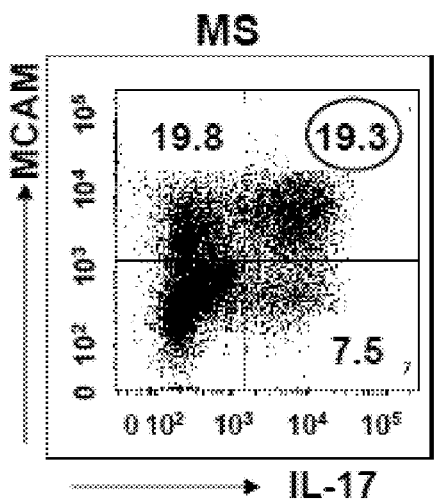
FIG. 17A  FIG. 17B
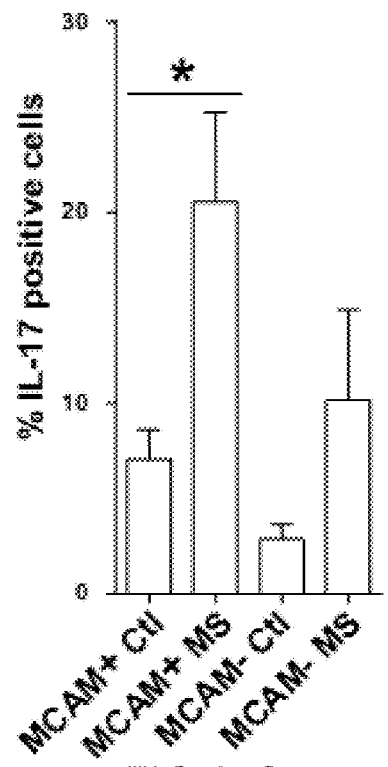
FIG. 17C

```
   1 acttggctct cgccctccgg ccgggaagca tggggcttcc caggctggtc tgcgccttct
  61 tgctcgccgc ctgctgctgc tgtcctcgcg tcgcgggtgt gcccggagag gctgagcagc
 121 ctgcgcctga gctggtggag gtgaagtggg cagcacagc ccttctgaag tgcggcctct
 181 cccagtccca aggcaacctc agccatgtcg actggttttc tgtccacaag gagaagcgga
 241 cgctcatctt ccgtgtgcgc cagggccagg ccagagcga acctggggag tacgagcagc
 301 ggctcagcct ccaggacaga ggggctactc tggccctgac tcaagtcacc ccccaagacg
 361 agcgcatctt cttgtgccag ggcaagcgcc ctcggtccca ggagtaccgc atccagctcc
 421 gcgtctacaa agctccggag gagccaaaca tccaggtcaa ccccctgggc atccctgtga
 481 acagtaagga gcctgaggag gtcgctacct gtgtagggag gaacgggtac cccattcctc
 541 aagtcatctg gtacaagaat ggccggcctc tgaaggagga gaagaaccgg gtccacattc
 601 agtcgtccca gactgtggag tcgagtggtt tgtacacctt gcagagtatt ctgaaggcac
 661 agctggttaa agaagacaaa gatgcccagt tttactgtga gctcaactac cggctgccca
 721 gtgggaacca catgaaggag tccagggaag tcaccgtccc tgttttctac ccgacagaaa
 781 aagtgtggct ggaagtggag cccgtgggaa tgctgaagga aggggaccgc gtggaaatca
 841 ggtgtttggc tgatggcaac cctccaccac acttcagcat cagcaagcag aaccccagca
 901 ccagggaggc agaggaagag acaaccaacg caacgggggt cctggtgctg gagcctgccc
 961 ggaaggaaca cagtgggcgc tatgaatgtc agggcctgga cttggacacc atgatatcgc
1021 tgctgagtga accacaggaa ctactggtga actatgtgtc tgacgtccga gtgagtcccg
1081 cagcccctga gagacaggaa ggcagcagcc tcacctgac ctgtgaggca gagagtagcc
1141 aggacctcga gttccagtgg ctgagagaag agacaggcca ggtgctgaa aggggggcctg
1201 tgcttcagtt gcatgacctg aaacgggagg caggaggcgg ctatcgctgc gtggcgtctg
1261 tgcccagcat acccggcctg aaccgcacac agctggtcaa cgtggccatt tttggccccc
1321 cttggatggc attcaaggag aggaaggtgt gggtgaaaga gaatatggtg ttgaatctgt
1381 cttgtgaagc gtcagggcac ccccggccca ccatctcctg gaacgtcaac ggcacggcaa
1441 gtgaacaaga ccaagatcca cagcgagtcc tgagcaccct gaatgtcctc gtgaccccgg
1501 agctgttgga gacaggtgtt gaatgcacgg cctccaacga cctgggcaaa acaccagcca
1561 tcctcttcct ggagctggtc aatttaacca ccctcacacc agactccaac acaaccactg
1621 gcctcagcac ttccactgcc agtcctcata ccagagccaa cagcacctcc acagagagaa
1681 agctgccgga gccggagagc cggggcgtgg tcatcgtggc tgtgattgtg tgcatcctgg
1741 tcctggcggt gctgggcgct gtcctctatt tcctctataa gaagggcaag ctgccgtgca
1801 ggcgctcagg gaagcaggag atcacgctac cccgtctcg taagagcgaa cttgtagttg
1861 aagttaagtc agataagctc ccagaagaga tgggcctcct gcagggcagc agcggtgaca
1921 agagggctcc gggagaccag ggagagaaat acatcgatct gaggcattag ccccgaatca
1981 cttcagctcc cttccctgcc tggaccattc ccagctccct gctcactctt ctctcagcca
2041 aagcctccaa agggactaga gagaagcctc ctgctcccct cgcctgcaca ccccctttca
2101 gagggccact gggttaggac ctgaggacct cacttggccc tgcaaggccc gcttttcagg
2161 gaccagtcca ccaccatctc ctccacgttg agtgaagctc atcccaagca aggagcccca
2221 gtctcccgag cgggtaggag agtttcttgc agaacgtgtt ttttctttac acacattatg
2281 gctgtaaata cctggctcct gccagcagct gagctgggta gcctctctga gctggtttcc
2341 tgccccaaag gctggcttcc accatccagg tgcaccactg aagtgaggac acaccggagc
2401 caggcgcctg ctcatgttga agtgcgctgt tcacacccgc tccggagagc acccagcag
2461 catccagaag cagctgcagt gttgctgcca ccacctcct gtctgcctct tcaaagtctc
2521 ctgtgacatt ttttctttgg tcagaagcca ggaactggtg tcattcctta aagatacgt
2581 gccggggcca ggtgtggtgg ctcacgcctg taatcccagc actttgggag gccgaggcgg
2641 gcggatcaca aagtcaggac gagaccatcc tggctaacac ggtgaaaccc tgtctctact
2701 aaaaatacaa aaaaaaatta gctaggcgta gtggttggca cctatagtcc cagctactcg
2761 gaaggctgaa gcaggagaat ggtatgaatc caggaggtgg agcttgcagt gagccgagac
2821 cgtgccactg cactccagcc tgggcaacac agcgagactc cgtctcgagg aaaaaaaaag
2881 aaaagatacg tgcctgcggt gaggaagctg ggcgctgttt tcgagttcag gtgaattagc
2941 ctcaatcccc cgtgttcact tggctcccat agccctcttg atggatcacg taaaactgaa
3001 aggcagcggg gagcagacaa agatgaggtc tacactgtcc ttcatgcgga ttaaagctat
```

FIG. 19A

```
3061 ggttatatta gcaccaaact tctacaaacc aagctcaggg ccccaaccct agaagggccc
3121 aaatgagaga atggtactta gggatggaaa acgggcctgg ctagagcttc gggtgtgtgt
3181 gtctgtctgt gtgtatgcat acatatgtgt gtatatatgg ttttgtcagg tgtgtaaatt
3241 tgcaaattgt ttcctttata tatgtatgta tatatatata tgaaaatata tatatatatg
3301 aaaaataaag cttaattgtc ccagaaatca ta
```

FIG. 19B

```
  1 mglprlvcaf llaaccccpr vagvpgeaeq papelvevev gstallkcgl sqsqgnlshv
 61 dwfsvhkekr tlifrvrqgq gqsepgeyeq rlslqdrgat laltqvtpqd eriflcqgkr
121 prsqeyriql rvykapeepn iqvnplgipv nskepeevat cvcrngypip qviwykngrp
181 lkeeknrvhi qssqtvessg lytlqsilka qlvkedkdaq fycelnyrlp sgnhmkesre
241 vtvpvfypte kvwlevepvg mlkegdrvei rcladgnppp hfsiskqnps treaeeettn
301 dngvlvlepa rkehsgryec qgldldtmis llsepqellv nyvsdvrvsp aaperqegss
361 ltltceaess qdlefqwlre etgqvlergp vlqlhdlkre agggyrcvas vpsipglnrt
421 qlvnvaifgp pwmafkerkv wvkenmvlnl sceasghprp tiswnvngta seqdqdpqrv
481 lstlnvlvtp elletgvect asndlgknts ilflelvnlt tltpdsnttt glststasph
541 transtster klpepesrgv vivavivcil vlavlgavly flykkgklpc rrsgkqeitl
601 ppsrkselvv evksdklpee mgllqgssgd krapgdqgek yidlrh
```

FIG. 19C

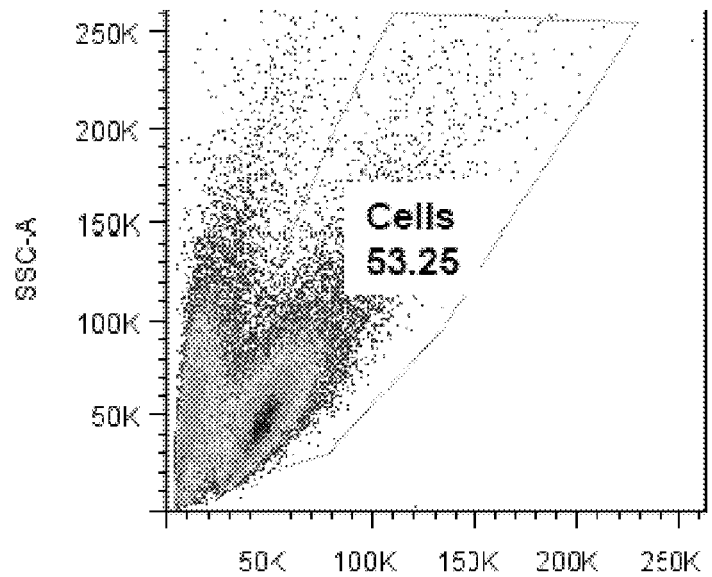
FIG. 24C
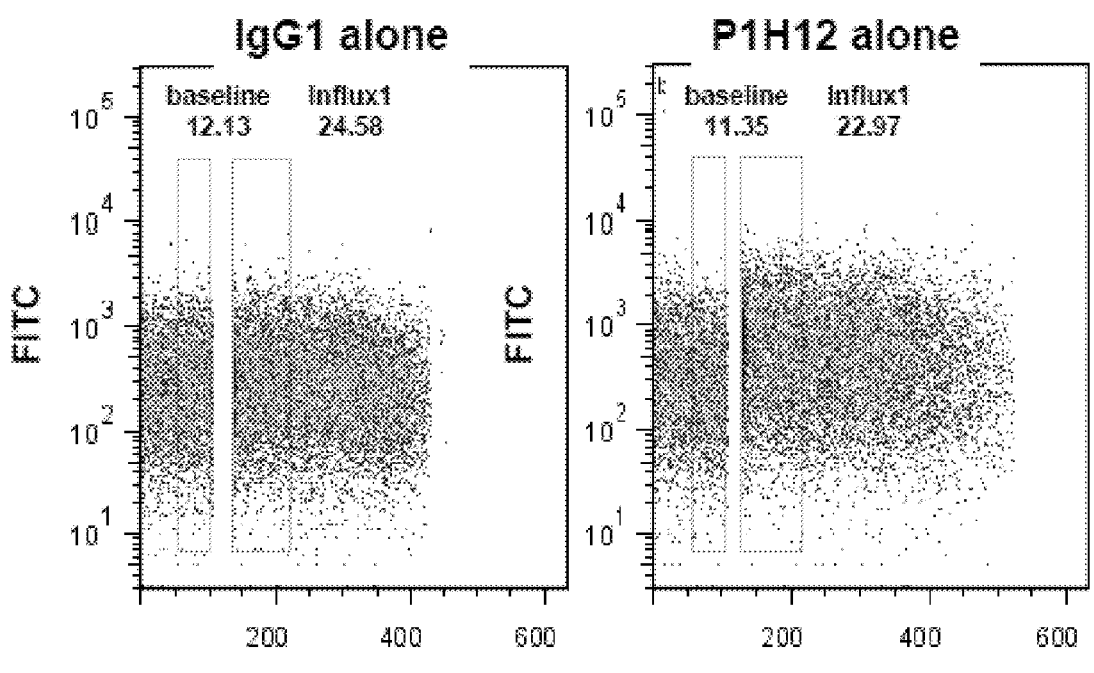
FIG. 24D     FIG. 24E

SEQUENCE LISTING

<160> NUMBER OF SEQ ID NOS: 3

<210> SEQ ID NO 1
<211> LENGTH: 3332
<212> TYPE: DNA
<213> ORGANISM: Homo sapiens
<220> FEATURE:
<221> NAME/KEY: CDS
<222> LOCATION: (30)..(1970)

<400> SEQUENCE: 1

```
acttggctct cgccctccgg ccgggaagc atg ggg ctt ccc agg ctg gtc tgc      53
                                Met Gly Leu Pro Arg Leu Val Cys
                                1               5
```

```
gcc ttc ttg ctc gcc gcc tgc tgc tgt cct cgc gtc gcg ggt gtg      101
Ala Phe Leu Leu Ala Ala Cys Cys Cys Pro Arg Val Ala Gly Val
        10              15              20 ccc gga gag gct gag cag cct gcg cct gag ctg gtg gag gtg gaa gtg  149
Pro Gly Glu Ala Glu Gln Pro Ala Pro Glu Leu Val Glu Val Glu Val
25              30              35              40 ggc agc aca gcc ctt ctg aag tgc ggc ctc tcc cag tcc caa ggc aac  197
Gly Ser Thr Ala Leu Leu Lys Cys Gly Leu Ser Gln Ser Gln Gly Asn
                45              50              55 ctc agc cat gtc gac tgg ttt tct gtc cac aag gag aag cgg acg ctc  245
Leu Ser His Val Asp Trp Phe Ser Val His Lys Glu Lys Arg Thr Leu
        60              65              70 atc ttc cgt gtg cgc cag ggc cag ggc cag agc gaa cct ggg gag tac  293
Ile Phe Arg Val Arg Gln Gly Gln Gly Gln Ser Glu Pro Gly Glu Tyr
    75              80              85 gag cag cgg ctc agc ctc cag gac aga ggg gct act ctg gcc ctg act  341
Glu Gln Arg Leu Ser Leu Gln Asp Arg Gly Ala Thr Leu Ala Leu Thr
        90              95              100 caa gtc acc ccc caa gac gag cgc atc ttc ttg tgc cag ggc aag cgc  389
Gln Val Thr Pro Gln Asp Glu Arg Ile Phe Leu Cys Gln Gly Lys Arg
105             110             115             120 cct cgg tcc cag gag tac cgc atc cag ctc cgc gtc tac aaa gct ccg  437
Pro Arg Ser Gln Glu Tyr Arg Ile Gln Leu Arg Val Tyr Lys Ala Pro
            125             130             135 gag gag cca aac atc cag gtc aac ccc ctg ggc atc cct gtg aac agt  485
Glu Glu Pro Asn Ile Gln Val Asn Pro Leu Gly Ile Pro Val Asn Ser
        140             145             150 aag gag cct gag gag gtc gct acc tgt gta ggg agg aac ggg tac ccc  533
Lys Glu Pro Glu Glu Val Ala Thr Cys Val Gly Arg Asn Gly Tyr Pro
    155             160             165 att cct caa gtc atc tgg tac aag aat ggc cgg cct ctg aag gag gag  581
Ile Pro Gln Val Ile Trp Tyr Lys Asn Gly Arg Pro Leu Lys Glu Glu
170             175             180 aag aac cgg gtc cac att cag tcg tcc cag act gtg gag tcg agt ggt  629
Lys Asn Arg Val His Ile Gln Ser Ser Gln Thr Val Glu Ser Ser Gly
185             190             195             200 ttg tac acc ttg cag agt att ctg aag gca cag ctg gtt aaa gaa gac  677
Leu Tyr Thr Leu Gln Ser Ile Leu Lys Ala Gln Leu Val Lys Glu Asp
            205             210             215 aaa gat gcc cag ttt tac tgt gag ctc aac tac cgg ctg ccc agt ggg  725
Lys Asp Ala Gln Phe Tyr Cys Glu Leu Asn Tyr Arg Leu Pro Ser Gly
        220             225             230 aac cac atg aag gag tcc agg gaa gtc acc gtc cct gtt ttc tac ccg  773
Asn His Met Lys Glu Ser Arg Glu Val Thr Val Pro Val Phe Tyr Pro
    235             240             245 aca gaa aaa gtg tgg ctg gaa gtg gag ccc gtg gga atg ctg aag gaa  821
Thr Glu Lys Val Trp Leu Glu Val Glu Pro Val Gly Met Leu Lys Glu
250             255             260 ggg gac cgc gtg gaa atc agg tgt ttg gct gat ggc aac cct cca cca  869
Gly Asp Arg Val Glu Ile Arg Cys Leu Ala Asp Gly Asn Pro Pro Pro
265             270             275             280 cac ttc agc atc agc aag cag aac ccc agc acc agg gag gca gag gaa  917
His Phe Ser Ile Ser Lys Gln Asn Pro Ser Thr Arg Glu Ala Glu Glu
            285             290             295 gag aca acc aac gac aac ggg gtc ctg gtg ctg gag cct gcc cgg aag  965
Glu Thr Thr Asn Asp Asn Gly Val Leu Val Leu Glu Pro Ala Arg Lys
        300             305             310 gaa cac agt ggg cgc tat gaa tgt cag ggc ctg gac ttg gac acc atg  1013
Glu His Ser Gly Arg Tyr Glu Cys Gln Gly Leu Asp Leu Asp Thr Met
    315             320             325
```

```
ata tcg ctg ctg agt gaa cca cag gaa cta ctg gtg aac tat gtg tct      1061
Ile Ser Leu Leu Ser Glu Pro Gln Glu Leu Leu Val Asn Tyr Val Ser
    330                 335                 340 gac gtc cga gtg agt ccc gca gcc cct gag aga cag gaa ggc agc agc      1109
Asp Val Arg Val Ser Pro Ala Ala Pro Glu Arg Gln Glu Gly Ser Ser
345                 350                 355                 360 ctc acc ctg acc tgt gag gca gag agt agc cag gac ctc gag ttc cag      1157
Leu Thr Leu Thr Cys Glu Ala Glu Ser Ser Gln Asp Leu Glu Phe Gln
                365                 370                 375 tgg ctg aga gaa gag aca ggc cag gtg ctg gaa agg ggg cct gtg ctt      1205
Trp Leu Arg Glu Glu Thr Gly Gln Val Leu Glu Arg Gly Pro Val Leu
            380                 385                 390 cag ttg cat gac ctg aaa cgg gag gca gga ggc ggc tat cgc tgc gtg      1253
Gln Leu His Asp Leu Lys Arg Glu Ala Gly Gly Gly Tyr Arg Cys Val
        395                 400                 405 gcg tct gtg ccc agc ata ccc ggc ctg aac cgc aca cag ctg gtc aac      1301
Ala Ser Val Pro Ser Ile Pro Gly Leu Asn Arg Thr Gln Leu Val Asn
    410                 415                 420 gtg gcc att ttt ggc ccc cct tgg atg gca ttc aag gag agg aag gtg      1349
Val Ala Ile Phe Gly Pro Pro Trp Met Ala Phe Lys Glu Arg Lys Val
425                 430                 435                 440 tgg gtg aaa gag aat atg gtg ttg aat ctg tct tgt gaa gcg tca ggg      1397
Trp Val Lys Glu Asn Met Val Leu Asn Leu Ser Cys Glu Ala Ser Gly
                445                 450                 455 cac ccc cgg ccc acc atc tcc tgg aac gtc aac ggc acg gca agt gaa      1445
His Pro Arg Pro Thr Ile Ser Trp Asn Val Asn Gly Thr Ala Ser Glu
            460                 465                 470 caa gac caa gat cca cag cga gtc ctg agc acc ctg aat gtc ctc gtg      1493
Gln Asp Gln Asp Pro Gln Arg Val Leu Ser Thr Leu Asn Val Leu Val
        475                 480                 485 acc ccg gag ctg ttg gag aca ggt gtt gaa tgc acg gcc tcc aac gac      1541
Thr Pro Glu Leu Leu Glu Thr Gly Val Glu Cys Thr Ala Ser Asn Asp
    490                 495                 500 ctg ggc aaa aac acc agc atc ctc ttc ctg gag ctg gtc aat tta acc      1589
Leu Gly Lys Asn Thr Ser Ile Leu Phe Leu Glu Leu Val Asn Leu Thr
505                 510                 515                 520 acc ctc aca cca gac tcc aac aca acc act ggc ctc agc act tcc act      1637
Thr Leu Thr Pro Asp Ser Asn Thr Thr Thr Gly Leu Ser Thr Ser Thr
                525                 530                 535 gcc agt cct cat acc aga gcc aac agc acc tcc aca gag aga aag ctg      1685
Ala Ser Pro His Thr Arg Ala Asn Ser Thr Ser Thr Glu Arg Lys Leu
            540                 545                 550 ccg gag ccg gag agc cgg ggc gtg gtc atc gtg gct gtg att gtg tgc      1733
Pro Glu Pro Glu Ser Arg Gly Val Val Ile Val Ala Val Ile Val Cys
        555                 560                 565 atc ctg gtc ctg gcg gtg ctg ggc gct gtc ctc tat ttc ctc tat aag      1781
Ile Leu Val Leu Ala Val Leu Gly Ala Val Leu Tyr Phe Leu Tyr Lys
    570                 575                 580 aag ggc aag ctg ccg tgc agg cgc tca ggg aag cag gag atc acg cta      1829
Lys Gly Lys Leu Pro Cys Arg Arg Ser Gly Lys Gln Glu Ile Thr Leu
585                 590                 595                 600 ccc ccg tct cgt aag agc gaa ctt gta gtt gaa gtt aag tca gat aag      1877
Pro Pro Ser Arg Lys Ser Glu Leu Val Val Glu Val Lys Ser Asp Lys
                605                 610                 615 ctc cca gaa gag atg ggc ctc ctg cag ggc agc agc ggt gac aag agg      1925
Leu Pro Glu Glu Met Gly Leu Leu Gln Gly Ser Ser Gly Asp Lys Arg
            620                 625                 630 gct ccg gga gac cag gga gag aaa tac atc gat ctg agg cat tag          1970
Ala Pro Gly Asp Gln Gly Glu Lys Tyr Ile Asp Leu Arg His
        635                 640                 645
```

```
cccccgaatca cttcagctcc cttccctgcc tggaccattc ccagctccct gctcactctt    2030
ctctcagcca aagcctccaa agggactaga gagaagcctc ctgctcccct cgcctgcaca    2090
ccccctttca gagggccact gggttaggac ctgaggacct cacttggccc tgcaaggccc    2150
gcttttcagg gaccagtcca ccaccatctc ctccacgttg agtgaagctc atcccaagca    2210
aggagcccca gtctcccgag cgggtaggag agtttcttgc agaacgtgtt ttttcttttac    2270 acacattatg gctgtaaata cctggctcct gccagcagct gagctgggta gcctctctga    2330
gctggtttcc tgcccaaag gctggcttcc accatccagg tgcaccactg aagtgaggac    2390
acaccggagc caggcgcctg ctcatgttga agtgcgctgt tcacacccgc tccggagagc    2450
accccagcag catccagaag cagctgcagt gttgctgcca ccaccctcct gtctgcctct    2510
tcaaagtctc ctgtgacatt ttttctttgg tcagaagcca ggaactggtg tcattcctta    2570
aaagatacgt gccggggcca ggtgtggtgg ctcacgcctg taatcccagc actttgggag    2630
gccgaggcgg gcggatcaca aagtcaggac gagaccatcc tggctaacac ggtgaaaccc    2690
tgtctctact aaaaatacaa aaaaaaatta gctaggcgta gtggttggca cctatagtcc    2750
cagctactcg gaaggctgaa gcaggagaat ggtatgaatc caggaggtgg agcttgcagt    2810
gagccgagac cgtgccactg cactccagcc tgggcaacac agcgagactc cgtctcgagg    2870
aaaaaaaaag aaaagatacg tgcctgcggt gaggaagctg ggcgctgttt tcgagttcag    2930
gtgaattagc ctcaatcccc cgtgttcact tggctcccat agccctcttg atggatcacg    2990
taaaactgaa aggcagcggg gagcagacaa agatgaggtc tacactgtcc ttcatgggga    3050
ttaaagctat ggttatatta gcaccaaact tctacaaacc aagctcaggg ccccaaccct    3110
agaagggccc aaatgagaga atggtactta gggatggaaa acgggcctgg ctagagcttc    3170
gggtgtgtgt gtctgtctgt gtgtatgcat acatatgtgt gtatatatgg ttttgtcagg    3230
tgtgtaaatt tgcaaattgt ttcctttata tatgtatgta tatatatata tgaaaatata    3290
tatatatatg aaaaataaag cttaattgtc ccagaaatca ta                       3332
```

<210> SEQ ID NO 2
<211> LENGTH: 646
<212> TYPE: PRT
<213> ORGANISM: Homo sapiens

<400> SEQUENCE: 2

```
Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
```

```
                    130                 135                 140
Pro Leu Gly Ile Pro Val Asn Ser Lys Glu Pro Glu Val Ala Thr
145                 150                 155                 160

Cys Val Gly Arg Asn Gly Tyr Pro Ile Pro Gln Val Ile Trp Tyr Lys
                    165                 170                 175

Asn Gly Arg Pro Leu Lys Glu Glu Lys Asn Arg Val His Ile Gln Ser
                    180                 185                 190

Ser Gln Thr Val Glu Ser Ser Gly Leu Tyr Thr Leu Gln Ser Ile Leu
                    195                 200                 205

Lys Ala Gln Leu Val Lys Glu Asp Lys Asp Ala Gln Phe Tyr Cys Glu
210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                    245                 250                 255

Glu Pro Val Gly Met Leu Lys Glu Gly Asp Arg Val Glu Ile Arg Cys
                    260                 265                 270

Leu Ala Asp Gly Asn Pro Pro His Phe Ser Ile Ser Lys Gln Asn
275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Gly Leu Asp Leu Asp Thr Met Ile Ser Leu Leu Ser Glu Pro Gln
                    325                 330                 335

Glu Leu Leu Val Asn Tyr Val Ser Asp Val Arg Val Ser Pro Ala Ala
                    340                 345                 350

Pro Glu Arg Gln Glu Gly Ser Ser Leu Thr Leu Thr Cys Glu Ala Glu
                    355                 360                 365

Ser Ser Gln Asp Leu Glu Phe Gln Trp Leu Arg Glu Glu Thr Gly Gln
                    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                    405                 410                 415

Leu Asn Arg Thr Gln Leu Val Asn Val Ala Ile Phe Gly Pro Pro Trp
                    420                 425                 430

Met Ala Phe Lys Glu Arg Lys Val Trp Val Lys Glu Asn Met Val Leu
                    435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                    485                 490                 495

Val Glu Cys Thr Ala Ser Asn Asp Leu Gly Lys Asn Thr Ser Ile Leu
                    500                 505                 510

Phe Leu Glu Leu Val Asn Leu Thr Thr Leu Thr Pro Asp Ser Asn Thr
                    515                 520                 525

Thr Thr Gly Leu Ser Thr Ser Thr Ala Ser Pro His Thr Arg Ala Asn
                    530                 535                 540

Ser Thr Ser Thr Glu Arg Lys Leu Pro Glu Pro Glu Ser Arg Gly Val
545                 550                 555                 560
```

-continued

```
Val Ile Val Ala Val Ile Val Cys Ile Leu Val Leu Ala Val Leu Gly
                565                 570                 575
Ala Val Leu Tyr Phe Leu Tyr Lys Lys Gly Lys Leu Pro Cys Arg Arg
            580                 585                 590
Ser Gly Lys Gln Glu Ile Thr Leu Pro Pro Ser Arg Lys Ser Glu Leu
        595                 600                 605
Val Val Glu Val Lys Ser Asp Lys Leu Pro Glu Glu Met Gly Leu Leu
    610                 615                 620
Gln Gly Ser Ser Gly Asp Lys Arg Ala Pro Gly Asp Gln Gly Glu Lys
625                 630                 635                 640
Tyr Ile Asp Leu Arg His
                645

<210> SEQ ID NO 3
<211> LENGTH: 21
<212> TYPE: PRT
<213> ORGANISM: Artificial Sequence
<220> FEATURE:
<223> OTHER INFORMATION: Residues 35-55 of myelin oligodendrocyte
      glycoprotein

<400> SEQUENCE: 3

Met Glu Val Gly Trp Tyr Arg Ser Pro Phe Ser Arg Val Val His Leu
1               5                   10                  15
Tyr Arg Asn Gly Lys
                20
```

MCAM MODULATION AND USES THEREOF

CROSS REFERENCE TO RELATED APPLICATIONS

This application claims the benefit of U.S. provisional application Ser. No. 61/185,707, filed Jun. 10, 2009. This application also claims priority from Canadian application serial No. 2,676,962, and Australian patent application serial No. 2009212789, both filed Aug. 25, 2009. The contents of all these applications are incorporated herein by reference in their entirety.

SEQUENCE LISTING

Pursuant to 37 C.F.R. 1.821(c), a sequence listing is submitted herewith as an ASCII compliant text file named "Seq listing—12810.319_ST25", which was created on Jun. 8, 2010 and has a size of 17,200 bytes. The content of the aforementioned file named "Seq listing—12810.319_ST25" is hereby incorporated by reference in its entirety.

FIELD OF THE INVENTION

The present invention generally relates to melanoma cell adhesion molecule (MCAM) (also known as MelCAM, CD146 and MUC18) modulation, and uses thereof such as in the diagnosis, prevention and/or treatment of diseases and conditions associated with inflammation, such as neuroinflammation (e.g., multiple sclerosis).

BACKGROUND OF THE INVENTION

A number of disorders are associated with inflammation. For example, multiple sclerosis (MS) is an inflammatory demyelinating disease, characterized by inflammatory attacks to the central nervous system. Clinically, the disease ranges from relapsing-remitting to chronic progressive in nature.

There are few treatment regimens currently used in MS. Corticosteroids have anti-inflammatory and immunosuppressive effects. However, the responsiveness to corticosteroids declines over time, and extended use may lead to adrenal suppression, cardiovascular collapse and arrhythmias. (C. F. Lacy et al., *Drug information handbook* 8th Edition, 2001, pp. 549-551).

Interferon-β has been used as a therapy for patients with active Relapsing/Remitting Multiple Sclerosis (RRMS) since the 1980's. Recombinant IFN is available in 3 drugs: IFNβ-1b (Betaseron™) and two IFN-β-1a preparations (Avonex™ and Rebif™). These drugs reduce the rate of clinical relapse. However, neutralizing antibodies develop against these drugs rendering them ineffective with time. Also, flu-like symptoms are a prominent side effect early on in the treatment.

Glatiramer acetate (Copaxone™) is a synthetic co-polymer of tyrosine, glutamate, alanine and lysine, thought to mimic myelin basic protein (MBP) and thus, block T cell recognition of MBP (Karin N. et al., (1994) *J Exp Med.* 180(6): 2227-37). However, treatment with this drug may cause cardiovascular problems such as chest pain, flushing and tachycardia, and respiratory problems such as dyspnea (C. F. Lacy et al., supra).

Another drug that has been approved for the use in RRMS and secondary progressive MS is mitoxantrone, which however has long-term side effects causing cardiac toxicity.

Therefore, while there are a few moderately effective treatments for RRMS and secondary progressive MS, problems still exist in treating MS, and there are still no proven treatments, for example, for primary progressive MS.

Further, MS can be difficult to diagnose, current methods (e.g., MRI or analysis of CSF) being generally complicated, costly and/or involve invasive procedures.

There is therefore a continued need for improved materials and methods for the diagnosis and/or treatment of conditions/diseases associated with neuroinflammation, such as MS.

The present description refers to a number of documents, the content of which is herein incorporated by reference in their entirety.

SUMMARY OF THE INVENTION

The present invention generally relates to melanoma cell adhesion molecule (MCAM) (also known as MelCAM, CD146 and MUC18) modulation, and uses thereof such as in the diagnosis, prevention and/or treatment of diseases and conditions associated with inflammation, such as neuroinflammation (e.g., multiple sclerosis).

More specifically, in accordance with an aspect of the present invention, there is provided a method of preventing or treating an inflammatory condition in a subject, said method comprising administering to said subject an effective amount of a melanoma cell adhesion molecule (MCAM) inhibitor.

In another aspect, the present invention provides a method of inhibiting the recruitment of an inflammatory cytokine-secreting T cell precursor across the CNS endothelium comprising contacting said inflammatory cytokine-secreting T cell precursor and/or said CNS endothelium with an effective amount of an MCAM inhibitor.

In another aspect, the present invention provides a use of an MCAM inhibitor for preventing or treating an inflammatory condition in a subject.

In another aspect, the present invention provides a use of an MCAM inhibitor for the preparation of a medicament for preventing or treating an inflammatory condition in a subject.

In another aspect, the present invention provides a use of an MCAM inhibitor for inhibiting the recruitment of an inflammatory cytokine-secreting T cell precursor across the CNS endothelium.

In another aspect, the present invention provides a use of an MCAM inhibitor for the preparation of a medicament for inhibiting the recruitment of an inflammatory cytokine-secreting T cell precursor across the CNS endothelium.

In another aspect, the present invention provides an MCAM inhibitor for preventing or treating an inflammatory condition in a subject.

In another aspect, the present invention provides an MCAM inhibitor for the preparation of a medicament for preventing or treating an inflammatory condition in a subject.

In another aspect, the present invention provides a pharmaceutical composition for preventing or treating an inflammatory condition in a subject, said composition comprising an MCAM inhibitor and a pharmaceutically acceptable carrier.

In another aspect, the present invention provides a method of identifying a compound for preventing or treating an inflammatory condition, said method comprising determining whether: (a) a level of expression of an MCAM nucleic acid or encoded polypeptide; (b) a level of MCAM activity; or (c) a combination of (a) and (b); is decreased in the presence of a test compound relative to in the absence of said test compound; wherein said decrease is indicative that said test compound may be used for preventing or treating an inflammatory condition.

In another aspect, the present invention provides a method of identifying or characterizing a compound for preventing or treating an inflammatory condition, said method comprising: (a) contacting a test compound with a cell comprising a first nucleic acid comprising a transcriptionally regulatory element normally associated with an MCAM gene, operably linked to a second nucleic acid comprising a reporter gene capable of encoding a reporter protein; and (b) determining whether reporter gene expression or reporter protein activity is decreased in the presence of said test compound; wherein a decrease in said reporter gene expression or reporter protein activity is indicative that said test compound may be used for preventing or treating an inflammatory condition.

In another aspect, the present invention provides a method of identifying a compound for inhibiting the recruitment of an inflammatory cytokine-secreting T cell precursor across the CNS endothelium, said method comprising determining whether: (a) a level of expression of an MCAM nucleic acid or encoded polypeptide; (b) a level of MCAM activity; or (c) a combination of (a) and (b); is decreased in the presence of a test compound relative to in the absence of said test compound; wherein said decrease is indicative that said test compound may be used for inhibiting the recruitment of an inflammatory cytokine-secreting T cell precursor across the CNS endothelium.

In another aspect, the present invention provides a method of identifying or characterizing a compound for inhibiting the recruitment of an inflammatory cytokine-secreting T cell precursor across the CNS endothelium, said method comprising: (a) contacting a test compound with a cell comprising a first nucleic acid comprising a transcriptionally regulatory element normally associated with an MCAM gene, operably linked to a second nucleic acid comprising a reporter gene capable of encoding a reporter protein; and (b) determining whether reporter gene expression or reporter protein activity is decreased in the presence of said test compound; wherein a decrease in said reporter gene expression or reporter protein activity is indicative that said test compound may be used for inhibiting the recruitment of an inflammatory cytokine-secreting T cell precursor across the CNS endothelium.

In another aspect, the present invention provides a method for diagnosing an inflammatory condition in a first subject, said method comprising (a) determining the expression and/or activity of MCAM in a sample from said first subject (b) comparing said expression and/or activity to a corresponding reference expression and/or activity; and (c) diagnosing an inflammatory condition based on said comparison.

In another aspect, the present invention provides a method for diagnosing an inflammatory condition in a first subject, said method comprising (a) determining the amount of MCAM-expressing cells in a sample said first subject (b) comparing said amount to a corresponding reference amount; and (c) diagnosing said inflammatory condition based on said comparison.

In another aspect, the present invention provides a method for monitoring the course of treatment of a patient suffering from an inflammatory condition, the method comprising (a) determining the expression and/or activity of MCAM in a sample from said patient; wherein a decrease in said expression and/or activity relative to a corresponding expression and/or activity of MCAM determined in a biological sample obtained from said patient at an earlier time is indicative that said patient is responsive to said treatment.

In another aspect, the present invention provides a method of determining whether a subject is suffering from a relapse (exacerbation) of an inflammatory condition, said method comprising (a) determining the expression and/or activity of MCAM in a sample from said patient; wherein an increase in said expression and/or activity relative to a corresponding expression and/or activity of MCAM determined in a biological sample obtained from said patient at a time point of remission is indicative that said patient is suffering from a relapse of said inflammatory condition.

In an embodiment, the above-mentioned MCAM inhibitor blocks or inhibits MCAM/MCAM homotypic interaction.

In another embodiment, the above-mentioned inhibitor is an antibody or fragment thereof.

In another embodiment, the above-mentioned MCAM inhibitor is an siRNA molecule.

In another embodiment, the above-mentioned MCAM inhibitor blocks or inhibits MCAM-induced cell signalling.

In an embodiment, the above-mentioned CNS endothelium is exposed to an inflammatory environment. In a further embodiment, the above-mentioned inflammatory environment comprises IFN-γ and/or TNF-α. In a further embodiment, the above-mentioned inflammatory environment is associated with a neuroinflammatory condition.

In an embodiment, the above-mentioned inflammatory condition is a neuroinflammatory condition. In a further embodiment, the above-mentioned neuroinflammatory condition is an autoimmune CNS condition. In a further embodiment, the above-mentioned autoimmune CNS condition is multiple sclerosis (MS).

In another embodiment, the above-mentioned neuroinflammatory condition is associated with recruitment of an inflammatory cytokine-secreting T cell precursor to the central nervous system (CNS). In a further embodiment, the above-mentioned inflammatory cytokine-secreting T cell precursor is a memory T cell.

In an embodiment, the above-mentioned inflammatory cytokine-secreting T cell precursor has the capacity to secrete: (i) interleukin-17 (IL-17), (ii) Interferon-gamma (IFN-γ), (iii) Tumor Necrosis Factor-alpha (TNF-α), (iv) Granulocyte-macrophage colony-stimulating factor (GM-CSF), or (v) any combination of (i) to (iv), upon activation.

In another aspect, the present invention provides a method of identifying an inflammatory cytokine-secreting T cell or precursor thereof in a sample, said method comprising (i) contacting said cell with an MCAM ligand and (ii) identifying said inflammatory cytokine-secreting T cell precursor based on the binding to said MCAM ligand.

In another aspect, the present invention provides a method of purifying an inflammatory cytokine-secreting T cell or precursor thereof from a population of cells in a sample, said method comprising contacting said sample with an MCAM ligand and (ii) purifying said inflammatory cytokine-secreting T cell or precursor thereof on the basis of binding to said MCAM ligand.

In an embodiment, the above-mentioned MCAM ligand is (i) MCAM, (ii) an MCAM binding partner, (iii) an MCAM-specific antibody, or (iv) an MCAM-binding fragment of any of (i) to (iii).

In an embodiment, the above-mentioned MCAM ligand is bound to a solid support.

In another aspect, the present invention provides a kit for identifying and/or purifying an inflammatory cytokine-secreting T cell precursor from a cell sample, said kit comprising (i) an MCAM ligand and (ii) instructions for identifying and/or purifying said inflammatory cytokine-secreting T cell precursor from said sample.

In an embodiment, the above-mentioned reference expression and/or activity corresponds to an expression and/or activity determined in a sample from a control subject known to not having an inflammatory condition, and wherein a higher expression and/or activity in said sample from said first subject is indicative that said first subject has an inflammatory condition.

In another embodiment, the above-mentioned reference expression and/or activity corresponds to an expression and/or activity determined in a sample from a control subject known to have a an inflammatory condition, and wherein a comparable or higher expression and/or activity in said sample from said first subject is indicative that said first subject has an inflammatory condition.

In an embodiment, the above-mentioned reference amount corresponds to an amount determined in a sample from a control subject known to not having an inflammatory condition, and wherein a higher amount in said sample from said first subject is indicative that said first subject has an inflammatory condition.

In another embodiment, the above-mentioned reference amount corresponds to an amount determined in a sample from a control subject known to have an inflammatory condition, and wherein a comparable or higher amount in said sample from said first subject is indicative that said first subject has an inflammatory condition.

In an embodiment, the above-mentioned sample is a CNS cell, tissue or fluid. In a further embodiment, the above-mentioned CNS fluid is a cerebro-spinal fluid (CSF).

In another embodiment, the above-mentioned sample is a blood sample or a blood cell sample. In a further embodiment, the above-mentioned blood cell sample is a peripheral blood mononuclear cell (PBMC) sample.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1A: Expression of MCAM protein (105-115 kDa) in primary human cultures of BBB-ECs, as compared to umbilical vein ECs (HUVECs). n=3 different preparations, from 3 distinct donors. FIG. 1B: MCAM protein can be detected, by Western blot analysis, in detergent resistant membrane microdomains and lipid rafts of BBB-ECs (fractions 4 to 6). GM1 is shown as a marker of the lipid raft fractions (fractions 4 to 6). FIG. 1C: Expression of MCAM on the surface of BBB-ECs (dark histogram) is up-regulated in the presence of TNF-α and IFN-γ (100 U/ml, open histogram), n=3 as measured by flow cytometry;

FIGS. 4A-G show the expression of MCAM as assessed by flow cytometry on freshly isolated peripheral blood cells. Cells were labeled with anti-MCAM antibody concurrently with specific cell markers: CD4+ T lymphocytes (FIG. 4A), CD8+ T lymphocytes (FIG. 4B), CD14+ monocytes (FIG. 4C) and CD19+ B lymphocytes (FIG. 4D). FIGS. 4E and F: MCAM+ CD3+ T lymphocytes are mainly CD45RO+ and CD45RA−, indicative of a memory T cell phenotype. FIG. 4G: Overview of the markers associated with MCAM expression in ex vivo peripheral blood cells;

FIGS. 6A-E show a flow cytometry analysis of MCAM expression on ex vivo and in vitro activated (with OKT3+ CD14 monocytes+IL-2) memory lymphocytes. One million CD4+CD45RO+ lymphocytes were cultured with 500,000 autologous CD14+ monocytes in the presence of anti-CD3 (2.5 μg/ml) and IL-2 (20 units/ml) for 3 days. FIGS. 6A-D: Representative FACS histogram. FIG. 6E: Quantification of MCAM expression after in vitro activation (n>8, *** $p<0.001$) demonstrates a significant increase in the number of MCAM+ cells upon non-antigen specific TCR-mediated activation;

FIGS. 7A-D show the expression of selected cell surface markers on isolated CD4+ CD45RO+ MCAM+ and MCAM− lymphocytes after in vitro activation with OKT3+CD14 monocytes+selected cytokines. One million lymphocytes sorted according to expression of MCAM were cultured with 500 000 autologous CD14+ monocytes in the presence of anti-CD3 (2.5 μg/ml) and either IL-2 (n>7, 20 units/ml) or IL-23 (n>3, 10 ng/ml) with anti-IFN-γ (5 μ/ml) and anti-IL-4 (5 μg/ml). Following activation, CD4+ CD45RO+ cells were assessed for the Th17 marker CD161 (FIG. 7A), CD107a (FIG. 7B), CD25 (FIG. 7C) and CD69 (FIG. 7D). * $p<0.05$,  $p<0.01$, * $p<0.001$. The data demonstrates that MCAM expressing cells more frequently co-express CD161, CD107a and CD69 when stimulated with IL-2 or with IL-23;

FIGS. 8A-E show a representative flow cytometry analysis of the expression of the cytokines Interferon-gamma (FIGS. 8A-C) and IL-17 (FIGS. 8B and C) on in vitro activated CD4+ CD45RO+ T cells (FIGS. 8A-C) and on CD4+ CD45RO+ lymphocytes sorted for MCAM expression (CD4+ CD45RO+ MCAM+ vs. CD4+ CD45RO+ MCAM−) (FIGS. 8D and E). One million lymphocytes sorted according to expression of MCAM were cultured with 500 000 autologous CD14+ monocytes in the presence of anti-CD3 (2.5 μg/ml) and either IL-2 (20 units/ml). The data demonstrates that IL-17 expression and the number of IL-17 expressing cells are significantly increased in MCAM expressing CD4 memory lymphocytes;

FIGS. 9A-D show the quantification of flow cytometry analysis of the expression of selected cytokines by isolated $CD4^+$ $CD45RO^+$ $MCAM^+$ and $MCAM^-$ lymphocytes after 5 days of in vitro culture. One million lymphocytes sorted according to expression of MCAM were cultured with 500 000 autologous $CD14^+$ monocytes in the presence of anti-CD3 (2.5 µg/ml) and either IL-2 (n>7, 20 units/nil) or IL-23 (n>3, 10 ng/ml) with anti-IFN-γ (5 µ/ml) and anti-IL-4 (5 µg/ml), Following activation, $CD4^+$ $CD45RO^+$ cells were assessed for expression of IL-17 (FIG. 9A), GM-CSF (FIG. 9B), IFN-gamma (FIG. 9C) and IL-4 (FIG. 9D). * $p<0.05$,  $p<0.01$, * $p<0.001$. The data demonstrates that MCAM expression on $CD4^+$ $CD45RO^+$ lymphocytes predicts the expression of IL-17, GM-CSF and IFN-γ;

FIG. 10 shows an overview of the markers associated with in vitro activated $MCAM^+$ lymphocytes;

FIG. 11A: Representative histogram showing expression of MCAM in memory T cells expressing CD45RO and CD4 (black line) compared with isotype (solid grey) after 5 days in culture.

FIGS. 14A-C show the expression of IL-17 (FIG. 14A), IFN-γ (FIG. 14B) and IFN-γ and IL-17 (FIG. 14C) in $MCAM^+$ memory T cells originating from $MCAM^-$ sorted lymphocytes. Memory T cells expressing CD45RO and CD4 but negative for MCAM were sorted with a purity of >99% and cultured for 5 days in presence of IL-23, anti-CD3, anti-IL-4 and anti-IFN-γ (Th17 polarization conditions). Intracellular stainings for IL-17 (FIG. 14A), IFN-γ (FIG. 14B) and IL-17+IFN-γ (FIG. 14C) were performed on cultured $CD45RO^+$ $CD4^+$ $MCAM^+$ cells and $CD45RO^+$ $CD4^+$ $MCAM^-$ cells stimulated with PMA/ionomycin/Brefeldin A for 4 hours (n=3). Statistical analysis were obtained with Paired T test, ns=not significant;

FIGS. 15A and B show the expression of IL-8 on $MCAM^+$ memory T cells originating from $MCAM^+$ (FIG. 15A) and $MCAM^-$ (FIG. 15B) sorted lymphocytes. Memory T cells expressing CD45RO and CD4, and positive or negative for MCAM were sorted with a purity of >99% and cultured for 5 days in presence of IL-23, anti-CD3, anti-IL-4 and anti-IFN-γ (Th17 polarization conditions). Intracellular staining for IL-8 was performed on cultured $CD45RO^+$ $CD4^+$ $MCAM^+$ cells and $CD45RO^+$ $CD4^+$ $MCAM^-$ stimulated with PMA/ionomycin/Brefeldin A for 4 hours, n=3. Statistical analysis were obtained with Paired T test;

FIG. 16A: Proportion of $CD3^+$ $CD4^+$ $MCAM^+$ lymphocytes in 35 healthy donors and in 42 MS patients in relapse (** $p<0.0001$). FIG. 16B: Proportion of $CD3^+$ $CD8^+$ $MCAM^+$ lymphocytes in 35 healthy donors and in 42 MS patients in relapse (* $p<0.005$). FIG. 16C: Enrichment of $CD3^+$ $CD4^+$ $MCAM^+$ and $CD3^+$ $CD8^+$ $MCAM^+$ lymphocytes in the cerebro-spinal fluid (CSF) as compared to the peripheral blood in MS patients (n=5, * $p<0.005$);

FIGS. 17A-C show $CD4^+$ $CD45RO^+$ human peripheral blood lymphocytes from MS (FIG. 17B) patients and healthy controls (FIG. 17A) cultured under Th17 skewing conditions and assessed for MCAM association with IL-17 secretion (n=3 MS patients and 7 controls). One million $CD4^+$ $CD45RO^+$ lymphocytes were cultured with 500 000 autologous $CD14^+$ monocytes in the presence of anti-CD3 (2.5 µg/ml) and IL-23 (10 ng/ml) with anti-IFN-γ (5 µ/ml) and anti-IL-4 (5 µg/ml). Following activation $CD4^+$ $CD45RO^+$ cells were assessed for IL-17 and MCAM co-expression. FIGS. 17A and B: representative FACS plots from one control and one MS patient. FIG. 17C: quantification of $MCAM^+$ $IL-17^+$ cells compared to $MCAM^+$ $IL-17^+$ cells. $CD4^+$ $CD45RO^+$ $MCAM^+$ from MS patients grown under Th17 polarizing conditions express significantly more IL-17 compared to healthy controls (* $p<0.05$), presumably due to the increase proportion of $MCAM^+$ $CD4^+$ seen in MS peripheral blood;

FIGS. 18A-F: Representative FACS analysis of the presence of $MCAM^+$ lymphocytes in the spleen, LN and brain. FIG. 18G: quantification of the percentage of $MCAM^+$ $CD4^+$ and $CD8^+$ lymphocytes in the spleen, the LN and the brain of EAE animals. These data show that $MCAM^+$ lymphocytes are recruited to the brain in the course of EAE, the animal model of MS;

FIGS. 19A and B shows the nucleotide sequence of human MCAM (NCBI Reference Sequence: NM_006500.2, SEQ ID NO: 1). The coding sequence (residues 30-1970) is indicated in bold in the nucleotide sequence. FIG. 19C shows the amino acid sequence of human MCAM (NCBI Reference Sequence: NM_006491.2, SEQ ID NO: 2);

FIGS. 22A and B are representative CFSE histograms obtained by gating alternatively on $MCAM^+$ or $MCAM^-$ cells. FIG. 22C: proliferation of $MCAM^+$ versus $MCAM^-$ cells according to CFSE peaks, n=5;

FIGS. 24A-F show the effect of MCAM cross-linking on $Ca^{2+}$ mobilization in Th17 lymphocytes. Intracellular $Ca^{2+}$ mobilization following MCAM cross-linking on Th17 lymphocytes using P1H12 (mouse monoclonal anti-MCAM antibody), versus isotype-matched IgG1, anti-CD28 or OKT3 (anti-CD3). Calcium presence in the medium allows for extracellular sources to contribute to the intracytoplasmic calcium flux. Crosslinking of MCAM in the absence of extracellular calcium and magnesium result in a brief calcium influx (FIG. 24B), whereas a greater intracellular calcium influx is detected in the presence of extracellular calcium and magnesium (FIG. 24A, top panel and FIG. 24B 24C-F);

FIGS. 26A and B: $MCAM^+$ gated $IL-17^+$ cells, each point=mean of a triplicate. FIGS. 26C and D: IL-17 in supernatant as measured by ELISA, each point=mean of a triplicate;

DESCRIPTION OF ILLUSTRATIVE EMBODIMENTS

Figure 1A:
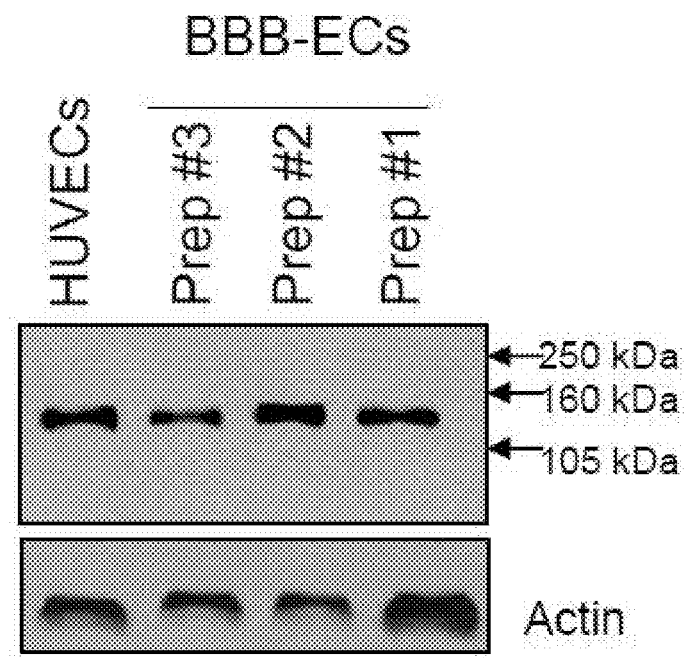
FIGS. 1A-C show the expression of melanoma cell adhesion molecule (MCAM) on endothelial cells of the blood-brain barrier (BBB-ECs).
Figure 1B:
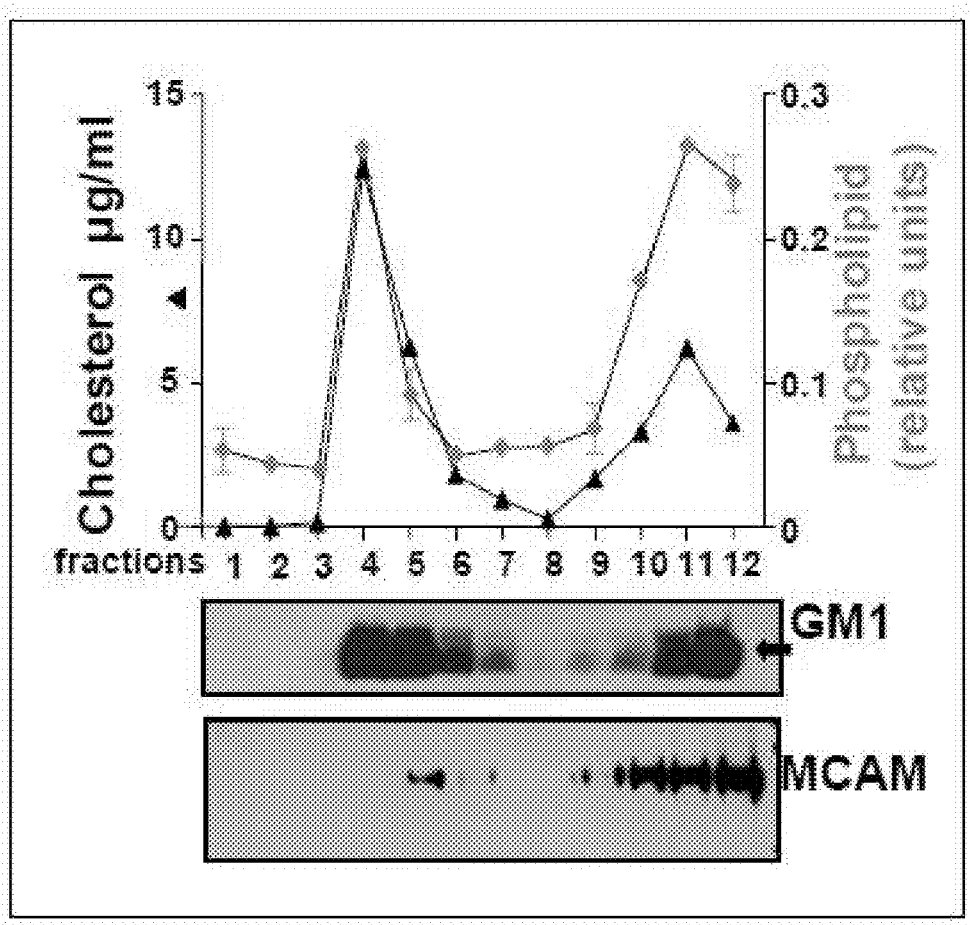

In the studies described herein, it is demonstrated that the proportion of $MCAM^+$ T cells is higher in the peripheral blood (PB) and cerebro-spinal fluid (CSF) of MS patients as compared to healthy controls, and that $MCAM^+$ T cells are enriched in the CSF compared to the PB. Furthermore, it is also shown that MCAM is expressed on human T lymphocytes that are preferentially programmed to secrete the inflammatory cytokines IL-17, IFN-γ, GM-CSF and TNF-α following activation.

Accordingly, in an aspect, the present invention provides a method of preventing or treating an inflammatory or autoimmune condition (e.g., a neuroinflammatory condition) in a subject, said method comprising administering to said subject an effective amount of a melanoma cell adhesion molecule (MCAM) inhibitor.

In another aspect, the present invention provides a method of inhibiting the recruitment of an inflammatory cytokine-secreting T cell precursor across the CNS endothelium, said method comprising contacting said inflammatory cytokine-secreting T cell precursor and/or said CNS endothelium with an effective amount of an MCAM inhibitor.

In another aspect, the present invention provides a use of an MCAM inhibitor for preventing or treating an inflammatory or autoimmune condition (e.g., a neuroinflammatory condition) in a subject. The present invention also relates to a use of an MCAM inhibitor for the preparation of a medicament for preventing or treating an inflammatory or autoimmune condition (e.g., a neuroinflammatory condition) in a subject.

In another aspect, the present invention provides a use of an MCAM inhibitor for inhibiting the recruitment of an inflammatory cytokine-secreting T cell precursor across the CNS endothelium. The present invention also relates to a use of an MCAM inhibitor for the preparation of a medicament for inhibiting the recruitment of an inflammatory cytokine-secreting T cell precursor across the CNS endothelium.

In another aspect, the present invention provides an MCAM inhibitor for preventing or treating an inflammatory or autoimmune condition (e.g., a neuroinflammatory condition) in a subject. The present invention further relates to an MCAM inhibitor for the preparation of a medicament for preventing or treating an inflammatory or autoimmune condition (e.g., a neuroinflammatory condition) in a subject.

In another aspect, the present invention provides an MCAM inhibitor for inhibiting the recruitment of an inflammatory cytokine-secreting T cell precursor across the CNS endothelium. The present invention further relates to an MCAM inhibitor for the preparation of a medicament for inhibiting the recruitment of an inflammatory cytokine-secreting T cell precursor across the CNS endothelium.

MCAM (also known as CD146 and MUC18) is a cell surface glycoprotein belonging to the immunoglobulin superfamily involved in cell adhesion, and in cohesion of the endothelial monolayer at intercellular junctions in vascular tissue. It also promotes tumor progression of many cancers including melanoma and prostate cancer. It is known to interact in a homotypic/homophilic manner and may also bind to other ligands. The nucleotide and amino acid sequences of human MCAM are shown in FIGS. 19A-C.

"Inflammatory or autoimmune condition" as used herein refers to a condition associated with inflammation and/or a dysregulated immune response. "Neuroinflammatory condition" as used herein refers to a condition associated with inflammation of the nervous system, in an embodiment the central nervous system (CNS), and which is associated with cell/tissue damage. It is typically characterized by, for example, increased glial activation, increased pro-inflammatory cytokine/chemokine levels (e.g., TNF-α, IFN-γ, IL-1β), increased blood-brain-barrier permeability, and/or increased immune cell (e.g., leukocyte) recruitment/invasion to the CNS. It refers for example to chronic neuroinflammation, such as an inflammation associated with chronic activation of cells of the immune system (i.e., autoimmune-associated neuroinflammation). Such chronic neuroinflammation is observed, for example, in multiple sclerosis.

In an embodiment, the above-mentioned neuroinflammatory condition is multiple sclerosis (MS) and clinically isolated syndromes suggestive of MS, in a further embodiment active MS (i.e., relapse).

An "effective amount" refers to an amount effective, at dosages and for periods of time necessary, to achieve the desired prophylactic or therapeutic result. An effective amount refers to the amount of active compound or pharmaceutical agent that elicits the biological or medicinal response in a tissue, system, animal, individual or human that is being sought by a researcher, veterinarian, medical doctor or other clinician, which includes one or more of the following:

(A) Preventing the disease; for example, preventing an inflammatory disease, such as a neuroinflammatory disease, condition or disorder in an individual that may be predisposed to the disease, condition or disorder but does not yet experience or display the pathology or symptomatology of the disease, (B) Inhibiting the disease; for example, inhibiting an inflammatory disease, such as a neuroinflammatory disease, condition or disorder in an individual that is experiencing or displaying the pathology or symptomatology of the disease, condition or disorder (i.e., arresting further development of the pathology and/or symptomatology), and (C) Ameliorating the disease; for example, ameliorating an inflammatory disease, such as a neuroinflammatory disease, condition or disorder in an individual that is experiencing or displaying the pathology or symptomatology of the disease, condition or disorder (i.e., reversing the pathology and/or symptomatology).

The amount of the MCAM inhibitor which is effective in the prevention and/or treatment of a particular disease, disorder or condition (e.g., an inflammatory disease, such as a neuroinflammatory disease, disorder or condition) will depend on the nature and severity of the disease, the chosen prophylactic/therapeutic regimen, the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 1000 mg/kg of body weight/day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a patient, in the context of the present invention should be sufficient to effect a beneficial prophylactic and/or therapeutic response in the patient over time. The size of the dose also will be determined by the existence, nature, and extent of any adverse side-effects that accompany the administration. Effective doses may be extrapolated from dose response curves derived from in vitro or animal model test systems. For example, in order to obtain an effective mg/kg dose for humans based on data generated from rat studies, the effective mg/kg dosage in rat may be divided by six.

In an embodiment, the above-mentioned treatment comprises the use/administration of more than one (i.e. a combination of) active/therapeutic agent, one of which being the above-mentioned MCAM inhibitor. The combination of prophylactic/therapeutic agents and/or compositions of the present invention may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) is used/administered in combination with one or more agent(s) currently used to prevent or treat the disorder in question (e.g., an inflammatory disease, such as a neuroinflammatory disease, such as MS).

As used herein, the term "MCAM inhibitor" includes any compound able to directly or indirectly affect the regulation of MCAM by reducing for example the expression of MCAM (i.e., transcription and/or the translation), or an MCAM activity. It includes intracellular as well as extracellular MCAM inhibitors. Without being so limited, such inhibitors include siRNA, antisense molecules, proteins, peptides, small molecules, antibodies, etc.

As used herein the terms "MCAM activity" and "MCAM function" refer to detectable enzymatic, biochemical or cellular activity attributable to MCAM. MCAM activity may also be measured by protein-protein binding assay using purified MCAM and a purified MCAM ligand (e.g., MCAM itself). MCAM activity may also be measured in a cell adhesion assay.

MCAM activity could also be indirectly measured by evaluating the level of expression of MCAM, or a fragment thereof, in cells as well as in a biological sample (tissue, organ, fluid). MCAM expression levels could be determined at the polypeptide and/or nucleic acid levels using any standard methods known in the art (see below). MCAM activity could also be indirectly measured by evaluating the level of expression or activity of a reporter gene (e.g., luciferase, B-galactosidase, alkaline phosphatase, GFP) operably linked to a transcriptionally regulatory element normally associated with a MCAM gene.

As used herein, "inflammatory cytokine-secreting T cell precursor" refers to a T cell having the potential/capacity to perform effector functions such as to secrete inflammatory cytokines (e.g., IL-17, IFN-γ) and/or mediate cytotoxic killing, for example following activation/stimulation (e.g., T cell receptor (TCR)-mediated activation/stimulation). In an embodiment, the above-mentioned inflammatory cytokine-secreting T cell precursor express one or more of the markers depicted in FIGS. 7A-D, 8A, 8B, 9A-D and 10 (e.g., CD161, CD107a and CD69).

In an embodiment, the above-mentioned MCAM inhibitor is an antisense molecule.

Generally, the principle behind antisense technology is that an antisense molecule hybridizes to a target nucleic acid and effects modulation of gene expression such as transcription, splicing, translocation of the RNA to the site of protein translation, translation of protein from the RNA. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi is a form of antisense-mediated gene silencing involving the introduction of dsRNA (typically of less than 30 nucleotides in length, and generally about 19 to 24 nucleotides in length) leading to the sequence-specific reduction of targeted endogenous mRNA levels, here the RNA transcript of the MCAM gene. Such dsRNA are generally substantially complementary to at least part of an RNA transcript of the MCAM gene. Another example of modulation of gene expression is the RNA analogue Locked Nucleic Acid (LNA). Other examples relate to double stranded nucleic acid molecules including small nucleic acid molecules, such as short interfering nucleic acid (siNA), short interfering RNA (sRNA), micro-RNA (miRNA). The use of single stranded antisense oligonucleotides (ASO) is also encompassed by the method of the present invention. Sequence-specificity makes antisense compounds extremely attractive as therapeutics to selectively modulate the expression of genes involved in the pathogenesis of any one of a variety of diseases.

Chemically modified nucleosides, such as 2'-substituted arabinonucleosides (e.g., 2'F-ANA) and 2'-substituted RNA (e.g., 2'F-RNA), are routinely used for incorporation into antisense compounds to enhance one or more properties, such as nuclease resistance, pharmacokinetics or affinity for a target RNA.

As used herein "antisense molecule" is meant to refer to an oligomeric molecule, particularly an antisense oligonucleotide for use in modulating the activity or function of nucleic acid molecules encoding an MCAM polypeptide (e.g., the polypeptide of SEQ ID NO: 2), ultimately modulating the amount of MCAM produced in cells (e.g., CNS cells, immune cells). This is accomplished by providing oligonucleotide molecules which specifically hybridize with one or more nucleic acids encoding MCAM (e.g., the nucleic acid of SEQ ID NO: 1). As used herein, the term "nucleic acid encoding an MCAM polypeptide" encompasses DNA encoding said polypeptide, RNA (including pre-mRNA and mRNA) transcribed from such DNA, and also cDNA derived from such RNA (e.g., a nucleic acid comprising the coding sequence of the nucleotide sequence set forth in SEQ ID NO: 1). The specific hybridization of an oligomeric compound with its target nucleic acid interferes with the normal function of the nucleic acid. The overall effect of such interference with target nucleic acid function is modulation of the expression of MCAM. In the context of the present invention, "modulation" means either an increase (stimulation) or a decrease (inhibition) in the expression of a gene.

In the context of this invention, "hybridization" means hydrogen bonding between complementary nucleoside or nucleotide bases. Terms "specifically hybridizable" and "complementary" are the terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed. Such conditions may comprise, for example, 400 mM NaCl, 40 mM PIPES pH 6.4, 1 mM EDTA, at 50 to 70° C. for 12 to 16 hours, followed by washing. The skilled person will be able to determine the set of conditions most appropriate for a test of complementarity of two sequences in accordance with the ultimate application of the hybridized nucleotides.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. Examples of modified nucleotides include a 2'-O-methyl modified nucleotide, a nucleotide comprising a 5'-phosphorothioate group, a terminal nucleotide linked to a cholesteryl derivative, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate and a non-natural base comprising nucleotide.

Methods to produce antisense molecules directed against a nucleic acid are well known in the art. The antisense molecules of the invention may be synthesized in vitro or in vivo.

Reagents and kits for performing RNAi are available commercially from for example Ambion Inc. (Austin, Tex., USA), New England Biolabs Inc. (Beverly, Mass., USA) and Invitrogen (Carlsbad, Calif., USA).

The antisense molecule may be expressed from recombinant viral vectors, such as vectors derived from adenoviruses, adeno-associated viruses, retroviruses, herpesviruses, and the like. Such vectors typically comprises a sequence encoding an antisense molecule of interest (e.g., a dsRNA specific for MCAM) and a suitable promoter operatively linked to the antisense molecule for expressing the antisense molecule.

The vector may also comprise other sequences, such as regulatory sequences, to allow, for example, expression in a specific cell/tissue/organ, or in a particular intracellular environment/compartment. Methods for generating, selecting and using viral vectors are well known in the art.

Antisense molecules (siRNA and shRNA) inhibiting the expression of human MCAM are known in the art (see, for example, Bardin et al., *Arterioscler Thromb Vasc Biol.* 2009 May; 29(5):746-53. Epub 2009 Feb. 19), and are commercially available, for example from Invitrogen (MCAM Stealth RNAi™ siRNA, Cat. Nos. HSS106378, HSS106379 and HSS106380) and Applied Biosystems (siRNA ID Nos. s8571, s8572 and s8573). Also, several providers (e.g., InvivoGen, Qiagen, Ambion, Inc.) offer custom-made antisense synthesis services.

In an embodiment, the above-mentioned MCAM inhibitor is an MCAM antibody or MCAM-binding fragment thereof.

By "MCAM antibody" or "anti-MCAM" in the present context is meant an antibody capable of detecting (i.e., binding to) a MCAM protein or an MCAM protein fragment. In an embodiment, the above-mentioned antibody inhibits the biological activity of MCAM, such as MCAM binding to one or more of its ligands (including MCAM/MCAM homotypic interaction), or MCAM-mediated cell adhesion/recruitment. In another embodiment, the MCAM protein fragment is an extracellular domain of MCAM.

In an embodiment, the antibody specifically binds to (interacts with) an MCAM polypeptide (e.g., the polypeptide of SEQ ID NO: 2) and displays no substantial binding to other naturally occurring proteins other than the ones sharing the same antigenic determinants as an MCAM polypeptide. The term antibody or immunoglobulin is used in the broadest sense, and covers monoclonal antibodies (including full-length monoclonal antibodies), polyclonal antibodies, multi-specific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, $V_H$ regions ($V_H$, $V_H$-$V_H$), anticalins, PepBodies, antibody-T-cell epitope fusions (Troybodies) or Peptibodies. Additionally, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody as used herein encompasses polyclonal, monoclonal antibodies and antibody variants such as single-chain antibodies, humanized antibodies, chimeric antibodies and immunologically active fragments of antibodies (e.g., Fab and Fab' fragments) which inhibit or neutralize their respective interaction domains in Hyphen and/or are specific thereto.

Polyclonal antibodies are preferably raised in animals by multiple subcutaneous (s.c.), intravenous (i.v.) or intraperitoneal (i.p.) injections of the relevant antigen (e.g., an MCAM polypeptide or a fragment thereof) with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfo-succinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen (e.g., an MCAM polypeptide or a fragment thereof, such as a fragment comprising the region involved in homotypic interaction), immunogenic conjugates, or derivatives by combining the antigen or conjugate (e.g., 100 μg for rabbits or 5 μg for mice) with 3 volumes of Freund's complete adjuvant and injecting the solution intradermally at multiple sites. One month later the animals are boosted with the antigen or conjugate (e.g., with ⅕ to 1/10 of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025, 155 and 6,077,677 as well as U.S. Patent Application Publication Nos. 2002/0160970 and 2003/0083293.

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In an embodiment, the above-mentioned antibody blocks or interferes with MCAM homotypic interaction, for example by competing for an MCAM binding domain or by sterically hindering an MCAM binding domain.

MCAM inhibitors may also be in the form of non-antibody-based scaffolds, such as avimers (Avidia); DARPins (Molecular Partners); Adnectins (Adnexus), Anticalins (Pieris) and Affibodies (Affibody). The use of alternative scaffolds for protein binding is well known in the art (see, for example, Binz and Plückthun, 2005, *Curr. Opin. Biotech.* 16: 1-11).

Antibodies directed against MCAM are known in the art (see, for example, Bardin et al., *Arterioscler Thromb Vasc Biol.* 2009 May; 29(5):746-53. Epub 2009 Feb. 19; PCT publication No. WO/2004/007550; Mills et al., *Cancer Research* 62, 5106-5114, Sep. 1, 2002) and are commercially available, for example from Biocytex (Cat. No. 5020-P100T, 5010-P100T, 5030-P100T, 5040-P100T and 5050-P100T), Sigma-Aldrich (Cat. No. HPA008848), Epitomics (Cat. No. 2505-1), Novus Biologicals (Cat. No. NBP1-40575, NBP1-35488, NBP1-35487), BioLegend (Cat. No. 342001), AbD-Serotec (Cat. No. MCA2141T), Sino Biological (Cat. No. 10115-RP01), R & D Systems (Cat. No. MAB932), EMD Biosciences (Cat. No. IM1010) and Abgent (Cat. No. AP2767A).

In an embodiment, the above-mentioned MCAM inhibitor is a peptide blocking blocks or interfering with MCAM homotypic interaction, such as a peptide binding to and competing for an MCAM binding domain.

In an embodiment, the above-mentioned MCAM inhibitor is a peptide blocking blocks or interfering with MCAM heterotypic interaction, such as a peptide binding to and competing for an MCAM binding domain.

In an embodiment, the above-mentioned MCAM inhibitor is a compound modulating MCAM expression, e.g., a compound inhibiting MCAM upregulation such as the endothelin-B receptor antagonist BQ788 (Mangahas, et al., *J. Invest. Dermatol.* (2004) 123: 1135-1139)

In another aspect, the present invention provides a composition comprising the above-mentioned MCAM inhibitor and a pharmaceutically acceptable carrier or excipient. Such compositions may be prepared in a manner well known in the pharmaceutical art. Supplementary active compounds can also be incorporated into the compositions. As used herein "pharmaceutically acceptable carrier" or "excipient" includes any and all solvents, buffers, dispersion media, coatings, antibacterial and antifungal agents, isotonic and absorption delaying agents, and the like that are physiologically compatible. The carrier can be suitable, for example, for intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration (see Remington: The Science and Practice of Pharmacy by Alfonso R. Gennaro, 2003, $21^{th}$ edition, Mack Publishing Company).

Formulations suitable for oral administration may include (a) liquid solutions, such as an effective amount of active agent(s)/composition(s) suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds/compositions of the invention include ethylenevinyl acetate copolymer particles, osmotic pumps, implantable infusion systems, and liposomes. Formulations for inhalation may contain excipients, (e.g., lactose) or may be aqueous solutions containing, for example, polyoxyethylene-9-lauryl ether, glycocholate and deoxycholate, or may be oily solutions for administration in the form of nasal drops, or as a gel.

For preparing pharmaceutical compositions from the compound(s)/composition(s) of the present invention, pharmaceutically acceptable carriers are either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired. The powders and tablets may typically contain from 5% or 10% to 70% of the active compound/composition. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use are prepared by dissolving the MCAM inhibitor in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

In an embodiment, the MCAM inhibitor is formulated/administered such that it comes into contact with neural cells or neural tissue, such as central nervous system (CNS) cells or tissue. Such tissue includes brain and spinal cord (e.g., cervical, thoracic, or lumbar) tissue. As such, in embodiments, the MCAM inhibitor can be administered to treat neural cells/tissue in vivo via direct intracranial injection or injection into the cerebrospinal fluid (e.g., intrathecal injection). Alternatively, the MCAM inhibitor can be administered systemically (e.g. intravenously) and may come into contact with the affected neural tissue via lesions (where the blood-brain barrier is compromised), or, in a further embodiment, may be in a form capable of crossing the blood-brain barrier and entering the neural system (e.g., CNS). Further, in an embodiment, a composition of the invention may be formulated for such administration to neural cells/tissue.

The composition may also contain more than one active compound for the particular indication being treated, preferably those with complementary activities that do not adversely affect each other. It may be desirable to use the above-mentioned MCAM inhibitor or composition in addition to one or more agents currently used to prevent or treat the disorder in question. The above-mentioned MCAM inhibitor may be formulated in a single composition or in several individual compositions which may be co-administered in the course of the treatment.

The invention further provides a kit or package comprising the above-mentioned MCAM inhibitor or the above-mentioned composition, together with instructions for (i) the prevention and/or treatment of an inflammatory or autoimmune condition (e.g., a neuroinflammatory condition) in a subject and/or (ii) for inhibiting the recruitment of an inflammatory cytokine-secreting T cell precursor across the CNS endothelium. The kit may further comprise, for example, containers, buffers, a device (e.g., syringe) for administering the MCAM inhibitor or a composition comprising same.

Given the correlation between MCAM expression/activity and inflammation, compounds which are capable of decreasing MCAM expression/activity may be used for the prevention and/or treatment of inflammatory conditions, such as neuroinflammatory conditions. Therefore, the invention further relates to screening methods (e.g., in vitro methods) for the identification and characterization of compounds capable of decreasing/inhibiting MCAM expression and/or activity, which may be used for the prevention and/or treatment of inflammatory conditions, such as neuroinflammatory conditions.

In another aspect, the present invention provides a method of identifying a compound for preventing or treating an inflammatory condition, such as a neuroinflammatory condition, the method comprising determining whether: (a) a level of expression of an MCAM nucleic acid or encoded polypeptide; (b) a level of MCAM activity; or (c) a combination of (a) and (b), is decreased in the presence of a test compound relative to in the absence of said test compound; wherein said decrease is indicative that said test compound may be used for preventing or treating an inflammatory condition, such as a neuroinflammatory condition.

In another aspect, the present invention provides a method of identifying or characterizing a compound for preventing or treating an inflammatory condition, such as a neuroinflammatory condition, the method comprising: (a) contacting a test compound with a cell comprising a first nucleic acid comprising a transcriptionally regulatory element normally associated with an MCAM gene, operably linked to a second nucleic acid comprising a reporter gene capable of encoding a reporter protein; and (b) determining whether reporter gene expression or reporter protein activity is decreased in the presence of the test compound; wherein a decrease in said reporter gene expression or reporter protein activity is indicative that said test compound may be used for preventing or treating an inflammatory condition, such as a neuroinflammatory condition.

In another aspect, the present invention provides a method of identifying a compound for inhibiting the recruitment of an inflammatory cytokine-secreting T cell precursor across the CNS endothelium, the method comprising determining whether: (a) a level of expression of an MCAM nucleic acid or encoded polypeptide; (b) a level of MCAM activity; or (c) a combination of (a) and (b), is decreased in the presence of a test compound relative to in the absence of said test compound; wherein said decrease is indicative that said test compound may be used for inhibiting the recruitment of an inflammatory cytokine-secreting T cell precursor across the CNS endothelium.

In another aspect, the present invention provides a method of identifying or characterizing a compound for inhibiting the recruitment of an inflammatory cytokine-secreting T cell precursor across the CNS endothelium, the method comprising: (a) contacting a test compound with a cell comprising a first nucleic acid comprising a transcriptionally regulatory element normally associated with a MCAM gene, operably linked to a second nucleic acid comprising a reporter gene capable of encoding a reporter protein; and (b) determining whether reporter gene expression or reporter protein activity is decreased in the presence of the test compound: wherein a decrease in said reporter gene expression or reporter protein activity is indicative that the test compound may be used for inhibiting the recruitment of an inflammatory cytokine-secreting T cell precursor across the CNS endothelium.

In an embodiment, the above-mentioned MCAM activity is a binding activity (e.g., the binding of MCAM to one of its ligand, MCAM/MCAM homotypic binding), wherein a decrease in said binding in the presence of the test compound is indicative that the test compound may be used for (i) preventing or treating an inflammatory or autoimmune condition (e.g., a neuroinflammatory condition), and/or (ii) inhibiting the recruitment of an inflammatory cytokine-secreting T cell precursor across the CNS endothelium. In another embodiment, the above-mentioned MCAM activity is determined using a cell (e.g., lymphocyte) adhesion/recruitment assay, wherein a decrease in adhesion/recruitment in the presence of the test compound is indicative that the test compound may be used for (i) preventing or treating an inflammatory or autoimmune condition (e.g., a neuroinflammatory condition), and/or (ii) inhibiting the recruitment of an inflammatory cytokine-secreting T cell precursor across the CNS endothelium.

The above-noted screening method or assay may be applied to a single test compound or to a plurality or "library" of such compounds (e.g., a combinatorial library). Any such compounds may be utilized as lead compounds and further modified to improve their therapeutic, prophylactic and/or pharmacological properties for preventing and/or treating an inflammatory or autoimmune condition (e.g., a neuroinflammatory condition).

Test compounds (drug candidates) may be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Screening assay systems may comprise a variety of means to enable and optimize useful assay conditions. Such means may include but are not limited to: suitable buffer solutions, for example, for the control of pH and ionic strength and to provide any necessary components for optimal activity and stability (e.g., protease inhibitors), temperature control means for optimal activity and/or stability, of MCAM, and detection means to enable the detection of its activity. A variety of such detection means may be used, including but not limited to one or a combination of the following: radiolabelling, antibody-based detection, fluorescence, chemiluminescence, spectroscopic methods (e.g., generation of a product with altered spectroscopic properties), various reporter enzymes or proteins (e.g., horseradish peroxidase, green fluorescent protein), specific binding reagents (e.g., biotin/(strept)avidin), and others.

As noted above, the invention further relates to methods for the identification and characterization of compounds capable of decreasing MCAM gene expression. Such a method may comprise assaying MCAM gene expression in the presence versus the absence of a test compound. Such gene expression may be measured by detection of the corresponding RNA or protein, or via the use of a suitable reporter construct comprising one or more transcriptional regulatory element(s) normally associated with a MCAM gene, operably-linked to a reporter gene.

A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences.

Generally, operably-linked DNA sequences are contiguous and, where necessary to join two protein coding regions, in reading frame. However, since, for example, enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals which induce or control transcription of protein coding sequences with which they are operably-linked. The expression of such a reporter gene may be measured on the transcriptional or translational level, e.g., by the amount of RNA or protein produced. RNA may be detected by for example Northern analysis or by the reverse transcriptase-polymerase chain reaction (RT-PCR) method (see for example Sambrook et al. (1989) Molecular Cloning: A Laboratory Manual ($2^{nd}$ edition), Cold Spring Harbor Laboratory Press, Cold Spring Harbor, N.Y., USA).

Protein levels may be detected either directly using affinity reagents (e.g., an antibody or fragment thereof (for methods, see for example Harlow, E. and Lane, D (1988) Antibodies: A Laboratory Manual, Cold Spring Harbor Laboratory Press, Cold Spring Harbor, N.Y.); a ligand which binds the protein) or by other properties (e.g., fluorescence in the case of green fluorescent protein) or by measurement of the protein's activity, which may entail enzymatic activity to produce a detectable product (e.g., with altered spectroscopic properties) or a detectable phenotype (e.g., alterations in cell growth/function). Suitable reporter genes include but are not limited to chloramphenicol acetyltransferase, beta-D galactosidase, luciferase, or green fluorescent protein (GFP).

MCAM protein expression levels may be determined using any standard methods known in the art. Non-limiting examples of such methods include Western blot, tissue microarray, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microscopy, fluorescence-activated cell sorting (FACS), flow cytometry, and assays based on a property of the protein including but not limited to DNA binding, ligand binding, or interaction with other protein partners.

Methods to determine MCAM nucleic acid (mRNA) levels are known in the art, and include for example polymerase chain reaction (PCR), reverse transcriptase-PCR (RT-PCR) (e.g., as in Example 3 below), in situ PCR, SAGE, quantitative PCR (q-PCR), in situ hybridization, Southern blot, Northern blot, sequence analysis, microarray analysis, detection of a reporter gene, or other DNA/RNA hybridization platforms. For RNA expression, preferred methods include, but are not limited to: extraction of cellular mRNA and Northern blotting using labeled probes that hybridize to transcripts encoding all or part of one or more of the genes of this invention; amplification of mRNA expressed from one or more of the genes of this invention using gene-specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization.

In embodiments, competitive screening assays may be done by combining an MCAM polypeptide, or a fragment thereof (an MCAM binding domain) and a probe to form a probe: MCAM binding domain complex in a first sample followed by adding a test compound. The binding of the test compound is determined, and a change, or difference in binding of the probe in the presence of the test compound indicates that the test compound is capable of binding to the MCAM binding domain and potentially modulating MCAM activity.

The binding of the test compound may be determined through the use of competitive binding assays. In this embodiment, the probe is labeled with an affinity label such as biotin. Under certain circumstances, there may be competitive binding between the test compound and the probe, with the probe displacing the candidate agent. In one case, the test compound may be labeled. Either the test compound, or a compound of the present invention, or both, is added first to the MCAM binding domain for a time sufficient to allow binding to form a complex.

The assay may be carried out in vitro utilizing a source of MCAM which may comprise a naturally isolated or recombinantly produced MCAM (or a variant/fragment thereof), in preparations ranging from crude to pure. Such assays may be performed in an array format. In certain embodiments, one or a plurality of the assay steps are automated.

A homolog, variant and/or fragment of MCAM which retains activity (e.g., a binding activity) may also be used in the methods of the invention.

"Homology", "homologous" and "homolog" refer to sequence similarity between two polypeptide molecules. Homology can be determined by comparing each position in the aligned sequences. A degree of homology between amino acid sequences is a function of the number of identical or matching amino acids at positions shared by the sequences. Two amino acid or nucleotide sequences are considered "substantially identical" if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%, e.g., with a reference sequence in question, e.g., any of the sequences described herein. As used herein, a given percentage of homology between sequences denotes the degree of sequence identity in optimally aligned sequences. An "unrelated" or "non-homologous" sequence shares less than 40% identity, though preferably less than about 25% identity, with a reference sequence in question, e.g., any of the sequences described herein.

Two protein or nucleic acid sequences are considered substantially identical if, when optimally aligned, they share at least about 70% sequence identity. In alternative embodiments, sequence identity may for example be at least 75%, at least 80%, at least 85%, at least 90%, or at least 95%, with a reference sequence in question, e.g., any of the sequences described herein. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

The present inventors have shown in human samples and a neuroinflammatory mouse model (EAE) that MCAM is expressed or overexpressed on CNS cells and on CNS and peripheral immune cells (CD4 and CD8 T lymphocytes) in neuroinflammatory conditions, and thus that MCAM expression may be used as a biological marker for the detection and characterization of inflammatory conditions, such as neuroinflammatory conditions.

Therefore, in another aspect, the invention relates to the diagnosis and prognostic of an inflammatory condition, such as a neuroinflammatory condition. The invention thus provides a method for diagnosing an inflammatory condition, such as a neuroinflammatory condition, in a subject based on the expression and/or activity of MCAM determined in a sample (e.g., a CNS sample or a blood/blood cell sample) from the subject. The expression and activity of MCAM in the sample may be determined using the assays/methods described above.

In an embodiment, the method may comprise determining whether MCAM activity and/or expression is modulated, e.g., upregulated or increased, relative to a control/reference activity or expression. In yet another embodiment, the control MCAM expression or activity can be selected from an established standard, a corresponding MCAM expression or activity determined in the subject (in a sample from the subject) at an earlier time; a corresponding MCAM expression or activity determined in a control subject known to not having a neuroinflammatory condition (e.g., a healthy subject). In such cases, an increased or higher expression and/or activity in the sample from the subject relative to the control activity or expression is indicative that the subject has a neuroinflammatory condition. "Higher expression" as used herein refers to (i) higher expression of MCAM on one or more given cells present in the sample and/or (ii) increased amount (absolute or relative amount) of MCAM-expressing/positive cells in the sample.

In another embodiment, the control MCAM expression or activity is a corresponding expression or activity in a control subject known to have an inflammatory condition, such as a neuroinflammatory condition. In such a case, a comparable or higher MCAM expression and/or activity in a sample from the subject relative to the control expression or activity is indicative that the subject has a neuroinflammatory condition.

Methods for normalizing the level of expression of a gene are well known in the art. For example, the expression level of a gene of the present invention can be normalized on the basis of the relative ratio of the mRNA level of this gene to the mRNA level of a housekeeping gene or the relative ratio of the protein level of the protein encoded by this gene to the protein level of the housekeeping protein, so that variations in the sample extraction efficiency among cells or tissues are reduced in the evaluation of the gene expression level. A "housekeeping gene" is a gene the expression of which is substantially the same from sample to sample or from tissue to tissue, or one that is relatively refractory to change in response to external stimuli. A housekeeping gene can be any RNA molecule other than that encoded by the gene of interest that will allow normalization of sample RNA or any other marker that can be used to normalize for the amount of total RNA added to each reaction. For example, the GAPDH gene, the G6PD gene, the actin gene, ribosomal RNA, 36B4 RNA, PGK1, RPLP0, or the like, may be used as a housekeeping gene.

Methods for calibrating the level of expression of a gene are well known in the art. For example, the expression of a gene can be calibrated using reference samples, which are commercially available. Examples of reference samples include, but are not limited to: Stratagene™ QPCR Human Reference Total RNA, Clontech™ Universal Reference Total RNA, and XpressRef™ Universal Reference Total RNA.

In an embodiment, the above-mentioned method comprises determining the level of an MCAM nucleic acid (e.g., the nucleic acid of SEQ ID NO: 1) in the sample. In another embodiment, the above-mentioned method comprises determining the level of an MCAM polypeptide (e.g., the polypeptide of SEQ ID NO: 2) in the sample. In an embodiment, the level of an MCAM polypeptide is determined using an anti-MCAM antibody.

"Sample" or "biological sample" refers to any solid or liquid sample isolated from a live being. In a particular embodiment, it refers to any solid or liquid sample isolated from a human, such as a biopsy material, blood, saliva, synovial fluid, urine, amniotic fluid and cerebrospinal fluid. In an embodiment, the above-mentioned sample is obtained from the central nervous system (e.g., a CNS-derived sample such as a CNS cell, tissue and/or fluid). In a further embodiment, the CNS cell is obtained by a biopsy. In a further embodiment, the CNS cell is a CNS endothelial cell. In another embodiment, the above-mentioned CNS fluid is cerebro-spinal fluid (CSF).

In another embodiment, the above-mentioned sample is a blood sample or a blood cell sample (a blood-derived sample). In a further embodiment, the above-mentioned blood cell sample is a peripheral blood mononuclear cell (PBMC) sample. In an embodiment, the above-mentioned blood or blood cell sample comprises T cells, such as $CD4^+$ and/or $CD8^+$ T cells. In an embodiment, the above-mentioned blood or blood cell sample may be submitted to one or more cell depletion or enrichment steps, so as to enrich the sample in one or more cell types of interest (e.g., T cells, such as $CD4^+$ and/or $CD8^+$ T cells).

In an embodiment, the above-mentioned method comprises determining the amount of $MCAM^+$-cells in said sample and comparing it to a corresponding amount in a control/reference sample. Accordingly, in another aspect, the present invention provides a method for diagnosing an inflammatory condition, such as a neuroinflammatory condition, in a first subject, said method comprising (a) determining the extent/amount of MCAM expression (e.g., the number of MCAM-expressing cells and/or the intensity of MCAM expression per cell) in a sample said first subject (b) comparing said amount to a corresponding reference amount; and (c) diagnosing an inflammatory condition, such as a neuroinflammatory condition, based on said comparison.

In an embodiment, the above-mentioned reference amount corresponds to an amount determined in a sample from a control subject known not to be suffering from an inflammatory condition, such as a neuroinflammatory condition, and wherein a higher amount in said sample from said first subject is indicative that said first subject has a neuroinflammatory condition.

In another embodiment, the above-mentioned reference amount corresponds to an amount determined in a sample from a control subject known to be suffering from an inflammatory condition, such as a neuroinflammatory condition, and wherein a comparable or higher amount in said sample from said first subject is indicative that said first subject has an inflammatory condition, such as a neuroinflammatory condition.

In another aspect, the present invention provides a method for monitoring the course of treatment of a patient suffering from an inflammatory condition, the method comprising (a) determining the expression and/or activity of MCAM in a sample from said patient; wherein a decrease in said expression and/or activity relative to a corresponding expression and/or activity of MCAM determined in a biological sample obtained from said patient at an earlier time is indicative that said patient is responsive to said treatment. In an embodiment, a similar level or an decrease in said expression and/or activity relative to a corresponding expression and/or activity of MCAM determined in a biological sample obtained from said patient at an earlier time is indicative that said patient is not responsive to said treatment. The treatment regimen (e.g., drug, dose) may thus be adapted accordingly.

In another aspect, the present invention provides a method of determining whether a subject is suffering from a relapse (exacerbation) of an inflammatory condition, said method comprising (a) determining the expression and/or activity of MCAM in a sample from said patient; wherein an increase in said expression and/or activity relative to a corresponding expression and/or activity of MCAM determined in a biological sample obtained from said patient at a time point of remission is indicative that said patient is suffering from a relapse of said inflammatory condition. The treatment regimen (e.g., drug, dose) may thus be adapted accordingly.

In an embodiment, the above-mentioned expression and/or activity of MCAM is determined based on the amount of MCAM-expressing cells in said sample. In a further embodiment, the above-mentioned amount is a relative amount (e.g., the proportion of MCAM-expressing cells relative to the total cells present in the sample, or relative to another cell type present in the sample).

In an embodiment, the above-mentioned neuroinflammatory condition is MS, in a further embodiment active MS (i.e., relapse).

In an embodiment, the methods of diagnosis/prognostication noted above may be performed in conjunction with the therapeutic/prophylactic methods noted above, for preventing and/or treating an inflammatory condition, such as a neuroinflammatory condition, in a subject. Such a method thus comprises the diagnosis or prognostication of an inflammatory condition, such as a neuroinflammatory condition, in a subject and, in accordance with the diagnosis/prognosis, decreasing MCAM levels in the subject (e.g., in a cell, tissue or organ of the subject) thereby to prevent or treat the inflammatory condition, such as a neuroinflammatory condition.

The present invention also provides a kit or package comprising a reagent useful for determining MCAM expression and activity (e.g., a ligand that specifically binds an MCAM polypeptide such as an anti-MCAM antibody, or a ligand that specifically binds an MCAM nucleic acid such as an oligonucleotide). Such kit may further comprise, for example, instructions for the prognosis and/or diagnosis of an inflammatory condition, such as a neuroinflammatory condition, control samples, containers, reagents useful for performing the methods (e.g., buffers, enzymes), etc.

As used herein the term "subject" is meant to refer to any animal, such as a mammal including human, mice, rat, dog, cat, pig, cow, monkey, horse, etc. In an embodiment, the above-mentioned subject is a human.

The present inventors have further determined that MCAM expression permits the identification of T cells having the capacity or the potential to perform effector functions, for example to produce various inflammatory cytokines (e.g., IL-17 and IFN-γ), upon activation (e.g., TCR-mediated activation).

Accordingly, in another aspect, the present invention provides a method of identifying an inflammatory cytokine-secreting T cell or precursor thereof in a sample, said method comprising identifying MCAM-expressing cells in the sample, for example by contacting said cell with an MCAM ligand (e.g., (i) MCAM, (ii) an MCAM binding partner, (iii) an MCAM-specific antibody, or (iv) an MCAM-binding fragment of any of (i) to (iii)) and identifying said inflammatory cytokine-secreting T cell precursor based on the binding to said MCAM ligand.

In another aspect, the present invention provides a method of purifying an inflammatory cytokine-secreting T cell or a precursor thereof from a cell sample, or enriching a sample comprising a cell sample in inflammatory cytokine-secreting T cells or a precursor thereof, said method comprising contacting said sample with an MCAM ligand (e.g., (i) MCAM, (ii) an MCAM binding partner, (iii) an MCAM-specific antibody, or (iv) an MCAM-binding fragment of any of (i) to (iii)) and isolating or purifying said inflammatory cytokine-secreting T cell or precursor thereof on the basis of its binding to the MCAM ligand.

In another aspect, the present invention provides a kit for identifying and/or purifying an inflammatory cytokine-secreting T cell or a precursor thereof from a cell sample, or enriching a sample comprising a cell sample in inflammatory cytokine-secreting T cell precursors, said kit comprising an MCAM ligand (e.g., (i) MCAM, (ii) an MCAM binding partner, (iii) an MCAM-specific antibody, or (iv) an MCAM-binding fragment of any of (i) to (iii)) and instructions for identifying and/or purifying the inflammatory cytokine-secreting T cell or a precursor thereof from the sample.

In an embodiment, the above-mentioned MCAM ligand is labeled (using a fluorescent moiety, for example).

In an embodiment, the above-mentioned MCAM ligand is an MCAM-specific antibody or MCAM-binding fragment thereof.

In an embodiment, the above-mentioned MCAM ligand is bound to a solid support, such a bead (e.g., a magnetic bead) such as to allow easy separation/isolating of the cell bound to the MCAM ligand from the other cells in the sample (using a column, for example), and thus to obtain a sample enriched in inflammatory cytokine-secreting T cells or a precursor thereof. IN an embodiment, the above-mentioned identifying and/or purifying is performed by flow cytometry (e.g., fluorescence-activated cell sorting, FACS), using an MCAM ligand (e.g., an antibody) conjugated to a label, including fluorescent labels commonly used in flow cytometry applications such as Fluorescein isothiocyanate (FITC), Allophycocyanin (APC), phycoerythrin (PE) and Alexa Fluor™ dyes.

In an embodiment, the above-mentioned inflammatory cytokine-secreting T cell precursor has the capacity to secrete preferentially: (i) IL-17, (ii) IFN-γ, (iii) TNF-α, (iv) GM-CSF, or (v) any combination of (i) to (iv), upon activation/stimulation, such as antigen-specific or non-antigen specific TCR-mediated stimulation.

In an embodiment, the above-mentioned inflammatory cytokine-secreting T cell or precursor thereof is a memory T cell. In another embodiment, the above-mentioned inflammatory cytokine-secreting T cell or precursor thereof is a $CD4^+$ T cell. In a further embodiment, the above-mentioned inflammatory cytokine-secreting T cell or precursor thereof is a $CD4^+$ T cell having the capacity to differentiate into an IL-17-secreting cell (typically referred to as a "Th17 cell").

The present invention is illustrated in further details by the following non-limiting examples.

EXAMPLE 1

Materials and Methods

Patients and sample collection. All MS patients were observed at the CHUM-Notre-Dame Hospital MS clinic and diagnosed according to the McDonald criteria. Human peripheral blood (PB) was collected from MS patients and from healthy donors. PB mononuclear cells were obtained from heparinized whole blood using Ficoll™ density gradient separation (Amersham Biosciences, Baie D'Urfé, Quebec, Canada). $CD14^+$ monocytes, $CD4^+$ $CD45RO^+$ lymphocytes and $MCAM^+$ T cells were isolated using the magnetic cell sorting (MACS™) isolation columns, according to manufacturer's protocol (Miltenyi, Auburn, Calif.).

BBB-endothelial cell isolation and culture. BBB-endothelial cells were isolated from non-epileptic material according to a previously published protocol ((Prat et al., *J Neuropathol Exp Neurol.* 2000 59(10):896-906; Biernacki et al., *J Neuropathol Exp Neurol.* 2001 60(12): 1127-36; Prat et al., *Arch Neurol.* 2002 59(3): 391-7; Kebir et al. *Nat Med.* 2007 13(10): 1173-5. Epub 2007 Sep. 9; Cayrol et al. *Nat Immunol.* 2008 9(2):137-45. Epub 2007 Dec. 23; Ifergan et al. *Brain.* 2008 131(Pt 3): 785-99. Epub 2007 Dec. 20). BBB-endothelial cells were grown in primary cultures in media composed of Medium 199 (Gibco® Invitrogen, Burlington, ON, Canada) supplemented with 20% clone M3 conditioned media, 10% fetal bovine serum (FBS), 5% normal human serum (HS), 0.2% endothelial cell growth supplement (ECGS) (5 µg/ml) and 0.13% insulin-selenium-transferrin premix on 0.5% gelatin-coated tissue culture plastic plates (all reagents from Sigma, Oakville, ON, Canada). For treatments, the BBB-endothelial cells were grown in culture media in the presence of 40% astrocyte conditioned media (ACM), until they reach confluency. When indicated BBB-endothelial cells were activated for 16 hours with 100 U/ml of Tumor Necrosis Factor (TNF) and 100 U/ml of Interferon (IFN)-γ (Biosource-Invitrogen, Carlsbad, Calif., USA) in the presence of 40% ACM and the absence of ECGS. As previously demonstrated, these cells express factor VIII, von Willebrand factor, Ulex Agglutenens Europaensis-1-binding sites, endothelial antigen HT-7; and are susceptible to tumor necrosis factor (TNF)-induced CD54 and CD106 up-regulation. Immunoreactivity for glial fibrillary acidic protein and α-myosin could not be detected, confirming the absence of contaminating astrocytes and smooth muscle cells, respectively. The absence of monocytes and macrophages was confirmed by immunostaining with anti-CD14 and anti-CD11c antibodies.

Western blot analysis of MCAM expression in whole cell lysates and lipid rafts of BBB-ECs. Specific protein detection was performed by Western blot. Forty µg of BBB-EC proteins were analyzed by standard SDS-PAGE using anti-MCAM antibody (mouse, 1/100 ebioscience). Lipid raft were isolated from confluent BBB-ECs using a previously published protocol (Wosik et al. 2008). Cholesterol, phospholipid and protein concentrations in each fraction were assayed using commercially available kits: Cholesterol assay kit (Molecular Probes), Phospholipids B colorimetric method kit (Wako) and BCA Protein assay kit (Pierce). Lipid raft markers were assessed by SDS-PAGE (GM1, horse radish peroxidase (HRP)-cholera toxin B subunit, Molecular Probes; goat anti-CD59, 1/200, R&D Systems). Specific binding was revealed with HRP-conjugated anti-mouse and anti-goat antibody using the ECL system and anti-actin was used as a loading control.

Immunostaining analysis of MCAM expression on CNS vessel. Formaldehyde-fixed CNS specimens from five MS-affected individuals were examined, (2 males, both 42 years of age and 3 females, 54, 62 and 66 years of age); evolution of disease was between 2 and 20 years. Five control brains from patients who died of non-neurological traumatic injury (34, 46, 51, 69 years of age and unknown, 3 males and 2 females) were used as controls. Autopsies were performed within 6-12 h from time of death. Active MS lesions were identified by LFB and haematoxilin and eosin (H&E) staining and defined as areas of demyelination associated with intense perivascular immune cell infiltration (48.2±3 nuclei/field centered on a vessel). Normal appearing white matter (NAWM) from MS cases and control brains (non-neurological traumatic death) were defined as areas of normal myelin staining in the absence of immune cell infiltration (21.6±4 nuclei/vessel and 23.2±5 nuclei/vessel, respectively). For immunohistofluorescence, 5 μm thick sections were deparaffinized and stained with antibodies specific for MCAM (mouse monoclonal, 1/50, ebioscience), Cav-1 (polyclonal rabbit, 1/75, Santa Cruz Biotechnology), or a with donkey anti mouse-specific antibody (1:400, biotin-conjugated, followed by streptavidin-FITC; Dako and Jackson ImmunoResearch Laboratories, respectively) or a Cy3-conjugated goat rabbit-specific antibody (1:400, 30 min; Jackson ImmunoResearch). Nuclei were stained with TOPRO-3 (1:300 in PBS; Molecular Probes). Control staining was performed with an isotype control antibody. For immunocytochemistry human BBB-ECs were treated, or not, with IFN-γ and TNF (100 U/ml) for 16 h. Isolated peripheral blood CD4+ T lymphocytes were stained with CFSE (green) and allowed to migrated for 2 h and then fixed with 4% paraformaldehyde. MCAM was detected with anti-MCAM (mouse monoclonal, 1/50, ebioscience) followed by a goat anti-mouse antibody conjugated to FITC (green, 1:400, biotin-conjugated, Dako. All images were acquired using a Leica SP5 confocal microscope and analyzed using the Leica™ LAS AF software (Leica Wetzlar).

Immunostaining analysis of MCAM expression in brains. Frozen sections from two different MS brains. For both human and mouse MCAM, a rabbit monoclonal antibody (EPR3208 Abcam) at 1:200 followed by a goat anti-rabbit RRX at 1:750 were used. To detect human IL-17, a mouse antibody (R&D systems) at 1:50 followed by a goat anti-mouse Alexa488 at 1:400 were used. For mouse IL-17, a rat antibody-Alexa647 (eBioscience) at 1:5 was used. Nuclei were stained with TOPRO-3 (1:300 in PBS; Molecular Probes). Control staining was performed with an isotype control antibody. All images were acquired using a Leica SP5 confocal microscope and analyzed using the Leica™ LAS AF software (Leica Wetzlar).

MCAM expression in peripheral blood and cerebro-spinal fluid samples. Venous blood samples were obtained from consenting healthy donors and MS patients. PB mononuclear cells were obtained from heparinized whole blood using Ficoll™ density gradient separation (Amersham Biosciences, Baie D'Urfé, Quebec, Canada). Mononuclear cells were assessed by flow cytometry using anti-CD14-FITC (fluorescein isothiocyanate), anti-CD8-R-PE (R-Phycoerythrin), anti-CD19-PE-Cy5 and anti CD4-pacific blue and other cell specific markers (all antibodies from BD PharMingen). All cell staining were acquired on a BD LSR™ II (Becton Dickinson) and analyzed using the BD FACSDiva™ software (BD Bioscience).

EAE mice. Six to eight week-old female wild-type C57BL/6 mice were purchased from Charles River Laboratories (Montréal, Qc, Canada). Experimental autoimmune encephalomyelitis (EAE) was induced by active immunization in female C57BL/6 mice (Jackson Laboratory, Bar Habor, Me., USA). Seven to eight week old mice were injected subcutaneously with 200 μg of myelin oligodendrocytes glycoprotein $(MOG)_{35-55}$ peptide [Sequence: MEVG-WYRSPFSRVVHLYRNGK (SEQ ID NO: 3)] emulsified in complete Freund's Adjuvant supplemented with 600 μg of *Mycobacterium tuberculosis* H37RA (DIFCO Laboratories, Detroit, Mich., USA). On day 0 and 2, mice were injected intraperitoneally with 500 ng of Pertussis toxin (List Biological Laboratories, Inc., Campbell, Calif., USA).

T cell stimulation. CD14+ monocytes, CD4+ CD45RO+ lymphocytes and MCAM+ T cells were isolated from PB mononuclear cells using the magnetic cell sorting (MACS™) isolation columns, according to manufacturer's protocol (Miltenyi, Auburn, Calif.). Isolated CD4 T cells (one million cells/nil) were cultured with autologous $CD14_+$ monocytes (0.5 million/ml). CD4+ lymphocytes were labeled with the vital dye 5,6-carboxyfluorescein diacetate succinimidyl ester as required (CFSE), were cultured for 5 days in the presence of autologous CD14+ monocytes, anti-CD3 (OKT3, 2.5 μg/ml) and either IL-2 (20 units/nil) or IL-23 (10 ng/ml) in the presence of anti-IFN-gamma (clone K3.53) and anti-IL-4 (clone 3007, both at 5 μg/ml) in RPMI 1640 supplemented with 5% human serum, 2 mM L-glutamine, 100 U/ml penicillin and 100 μg/mL streptomycin (Sigma). After 5 days, the proliferation of the CD4+ T lymphocyte, the presence of the different activation marker (CD45RO, CD161, CD25, CD69, CD107a, etc.) and the capacity to produce cytokines (IFN-γ, IL-17, GM-CSF, IL-4, TNF, etc.) were assessed by flow cytometry. All cell staining were acquired on a BD LSR™ II (Becton Dickinson) and analyzed using the BD FACSDiva™ software (BD Bioscience).

Intracellular cytokine staining. For intracellular cytokine staining, CD4+ lymphocyte and the corresponding APC co-cultures were activated for 18 h with 1 μg/mL ionomycin and 20 ng/mL phorbol 12-myristate 13-acetate (PMA) in the presence of 2 μg/mL brefeldin A (Sigma) for the last 6 h of co-culture. Recombinant cytokines and antibodies were purchased from R&D Systems. Cells were stained for surface markers and were then fixed and permeabilized in 4% (w/v) paraformaldehyde with 0.1% (w/v) saponin in Hank's Balanced Salt Solution for 10 minutes at room temperature. Intracellular staining was performed by incubating cells with antibodies against cytokines (eBioscience, San Diego, Calif.) (1 mg/mL) for 30 m on ice in PBS buffer containing 0.1% (w/v) saponin, 1% FBS, 0.1% (w/v) $NaN_3$, followed by two washes and resuspended in staining buffer (1% (v/v) FBS, 0.1% (w/v) $NaN_3$ in PBS). All cell staining were acquired on a BD LSR™ II (Becton Dickinson) and analyzed using the BD FACSDiva™ software (BD Bioscience).

Quantitative Real-time PCR. Total RNA was extracted using RNeasy™ Mini kit according to the manufacturer's instruction (Qiagen). RNA samples were transcribed into cDNA using Quantitect™ Reverse Transcription kit according to the manufacturer's instruction (Qiagen). Relative gene expression levels were determined using primers and TaqMan™ FAM-labeled MGB probes for IL-17, IFN-γ, IL-23R, T-bet, GATA-3 and RORg and ribosomal 18S (VIC-labeled probe) (Applied Biosystems respective product number: Hs00174383_m1, Hs00989291_m1, Hs00332759_m1, Hs00203436_m1, Hs00231122_m1 and Hs01076112_m1) and according to the manufacturer's instruction. qPCR cycling was performed according to the default temperature settings (2 min at 50° C., 10 min at 95° C., followed by 40 cycles of 15 s at 95° C., 1 min at 60° C.) in a 7900HT Fast-Real-Time™ PCR System (Applied Biosystems). Gene-specific mRNA was normalized compared to endogenous control (18S) and relative expression quantified by extrapolating from an internal control using cDNA from cells having high expression levels.

Intracellular calcium. CD4$^+$CD45RO$^+$ were isolated from the peripheral blood of healthy volunteers (n=1 for each condition). Lymphocytes were cultured for 6 days in the presence of autologous CD14$_+$, IL-23, anti-IL-4, anti-IFN-$\gamma$, OKT3 in ex vivo medium without serum. At day 6, T cells were harvested, washed, incubated with eFluor™514 calcium sensor dye (1.25 µM) in charging medium (RPMI$_+$HEPES 10 mM$_+$FBS 2%$_+$Pluronic 0.04%) for 30 minutes at 37° C., washed, incubated with the specified stimuli (IgG1, P1H12 or anti-CD28) at a final concentration of 20 µg/ml, or OKT3 at a final concentration of 1 µg/ml) at 4° C. for 30 minutes, washed and then resuspended in acquisition medium (HBSS$_+$HEPES 10 mM$_+$FBS 1%) at 4° C. with or without extracellular 2 mM Ca$^{2+}$ and 1 mM Mg$^{2+}$. Cells were equilibrated at 37° C. for 180 seconds prior to flow cytometry analysis. After basal level determination (2 minutes), cross-linking was performed using goat anti-mouse IgG at 25 µg/ml. Intracellular calcium concentration ([Ca2$_+$]$_i$) was measured and calculated as delta geometric mean of MFI.

Statistical analysis. Statistical analyses were performed using PRISM 4 Graphpad™ Software (San Diego, Calif.) and data are presented as the mean±the standard error of the mean (SEM). One-way analysis of variance (ANOVA) was performed followed by Bonferroni multiple comparison post-test for all experiments except for the migration across the BBB, which was done using two-way ANOVA. Only p values <0.05 were considered significant. The data reported are either from either one representative experiment out of 3 independent experiments or pooled from 3 to 10 experiments. Statistical comparison of IL-17 and IFN-$\gamma$ staining was done using non-parametric student T-test. Differences between groups were considered significant when p<0.05.

EXAMPLE 2

Expression of MCAM in Human BBB-Endothelial Cells and Blood Cells

Figure 1C:
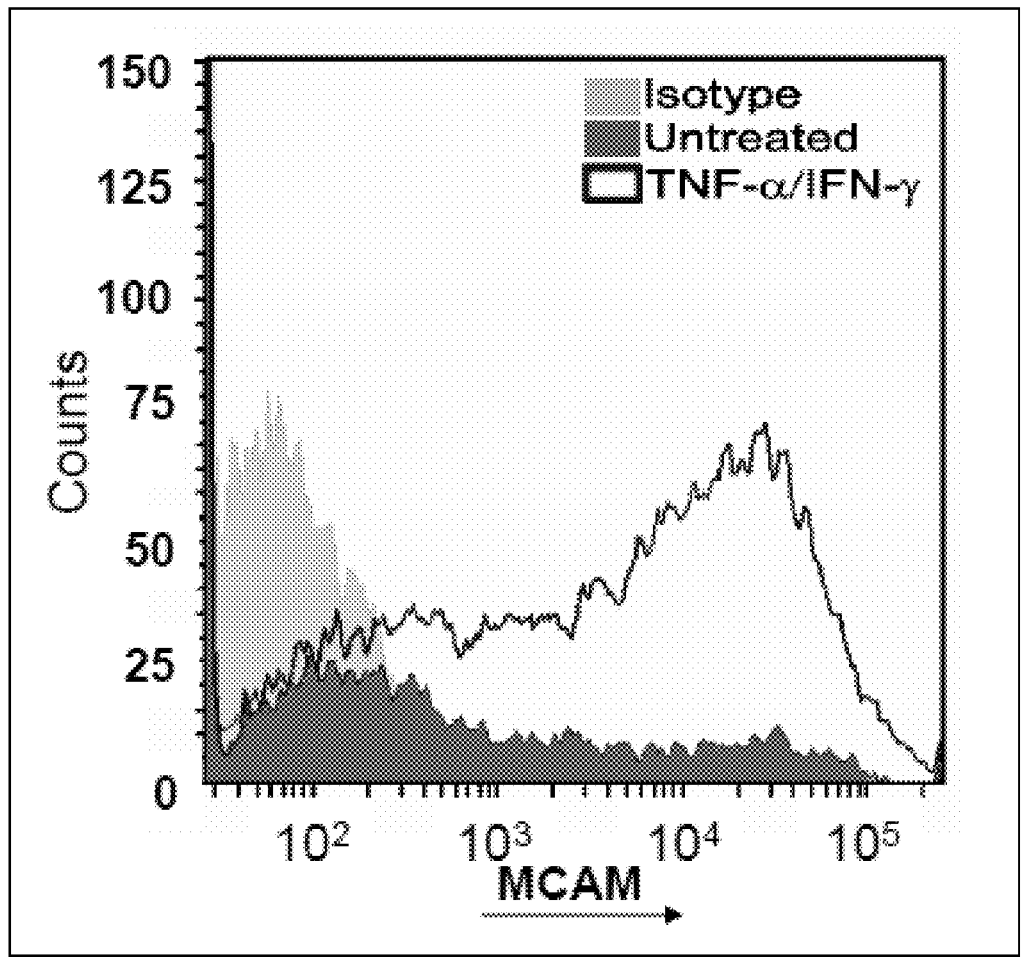
Figure 2A:
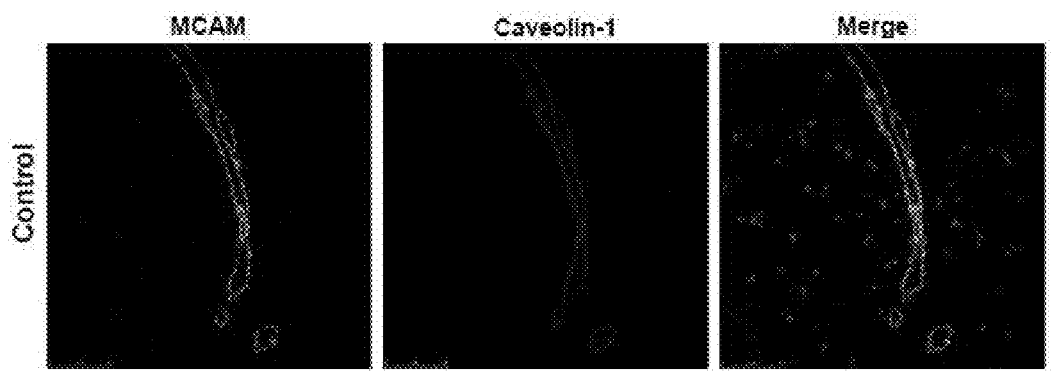
FIGS. 2A and B show the expression of MCAM in MS lesions. Paraffin-embedded material from control human CNS (top panels, FIG. 2A) and human active MS lesions (bottom panels, FIG. 2B) are shown. Immunostaining for Caveolin-1 (Cav-1, endothelial cell marker, middle panels) and MCAM (left panels) were acquired by fluorescent microscopy. Data shown are representative of 5 active MS lesions from 4 distinct MS-affected donors and 4 controls. Merged images are presented on the right panels and demonstrate co-localization of MCAM with Cav-1 on infiltrated blood vessels in MS and control tissue. Scale bar is 75 μm and nuclei were stained with TOPRO-3. These results indicate that MCAM is expressed by BBB-ECs in MS lesions and in control CNS tissue. The expression of MCAM does not seem to be significantly modulated in MS lesions.
Figure 2B:
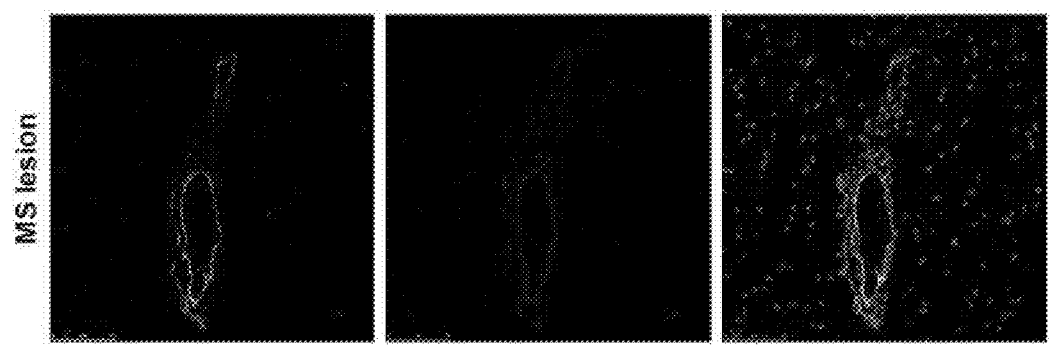
Figure 3:
FIG. 3 shows immunocytofluorescent staining of the expression of MCAM during leukocyte migration. Ex vivo CD4+ T lymphocytes isolated from healthy donors were labeled with carboxyfluorescein succinimidyl ester (CFSE) and then allowed to migrate across a monolayer of BBB-ECs for 2 hours. The monolayer was then washed extensively with PBS to remove non adherent cells and fixed with 4% paraformaldehyde. Cells were stained with anti-MCAM antibody. Scale bar is 25 μm. MCAM enrichment is seen surrounding the lymphocytes at points of EC contact and entry in a structure reminiscent of the transmigratory cup.
Figure 4A:
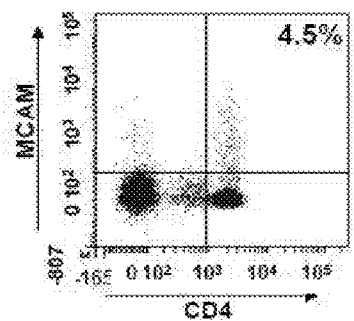
Figure 4B:
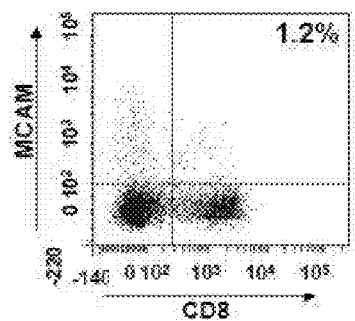
Figure 4C:
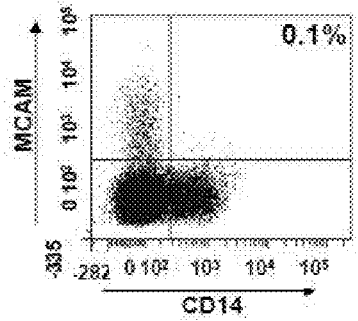
Figure 4D:
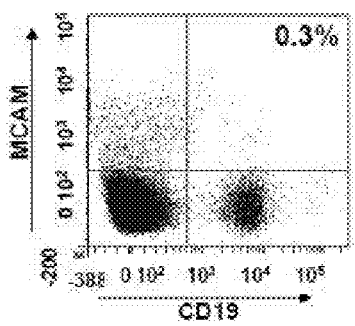
Figure 4E:
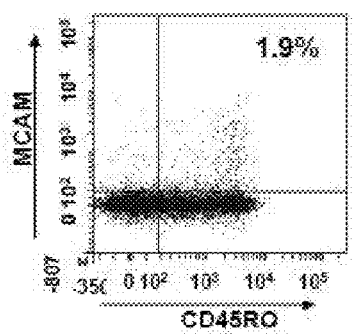
Figure 4F:
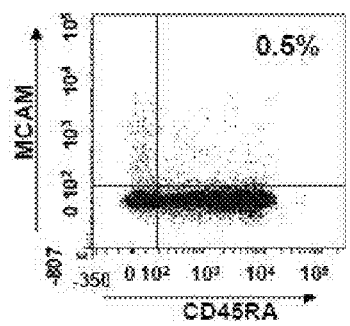
Figure 5A:
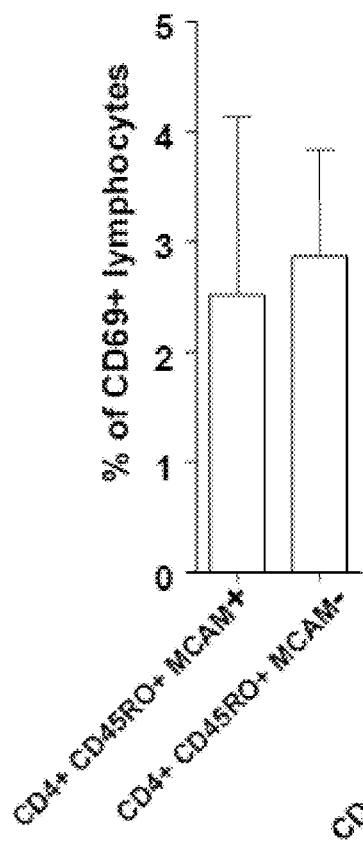
FIGS. 5A-E show a representative quantification of selected lymphocyte markers as assessed by flow cytometry on ex vivo MCAM+ human peripheral blood lymphocytes obtained from healthy donors. Quantification is shown for CD69 early activation marker (FIG. 5A), CD107a degranulation marker (FIG. 5B), the chemokine receptors CCR7 (FIG. 5C) and CCR6 (FIG. 5D) and the inflammatory cytokine IL-17 (FIG. 5E). Cells were labeled with anti-MCAM antibody concurrently with cell specific marker (n>4). * $p<0.05$,  $p<0.01$, * $p<0.001$. The data demonstrates that MCAM+ cells more frequently express CD161, CCR6 and IL-17, and express lower levels of CCR7.
Figure 5B:
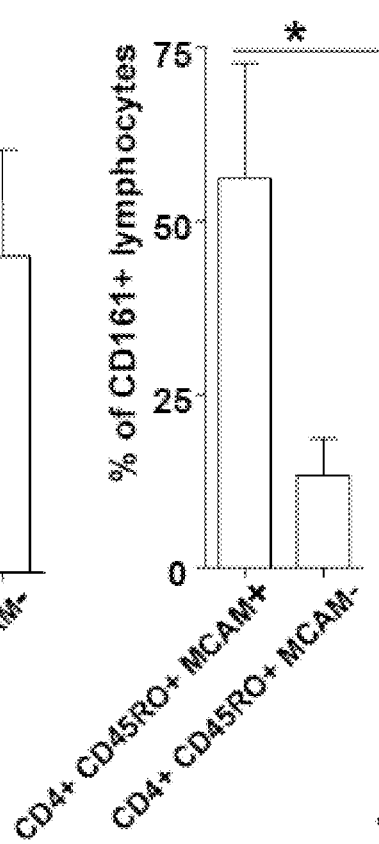
Figure 5C:
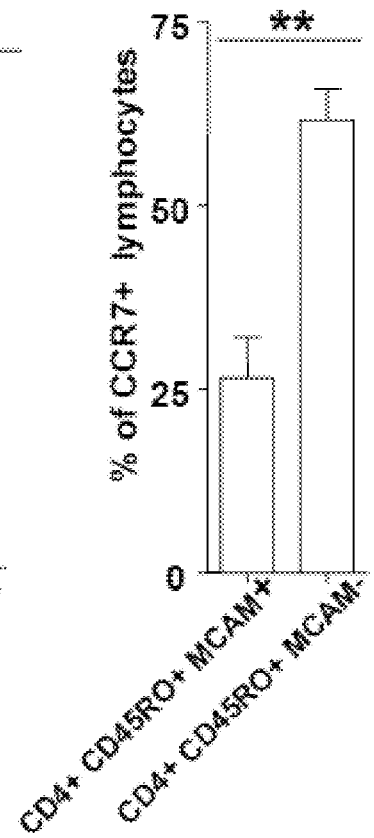
Figure 5D:
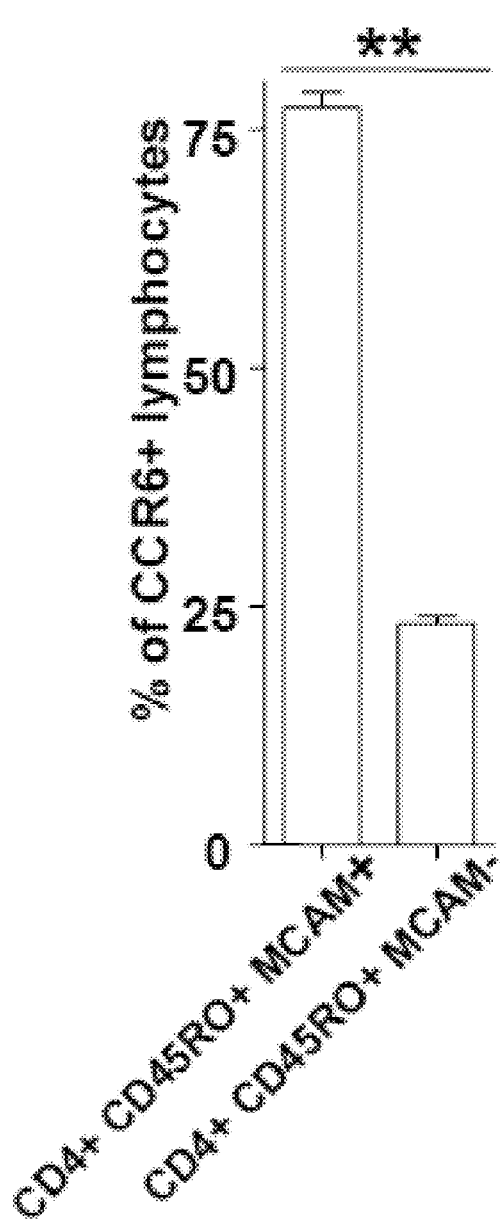
Figure 5E:
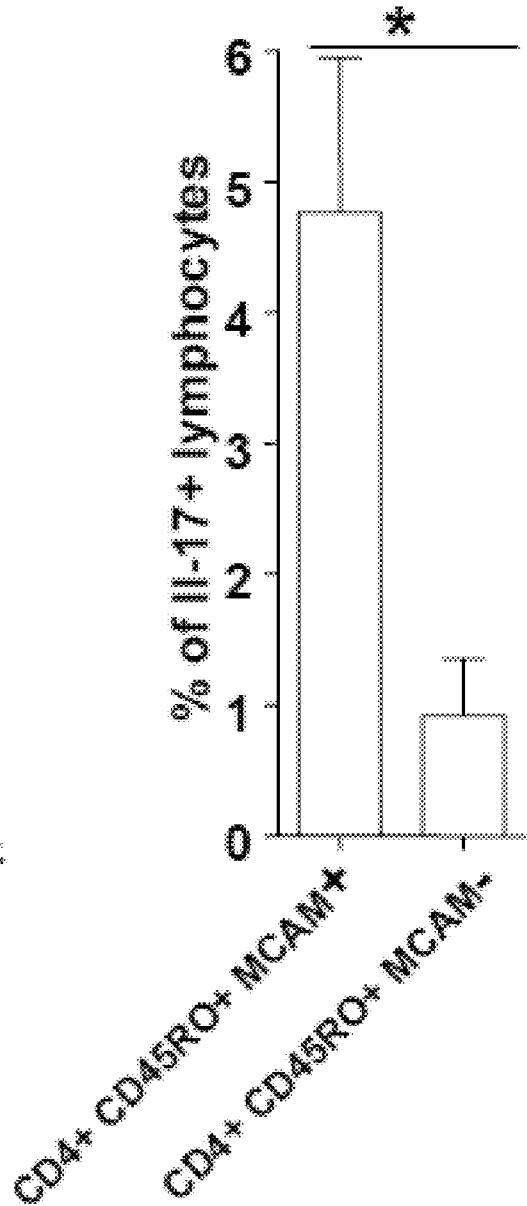
Figure 6E:
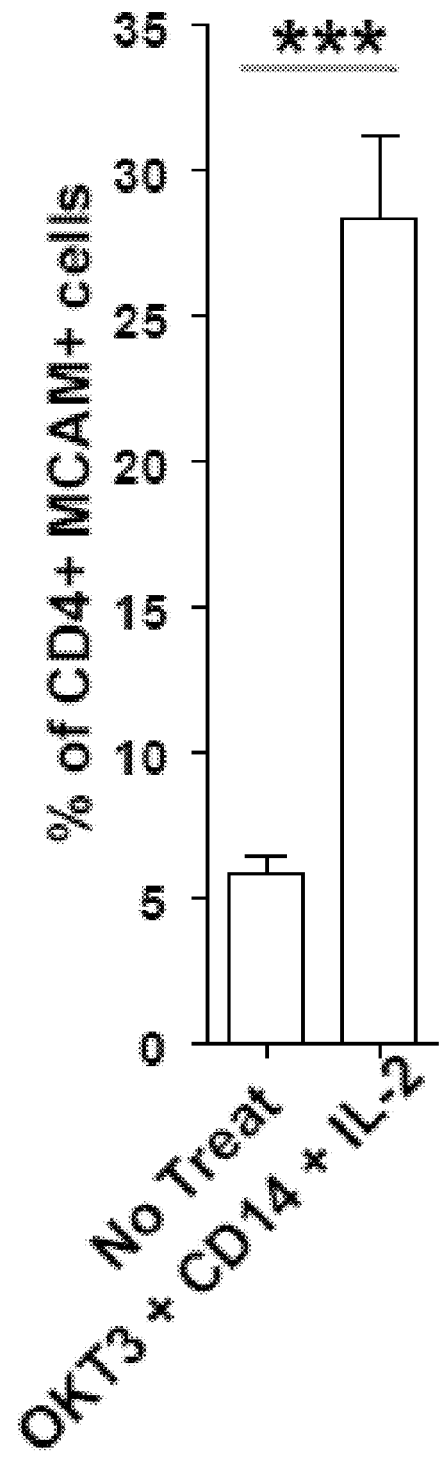
Figure 9C:
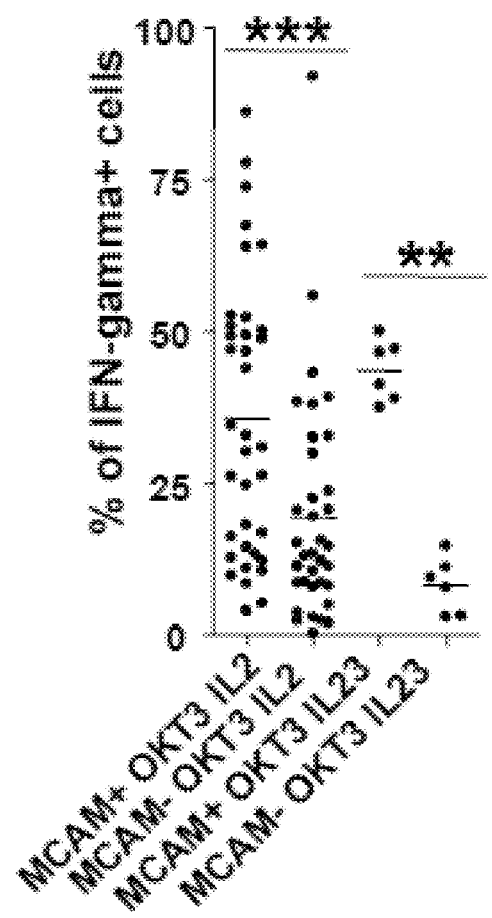
Figure 9D:
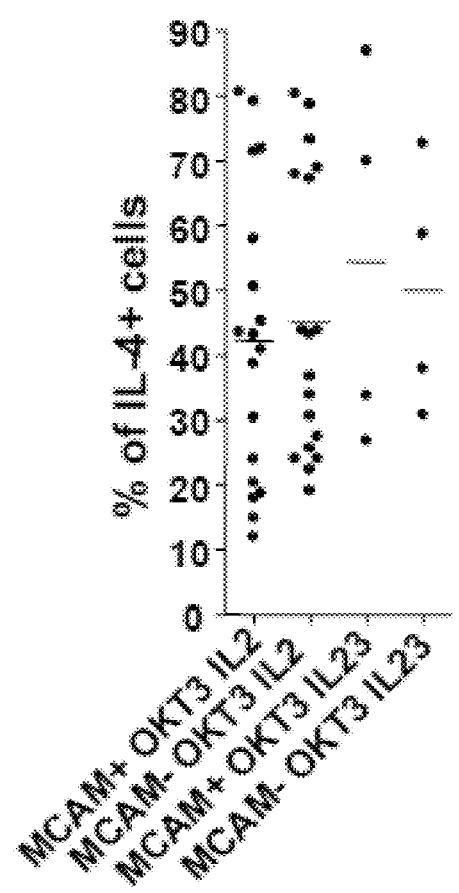

The expression of MCAM (melanoma cell adhesion molecule/CD146) on BBB-ECs was studied in vitro and in situ. MCAM is expressed by BBB-ECs in vitro (primary cultures of human BBB-ECs) and in situ (in control and MS patient archival autopsy central nervous system samples) (FIGS. 1A-B and 2A-B). In vitro MCAM expression was shown to be up-regulated with inflammatory cytokine treatment (TNF-$\alpha$ and IFN-$\gamma$, 100 U/ml for 16 hours), as shown in FIG. 1C. In situ expression of MCAM on CNS vessels is strong and did not vary significantly between control vessels, MS normal appearing white matter, and active MS lesions (FIGS. 2A and B). Using BBB-ECs in culture as a monolayer with isolated human lymphocytes from the peripheral blood (PB) of healthy controls, it was shown that adherent lymphocytes are surrounded by a MCAM$^+$ ring-like structure that is reminiscent of a transmigratory cup, a structure involved in leukocyte diapedesis across vascular beds (FIG. 3).

EXAMPLE 3

Expression of MCAM on Human T Lymphocytes

The expression of MCAM on human peripheral blood immune cells was assessed (FIG. 4A-F). A sub-group of human peripheral blood CD4$^+$ and CD8$^+$ T lymphocytes express MCAM. The different leukocyte markers that were associated with the MCAM$^+$ lymphocytes was assessed and it was demonstrated that MCAM$^+$ lymphocytes express certain markers (CD2, CD3, CD6, CD45RO, CD161, CCR6 and CD28, for example) and were less associated, if they express at all, with other markers (CD45RA, CCD56, CD62L, and CCR7, for example) (FIG. 4A-F). These studies demonstrate MCAM$^+$ is expressed by T lymphocytes having a memory phenotype. These cells express very little cytokines ex vivo (as assessed by intracellular FACS staining), comparable to MCAM$^-$ T lymphocytes of the human peripheral blood.

EXAMPLE 4

Functional Characterization of MCAM$^+$ Lymphocytes

The function of MCAM$^+$ lymphocytes was studied using different activation regimen and looking at different activation markers (proliferation, CD161, CD107a, CD69) and by studying the cytokine profile associated with activated MCAM$^+$ lymphocytes compared to MCAM$^-$ lymphocytes. A polyclonal non-antigen specific TCR-mediated activation strategy was used (anti-CD3, autologous CD14$^+$ cells, in presence of either IL-2 or IL-23) on whole peripheral blood mononuclear cells or on isolated leukocytes. As shown in FIGS. 5A-D, 6A-B, 7A-D, 8A-B, 9A-D and 10, activated MCAM lymphocytes preferentially express certain markers and certain cytokines. CD4$^+$ MCAM$^+$ lymphocytes behave similarly to MCAM$^-$ memory lymphocytes concerning lymphocyte proliferation and certain activation markers (such as CD25). In contrast, CD4$^+$ MCAM$^+$ lymphocytes are significantly associated with CD161, CD107a and CD69. Furthermore CD4$^+$ MCAM$^+$ lymphocytes express significantly higher levels of the cytokines IL-17, IFN-$\gamma$, GM-CSF and TNF, as compared to memory CD4$^+$ MCAM$^-$ lymphocytes from the same donors. The expression of MCAM by human Th17 cells (human CD4$^+$ T cells activated under conditions that favor the production of IL-17) was further shown by a proteomic screen that demonstrated that human Th17 cells express the protein MCAM. The association of MCAM on lymphocytes and the secretion of the cytokine IL-17 following T cell activation is the strongest and indicates that MCAM may be used as a marker of lymphocytes that have the potential to secrete IL-17 following re-activation.

Figure 11A:
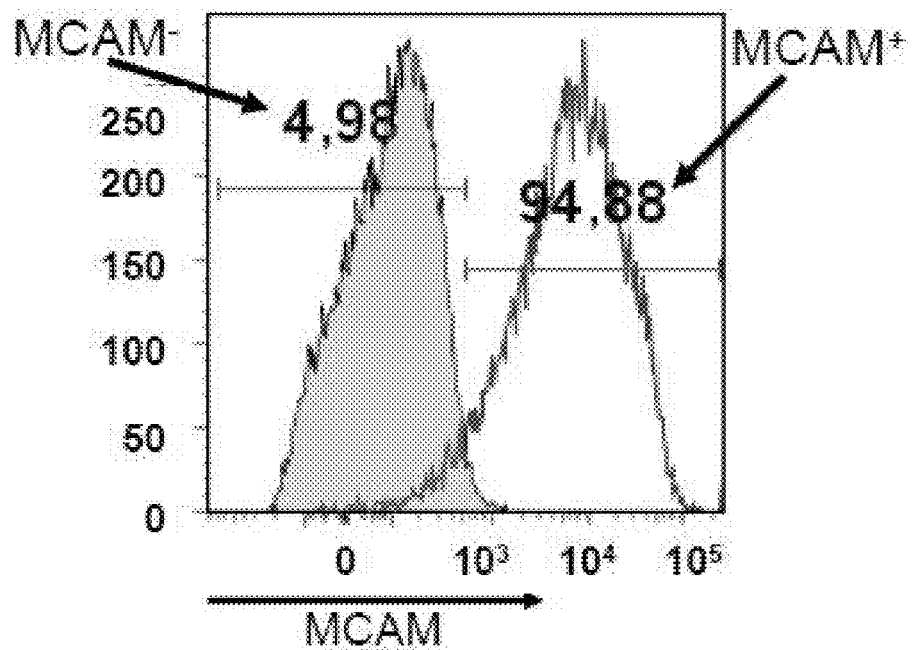
FIGS. 11A and B show MCAM expression on $MCAM^+$-sorted lymphocytes after 5 days in culture in a Th17 polarization environment. Memory T cells expressing CD45RO, CD4 and MCAM were sorted with a purity of >99% and cultured for 5 days in presence of IL-23, anti-CD3, anti-IL-4 and anti-IFN-γ (Th17 polarization conditions).
Figure 11B:
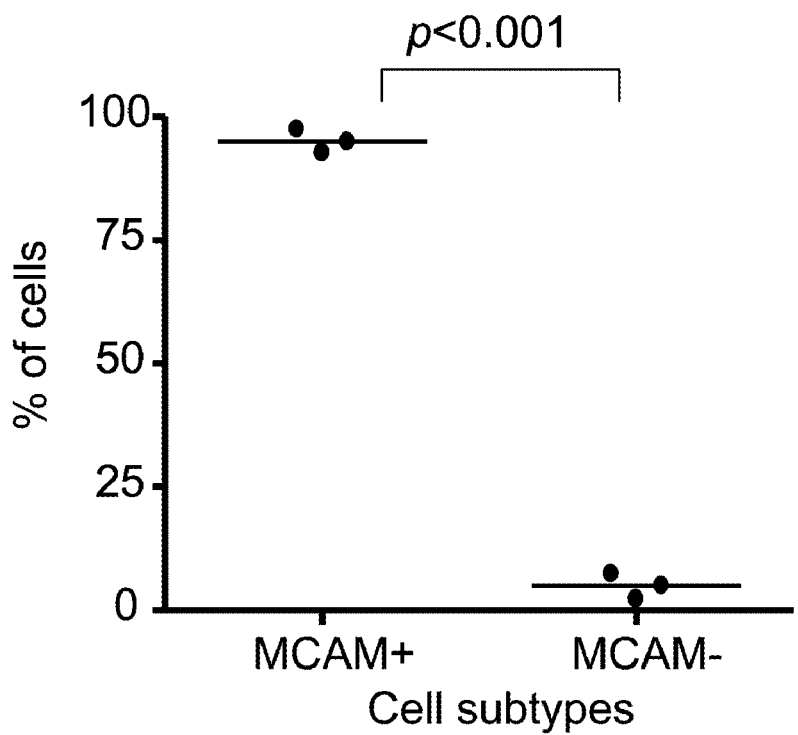
FIG. 11B: Quantification of the proportion of cells that are $MCAM^+$ or $MCAM^-$ after 5 days in Th17 polarization conditions and originate from memory T cells expressing CD45RO and CD4 sorted for MCAM expression ($MCAM^+$ fraction). n=3. Statistical analysis were obtained with Paired T test.
Figure 12A:
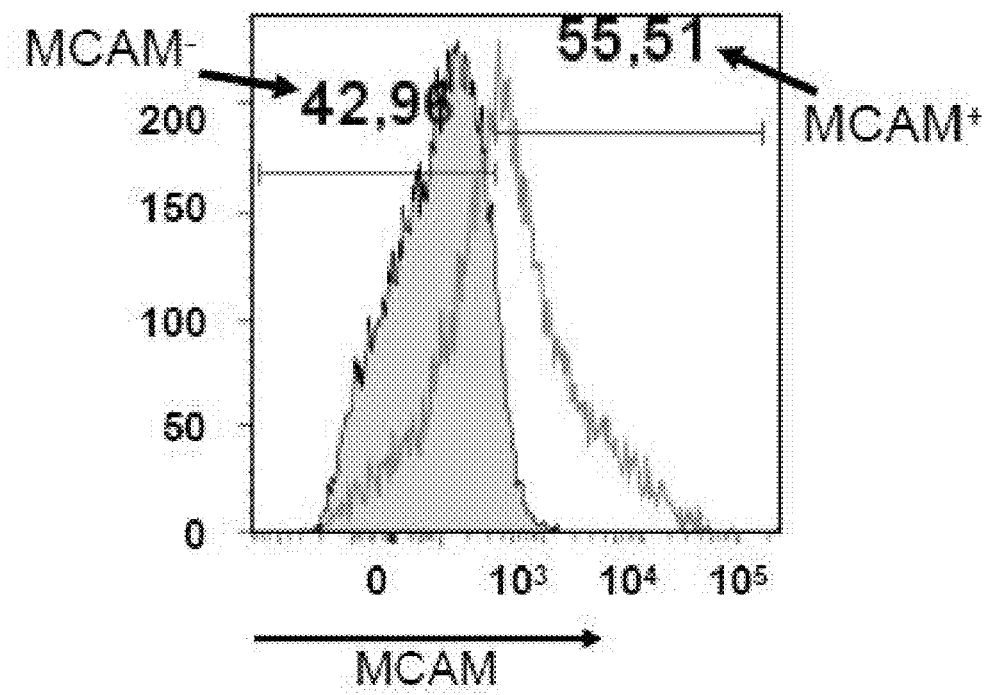
FIGS. 12A and B show MCAM expression on MCAM-negative-sorted lymphocytes after 5 days in culture in Th17 polarization environment. Memory T cells expressing CD45RO and CD4, but negative for MCAM were sorted with a purity of >99% and cultured for 5 days in presence of IL-23, anti-CD3, anti-IL-4 and anti-IFN-γ (Th17 polarization conditions). (A) Representative histogram showing expression of MCAM expression in memory T cells expressing CD45RO and CD4 (grey line) compared with isotype (solid grey) after 5 days in culture. (B) Quantification of the proportion of cells that are $MCAM^+$ or $MCAM^-$ after 5 days in Th17 polarization conditions and originate from memory T cells expressing CD45RO and CD4 negatively sorted for MCAM expression ($MCAM^-$ fraction) (n=3). Statistical analysis were obtained with Paired T test, ns=not significant.
Figure 12B:
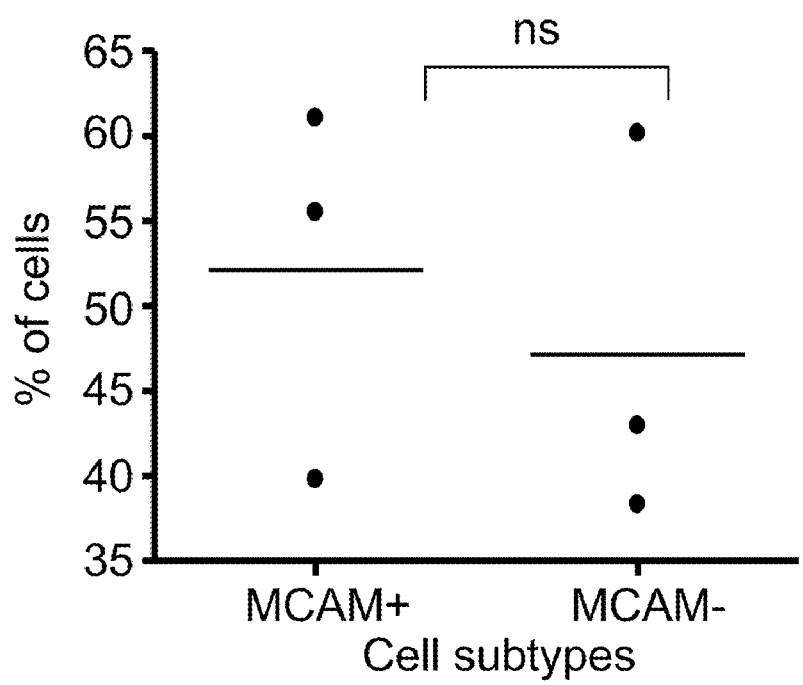
Figure 13A:
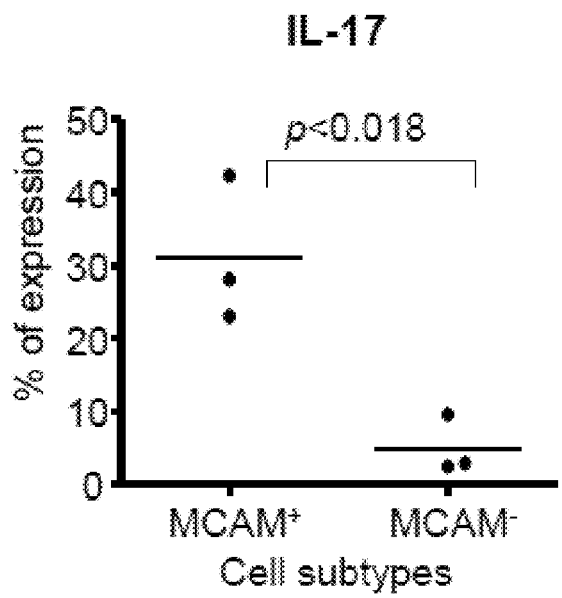
FIGS. 13A-C show the expression of IL-17 (FIG. 13A), IFN-γ (FIG. 13B) and IFN-γ and IL-17 (FIG. 13C) in $MCAM^+$ memory T cells originating from $MCAM^+$ sorted lymphocytes. Memory T cells expressing CD45RO, CD4 and MCAM were sorted with a purity of >99% and cultured for 5 days in presence of IL-23, anti-CD3, anti-IL-4 and anti-IFN-γ (Th17 polarization conditions). Intracellular stainings for IL-17 (FIG. 13A), IFN-γ (FIG. 13B) and IL-17+IFN-γ (FIG. 13C) were performed on cultured $CD45RO^+$ $CD4^+$ $MCAM^+$ cells and $CD45RO^+$ $CD4^+$ $MCAM^-$ cells stimulated with PMA/ionomycin/Brefeldin A for 4 hours (n=3). Statistical analysis were obtained with Paired T test, ns=not significant.
Figure 13B:
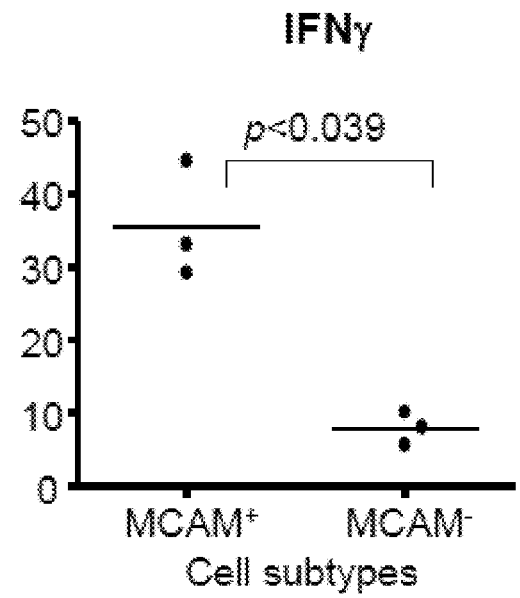
Figure 13C:
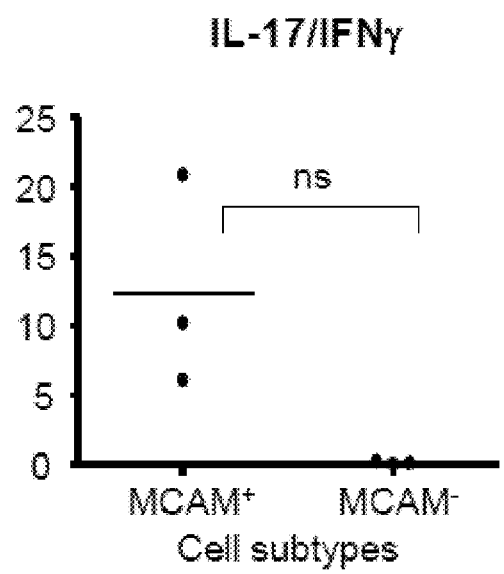

The results presented at FIGS. 11A and B show that the expression of MCAM is maintained on MCAM positive sorted lymphocytes after 5 days in culture in a Th17 polarization environment (more than 90% of the cells remains MCAM positive after 5 days). Also, a significant proportion of MCAM-negative sorted cells expresses MCAM after 5 days of in vitro culture under Th17 polarization conditions (FIGS. 12A and B), demonstrating that MCAM is a marker of Th17 differentiated T cells. The results depicted in FIG. 13 show that MCAM$^+$ cells derived from MCAM$^+$ sorted lymphocytes and cultured for 5 days in Th17 polarization conditions express IL-17 and IFN-$\gamma$ in a higher proportion as compared to MCAM⁻ cells. Similarly, MCAM⁺ cells derived from MCAM negative sorted lymphocytes and cultured for 5 days in Th17 polarization conditions express IL-17 and IL-8 in a higher proportion as compared to MCAM⁻ cells (FIG. 14, left panel and FIG. 15). A higher proportion of MCAM⁺ derived from MCAM negative sorted cells appear to express IFN-γ (FIG. 14, middle panel) and both IL-17 and IFN-γ (FIG. 24, right panel), although it did not reach statistical significance.

EXAMPLE 5

Expression of MCAM on Samples from MS Patients

Figures 16A, 16B:
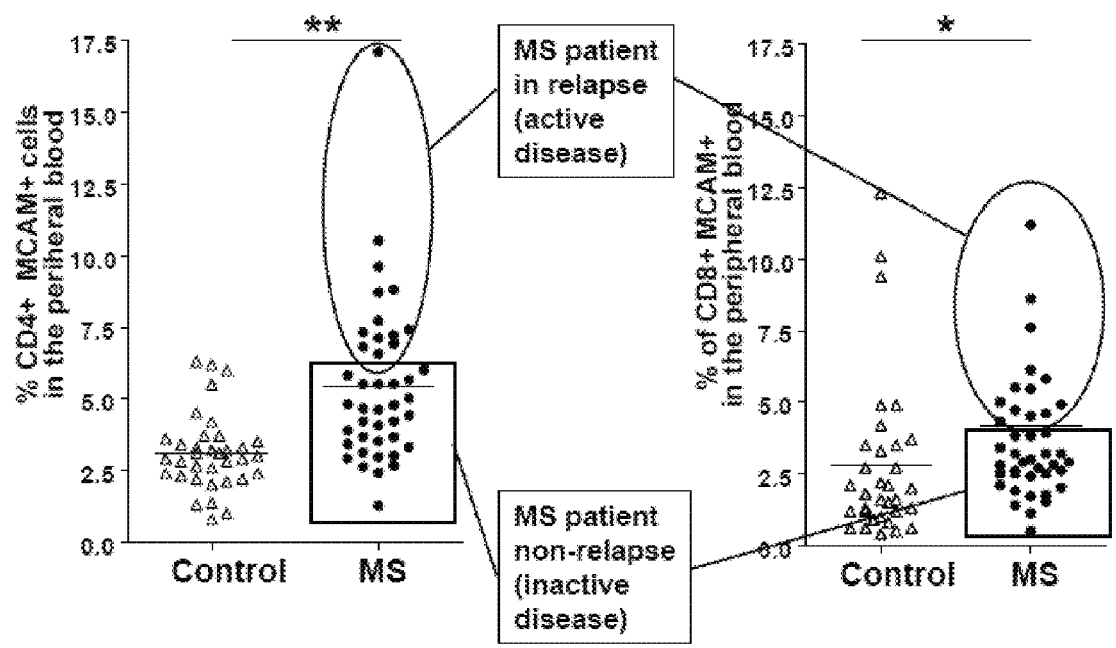
FIGS. 16A-C show the expression of MCAM on $CD4^+$ and $CD8^+$ T lymphocytes obtained from healthy donors (controls) and MS patients. Human ex vivo peripheral blood collected from healthy donors and MS patients was directly subjected to whole blood FACS staining with anti-CD3, anti-CD4, anti-CD8, anti-MCAM antibodies. FACS acquisition was performed the same day.
Figure 16C:
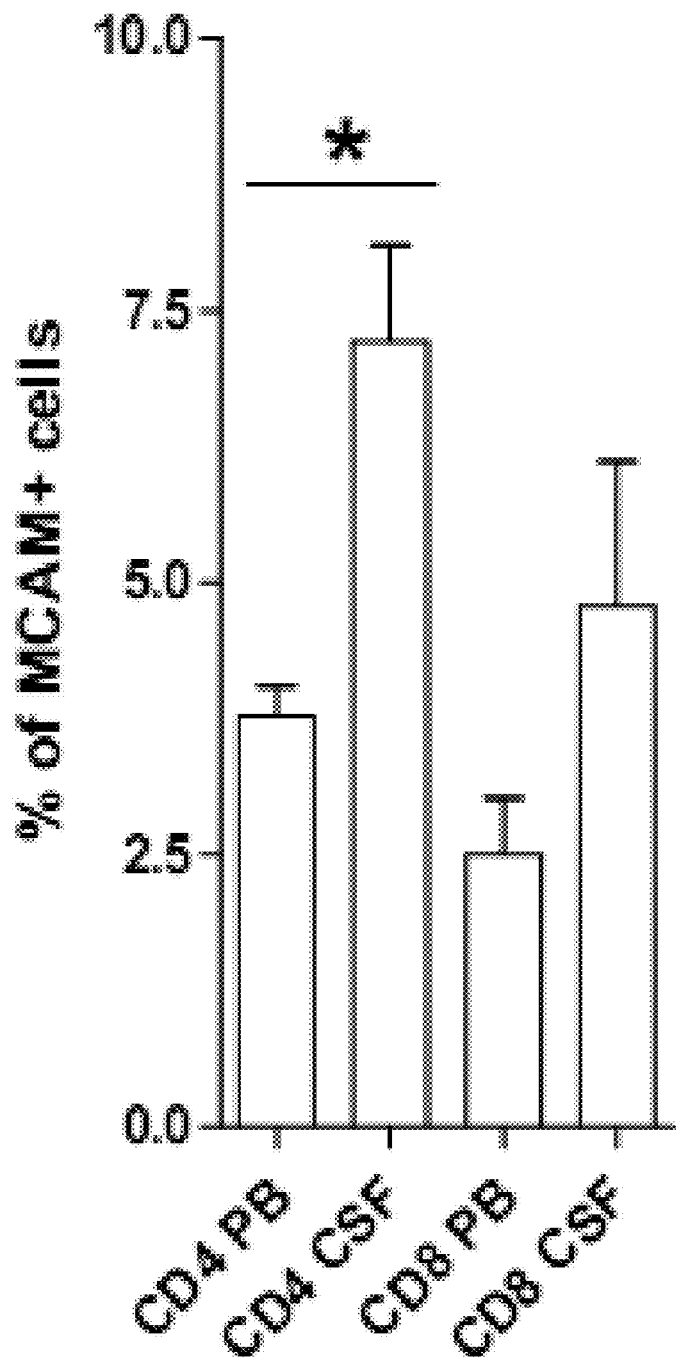

The proportion of MCAM⁺ lymphocytes in the peripheral blood of MS patients in relapse was determined and compared to that of healthy donor peripheral blood. As shown in FIGS. 16A and 16B, the peripheral blood of MS patients contains a significantly higher proportion of CD4⁺ and CD8⁺ T lymphocytes that express MCAM, as compared to healthy controls. FIG. 16C shows that MCAM⁺ lymphocytes (both CD4 and CD8) are enriched in the cerebro-spinal fluid (CSF) of MS patients, as compared to the peripheral blood. These data indicate that the proportion of MCAM⁺ lymphocytes in biological samples such as peripheral blood or CSF may be used to diagnose the presence of neuroinflammation, such as in MS.

EXAMPLE 6

Expression of MCAM on Th17 Cells Derived from Controls and MS Patients

The data presented in FIGS. 17A and B demonstrate that the proportion of MCAM⁺ IL-17⁺ T cells is significantly higher in MS patients as compared to control subjects.

EXAMPLE 7

Expression of MCAM on Samples from EAE Mice

Figures 18A, 18B:
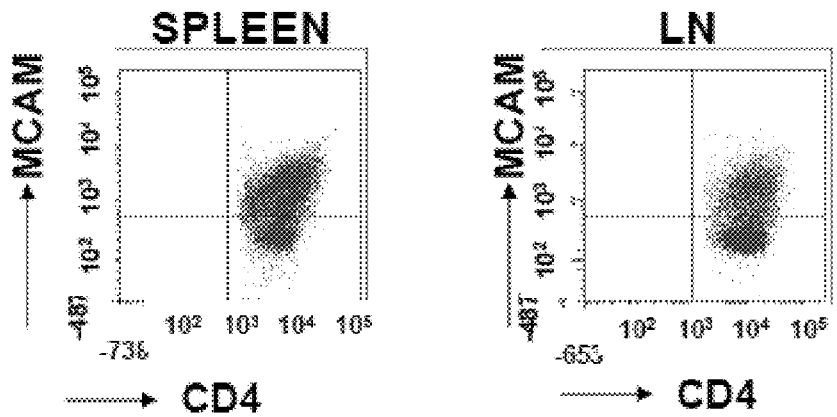
FIGS. 18A-G show the presence of $CD4^+$ and $CD8^+$ $MCAM^+$ T lymphocytes in various organs of mice affected by myelin-oligodendrocyte (MOG) peptide-induced experimental allergic encephalomyelitis (EAE). EAE was induced in C57BL6 mice by injection of $MOG_{35-55}$ in complete Freunds adjuvant. At the peak of the disease (day 14), two animals were sacrificed and the presence of $CD4^+$ and $CD8^+$ $MCAM^+$ lymphocytes was assessed in the spleen, the lymph nodes (LN) and the CNS of the animals.
Figure 18C:
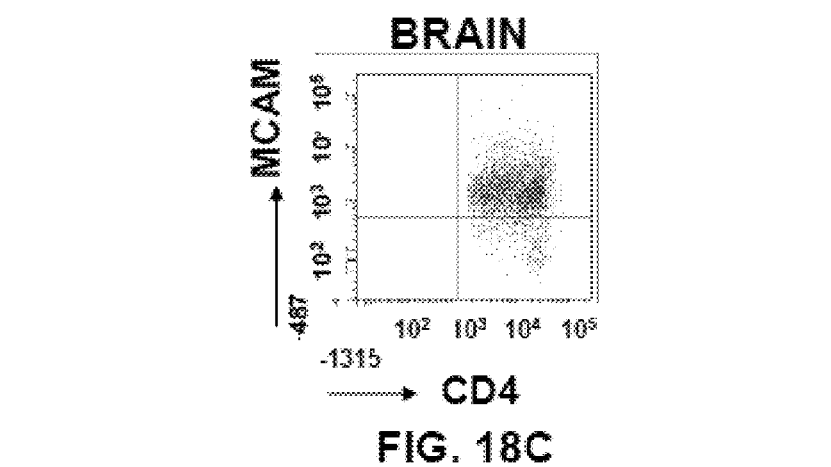
Figures 18D, 18E:
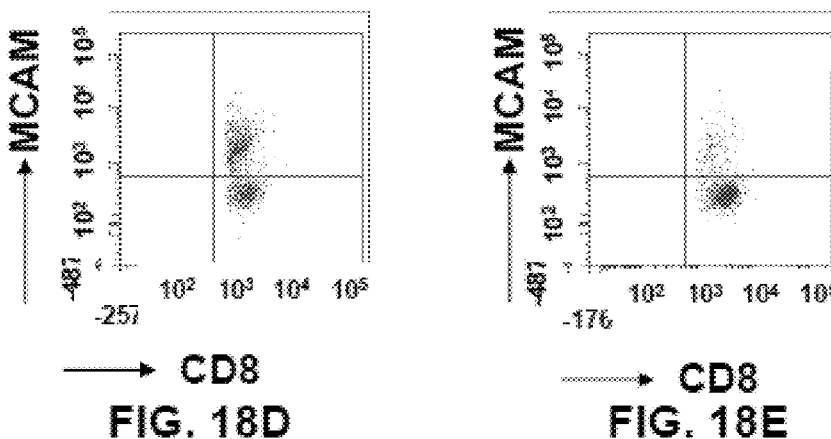
Figure 18F:
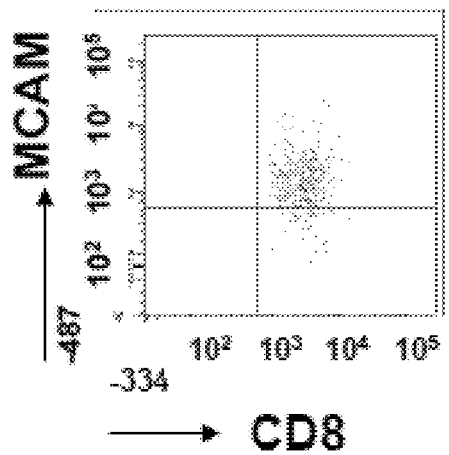
Figure 18G:
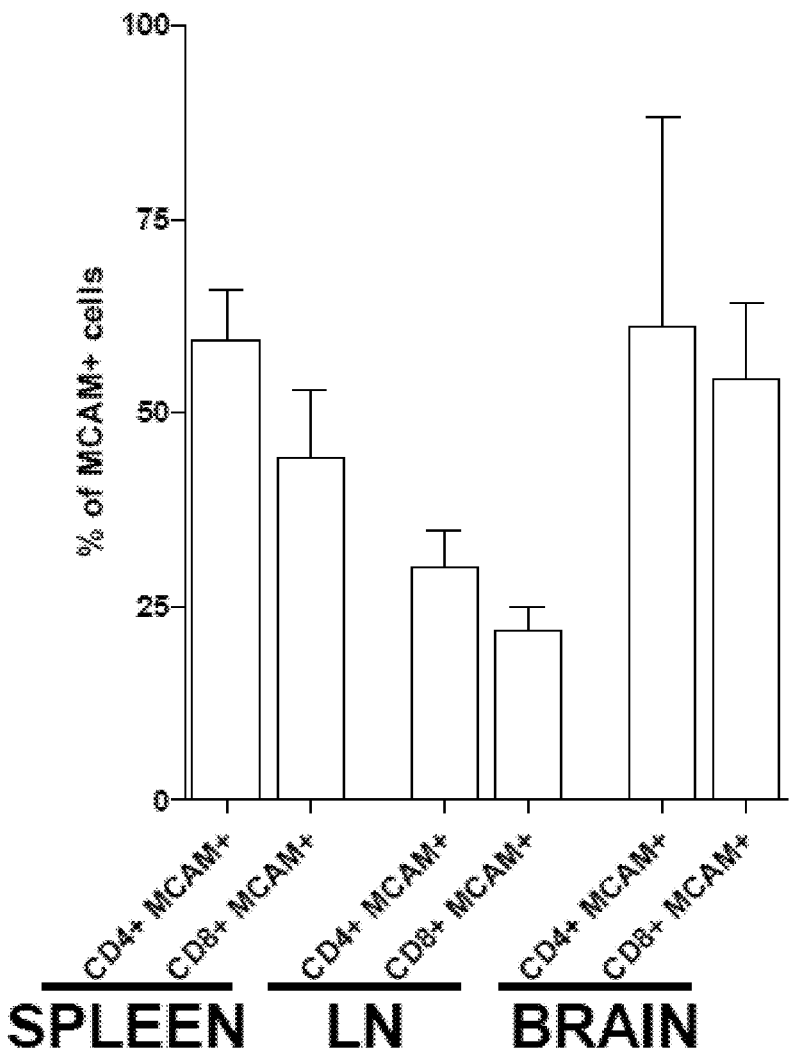

As shown in FIGS. 18A and B, MCAM⁺ T cells are enriched in the CNS and the lymph nodes of EAE mice suffering from neurological symptoms, suggestive of a role for MCAM in the migration of inflammatory IL-17-secreting T cells to the CNS.

EXAMPLE 8

Figure 20A:
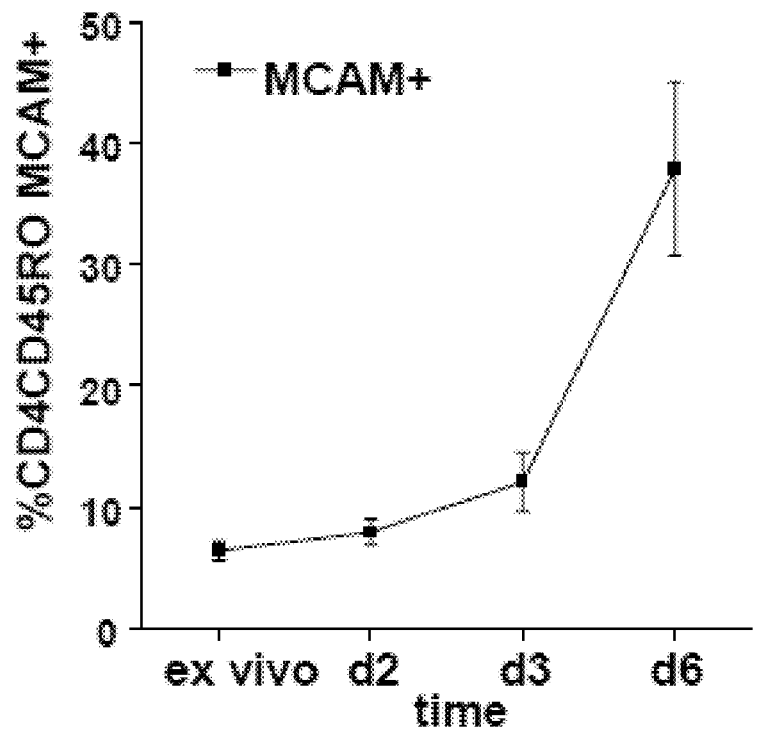
FIGS. 20A-C show the expression of MCAM (FIG. 20A), IL-17 (FIG. 20B) and IFN-γ (FIG. 20C) following ex vivo IL-23 driven polarization of $CD4^+CD45RO^+$ cells. $CD4^+CD45RO^+$ cells were isolated from the peripheral blood of healthy volunteers (n=6). Lymphocytes were cultured for up to 6 days in the presence of autologous $CD14^+$ monocytes, IL-23, anti-IL-4, anti-IFNg, OKT3 (anti-CD3) in ex vivo medium without serum. At indicated time points, T cells were analyzed by flow cytometry intracellular cytokine staining (ICS) following a 4h30 incubation with Phorbol Myristate Acetate/Ionomycin (PMA/iono) in the presence of Brefeldin A (BFA), ns=not significant.
Figure 20B:
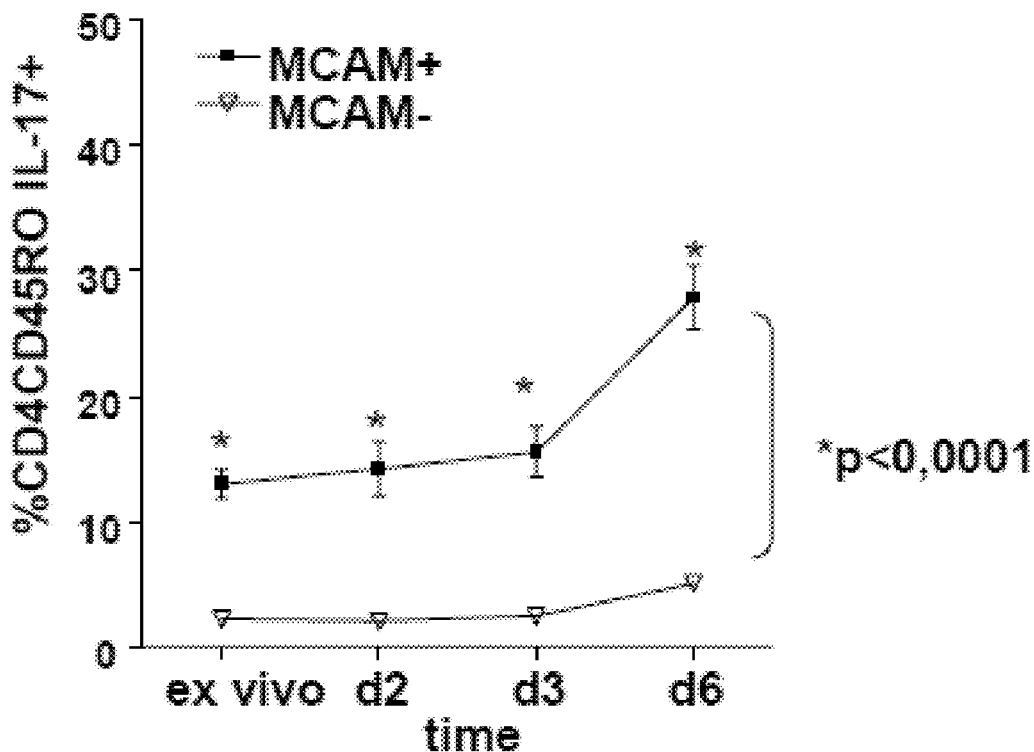
Figure 20C:
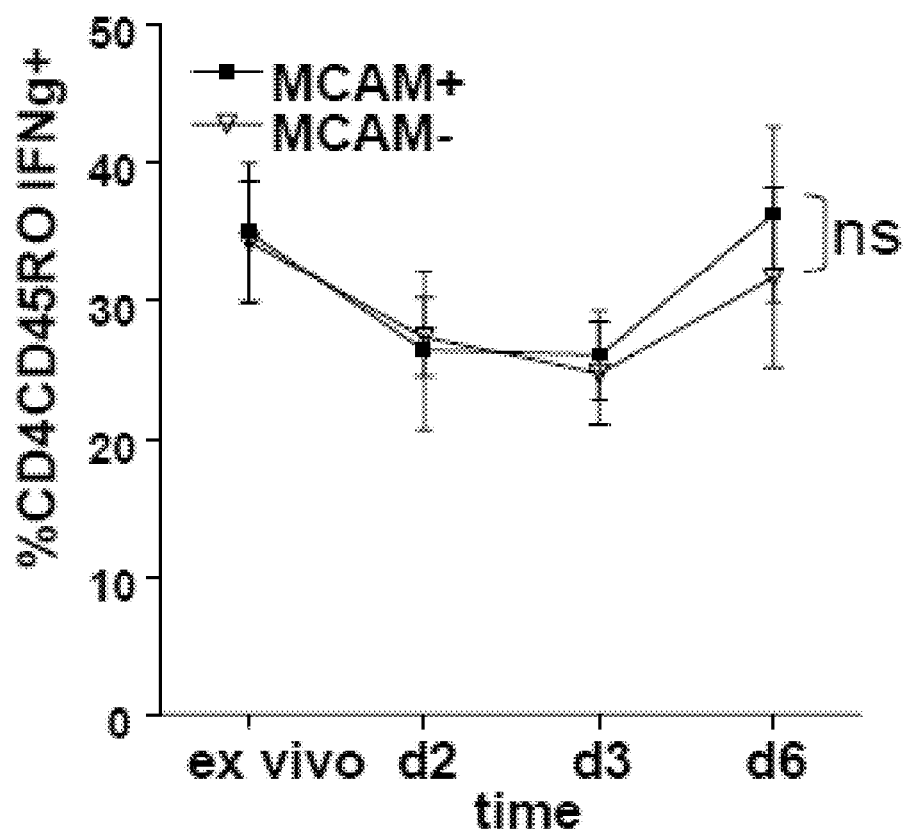
Figure 21A:
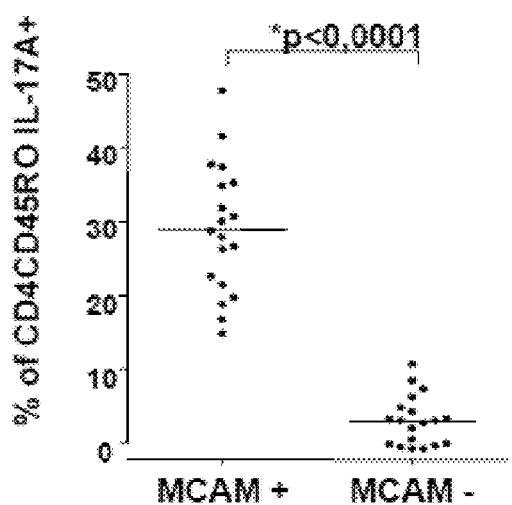
FIGS. 21A-F show the expression of IL-17 (FIG. 21A), Granzyme B (FIG. 21B), IL-22 (FIG. 21C), IFN-γ (FIG. 21D), GM-CSF (FIG. 21E) and IL-2 (FIG. 21F) by $MCAM^+$ and $MCAM^- CD4^+CD45RO^+$ cells following ex vivo IL-23 driven polarization. $CD4^+CD45RO^+$ cells were isolated from the peripheral blood of healthy volunteers (n=6). Lymphocytes were cultured for up to 6 days in the presence of autologous $CD14^+$ monocytes, IL-23, anti-IL-4, anti-IFN-γ, OKT3 (anti-CD3) in ex vivo medium without serum. At indicated time points, T cells were analyzed by flow cytometry intracellular cytokine staining (ICS) following a 4h30 incubation with Phorbol Myristate Acetate/Ionomycin (PMA/iono) in the presence of Brefeldin A (BFA), ns=not significant.
Figure 21B:
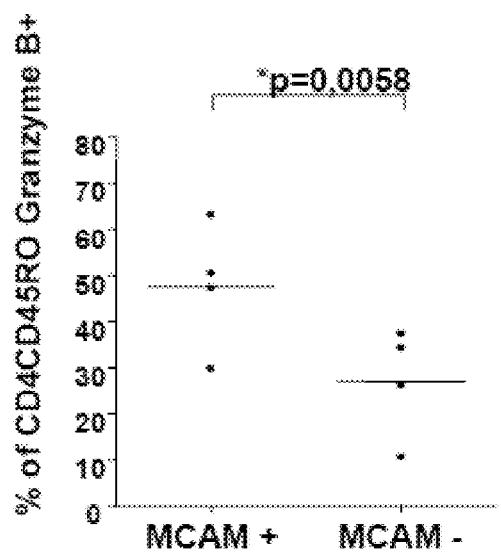
Figure 21C:
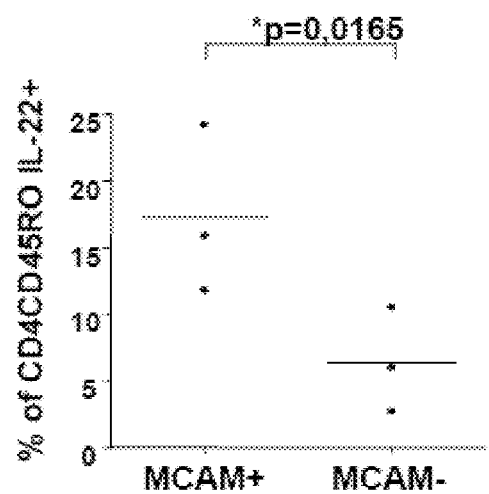
Figure 21D:
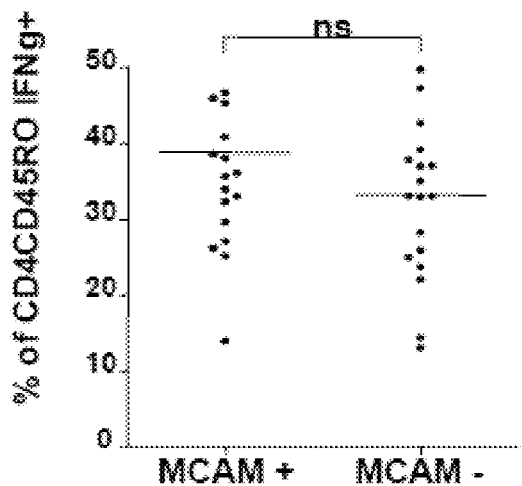
Figure 21E:
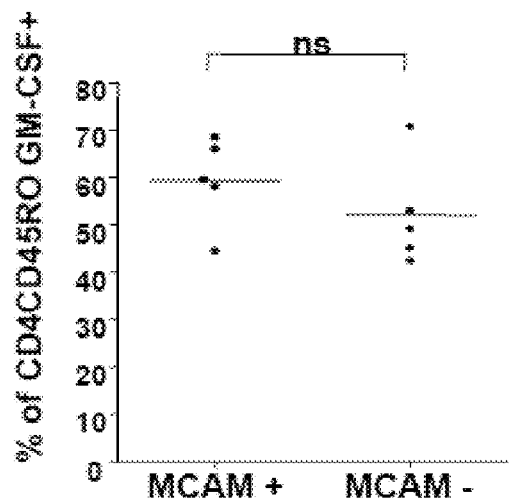
Figure 21F:
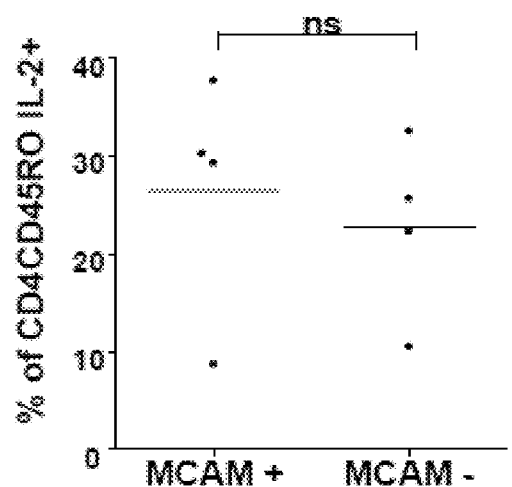
Figure 22A:
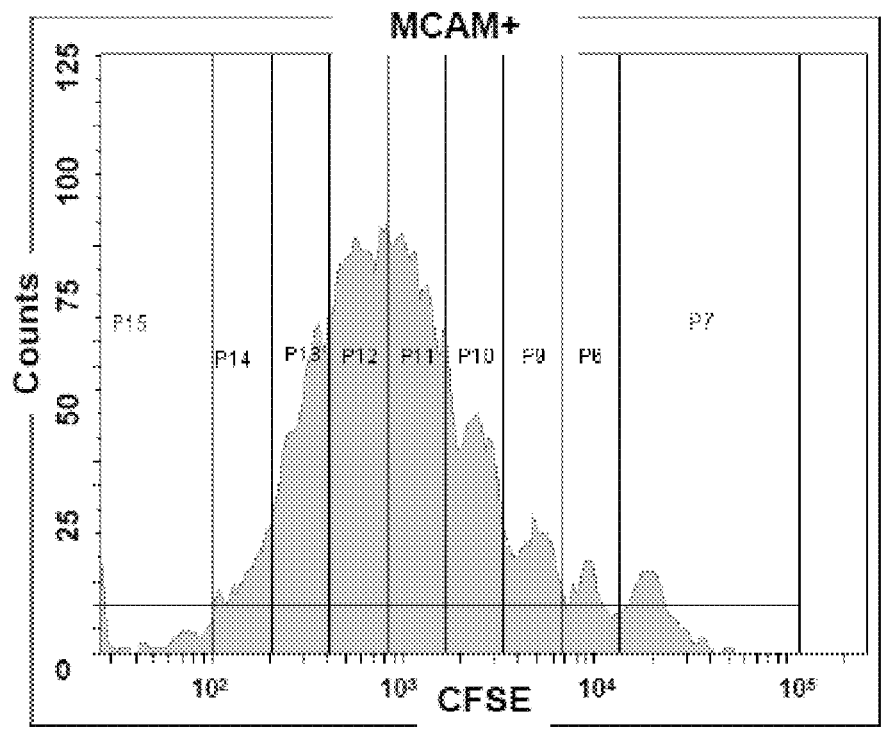
FIGS. 22A-C show the proliferation of $MCAM^+$ and $MCAM^- CD4^+CD45RO^+$ cells following ex vivo IL-23 driven polarization. $CD4^+CD45RO^+$ cells were isolated from the peripheral blood of healthy volunteers (n=6). Lymphocytes were cultured for up to 6 days in the presence of autologous $CD14^+$ monocytes, IL-23, anti-IL-4, anti-IFN-γ, OKT3 (anti-CD3) in ex vivo medium without serum. At day 6, CFSE dilution in T cells was analyzed by flow cytometry.
Figure 22B:
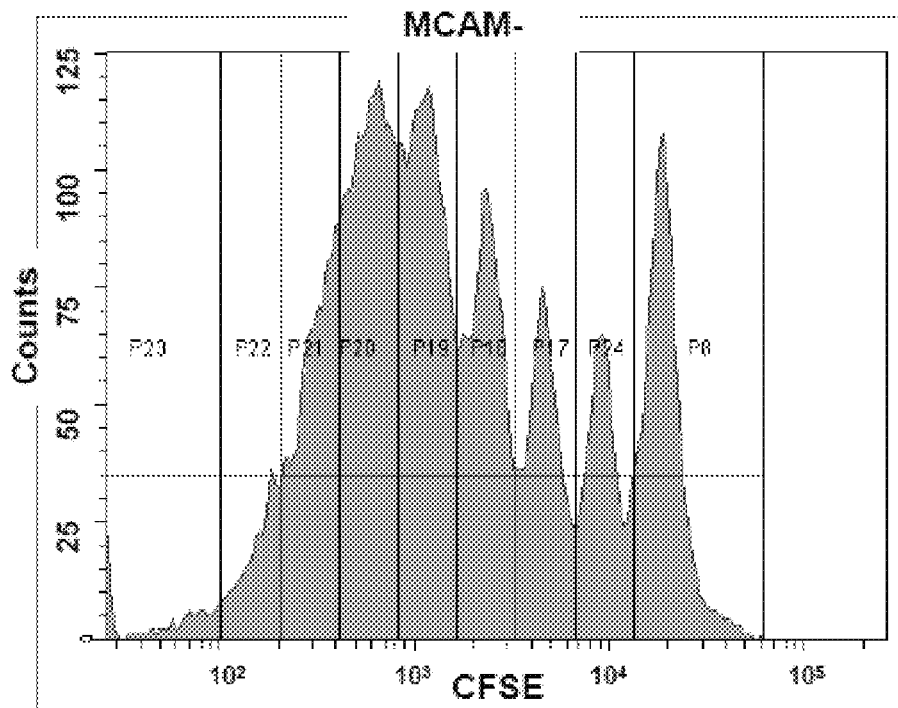
Figure 22C:
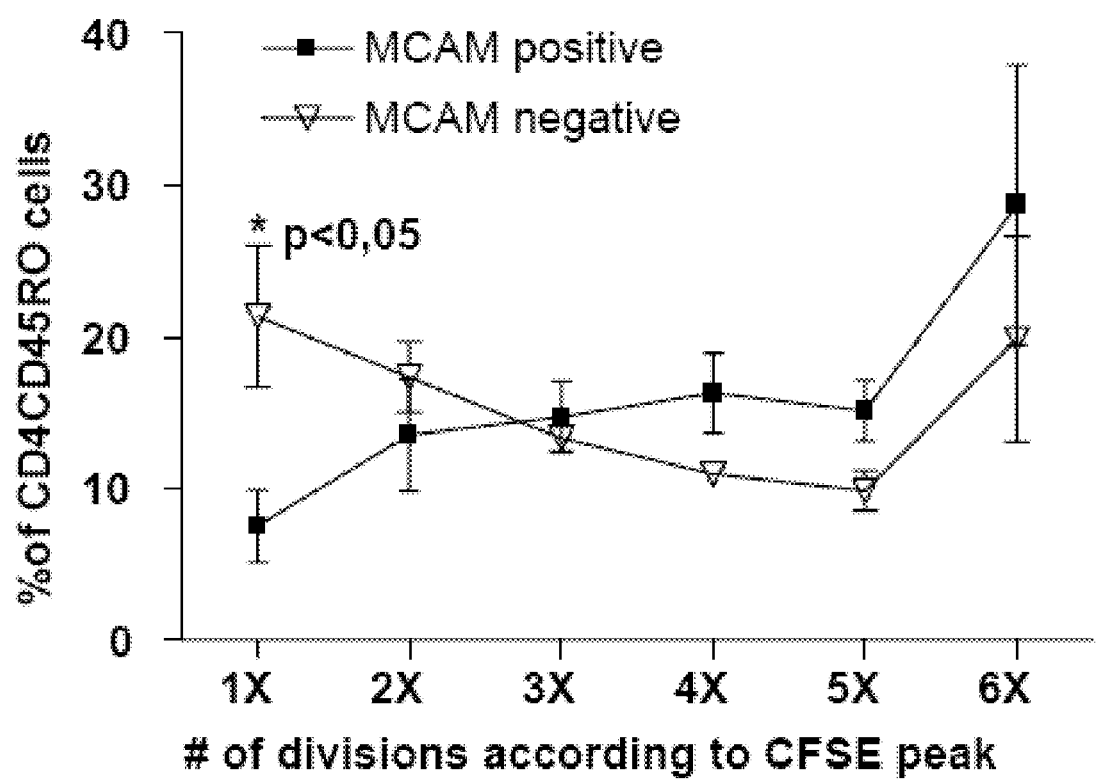
Figure 23:
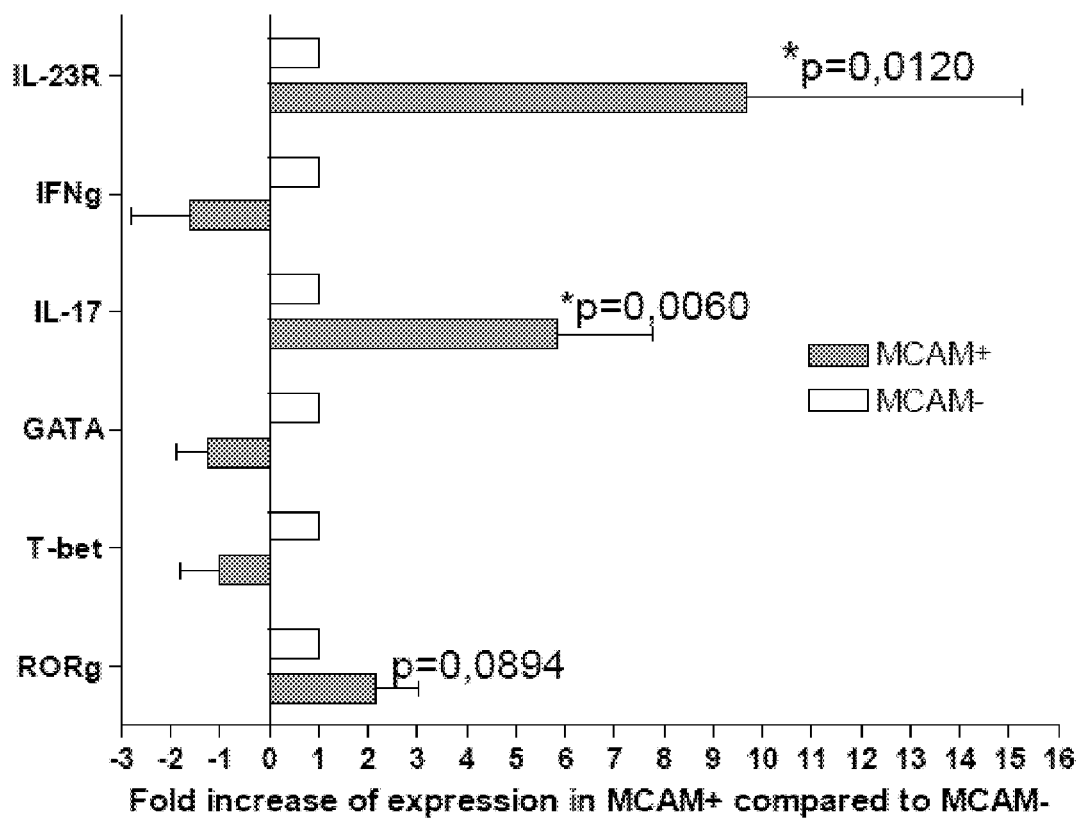
FIG. 23 shows the relative expression of various markers in $MCAM^+$ and $MCAM^- CD4^+CD45RO^+$ cells. $CD4^+CD45RO^+$ were isolated and sorted ex vivo by FACS according to MCAM expression, and then analyzed by qPCR. An arbitrary value of one was accorded to the level of expression of the markers in $MCAM^-$ cells. Relative expression in $MCAM^+$ cells was then expressed as fold increase relative to the level of expression in $MCAM^-$ cells (negative values indicating a lower expression in $MCAM^+$ cells relative to $MCAM^-$ cells). n=8 different healthy donors.

Characterization of MCAM⁺ Memory T Cells following in vitro IL-23 Driven Polarization FIG. 20 shows that Th17 polarization induces MCAM expression on up to 60% of CD4⁺CD45RO⁺ and increase the percentage of IL-17 positive cells preferentially among MCAM positive cells. Other markers associated with inflammation such as Granzyme B and IL-22 were also significantly more expressed in MCAM⁺ T cells relative to MCAM⁻ cells, whereas a non-statistically significant trend toward higher expression in MCAM⁺ T cells was measured for markers such as IFN-γ, GM-CSF and IL-2 (FIG. 21). MCAM⁺ CD4⁺ CD45RO⁺ cells showed higher proliferation following ex vivo IL-23 driven polarization as compared to their MCAM⁻ counterparts (FIG. 22). FIG. 23 shows that ex vivo sorted MCAM⁺ CD4⁺CD45RO⁺ cells have significantly higher levels of mRNA encoding IL-23R, IL-17 and a trend toward higher RORg mRNA (p=0.0894) relative to MCAM⁻ CD4⁺ CD45RO⁺ cells.

EXAMPLE 9

Effect of MCAM Cross-Linking on Th17 Cells

Figure 24A:
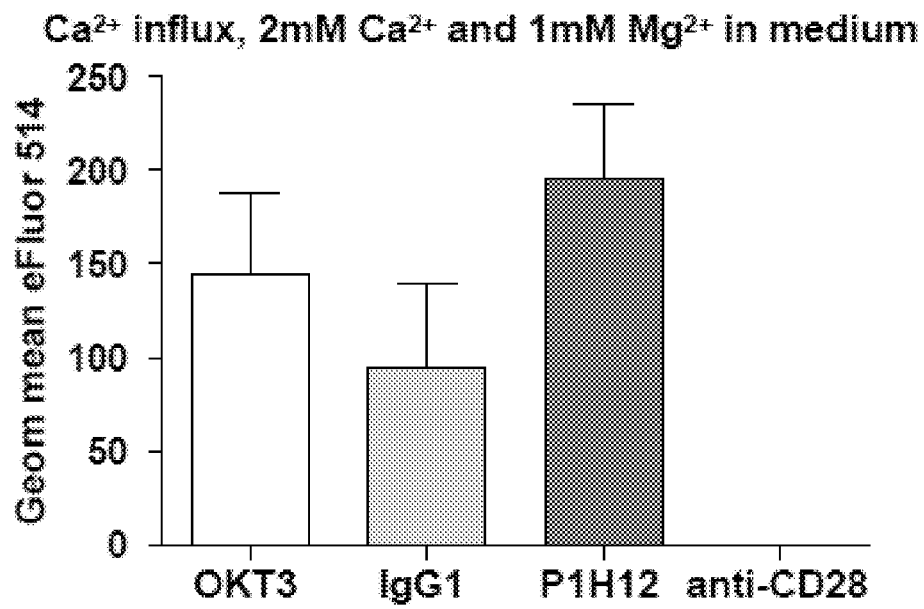
Figure 24B:
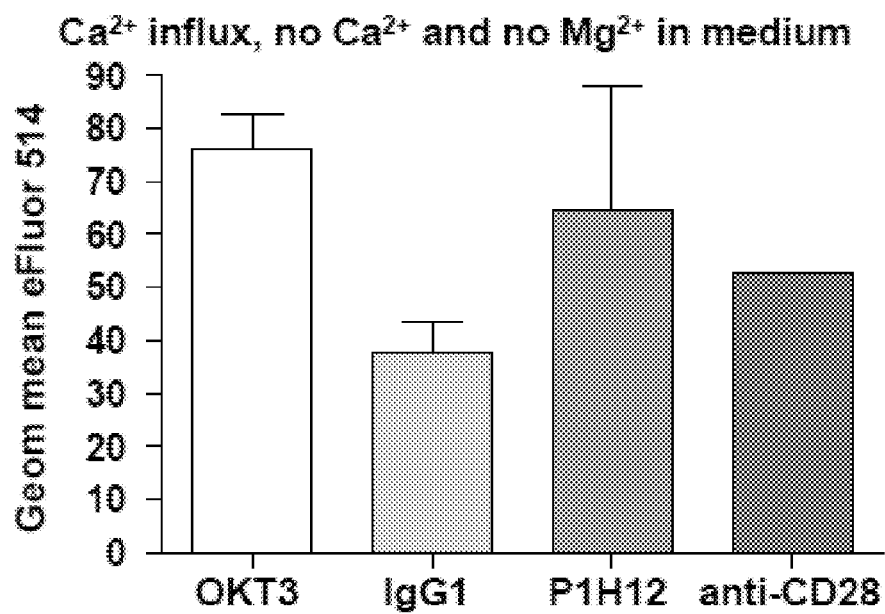
Figure 24F:
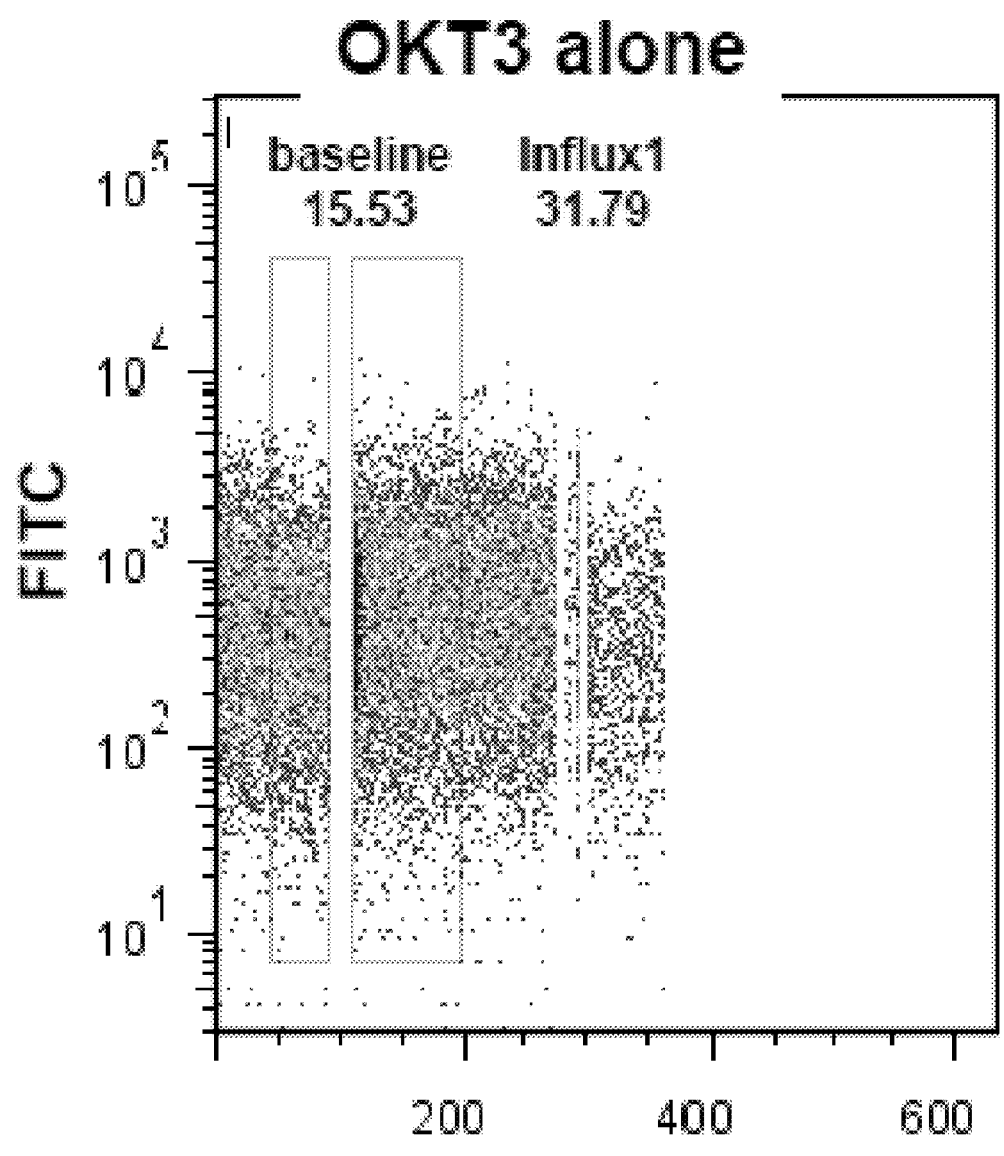
Figure 25:
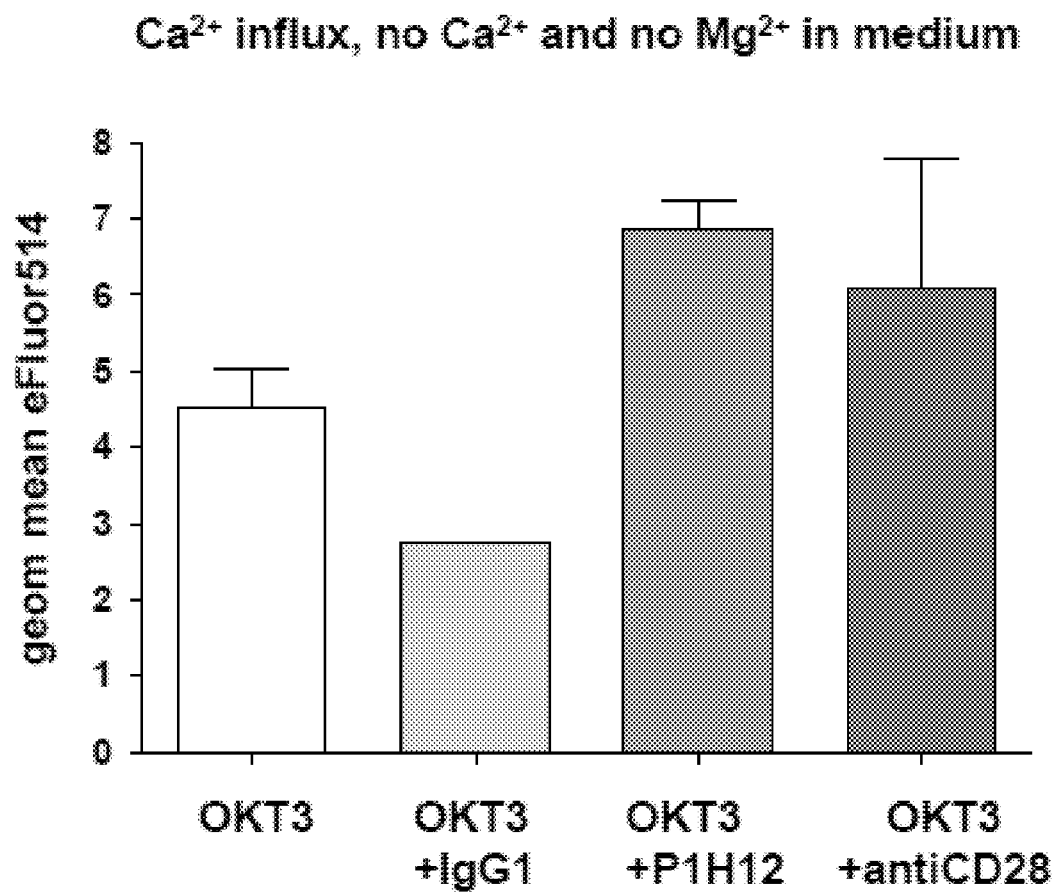
FIG. 25 shows the effect of MCAM cross-linking in the presence of OKT3 (anti-CD3) on $Ca^{2+}$ mobilization in Th17 lymphocytes. Intracellular $Ca^{2+}$ mobilization following MCAM cross-linking on Th17 lymphocytes using $OKT3_+ P1H12$, versus $OKT3_+$ isotype-matched IgG1, $OKT3_+$ anti-CD28 or OKT3 alone. OKT3 was used at 1 μg/ml, whereas the other antibodies were used at 20 μg/ml.
Figure 26A:
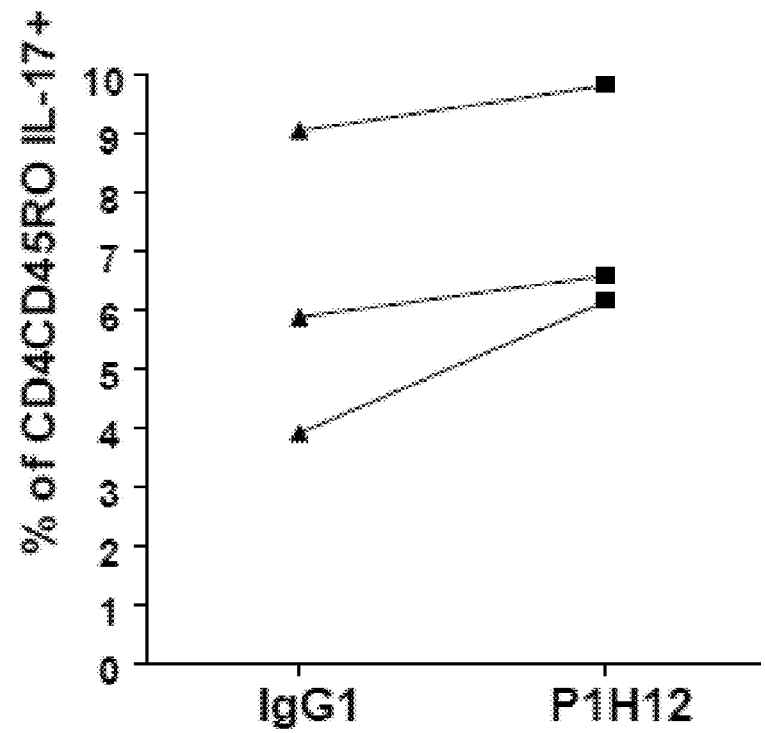
FIGS. 26A-D show the effects of MCAM cross-linking during in vitro suboptimal stimulation. $CD4^+CD45RO^+$ were isolated from the peripheral blood of healthy volunteers (n=3). Lymphocytes were cultured for 6 days in the presence of autologous $CD14^+$ monocytes and OKT3 0.25 μg/ml in ex vivo medium without serum. Antibodies (P1H12 or isotype-matched IgG1) were added daily at a concentration of 10 μg/ml. At day 6, T cells were analyzed by FACS intracellular staining following 4h30 PMA-iono-BFA treatment. IL-17 was assessed in supernatants by ELISA.
Figure 26B:
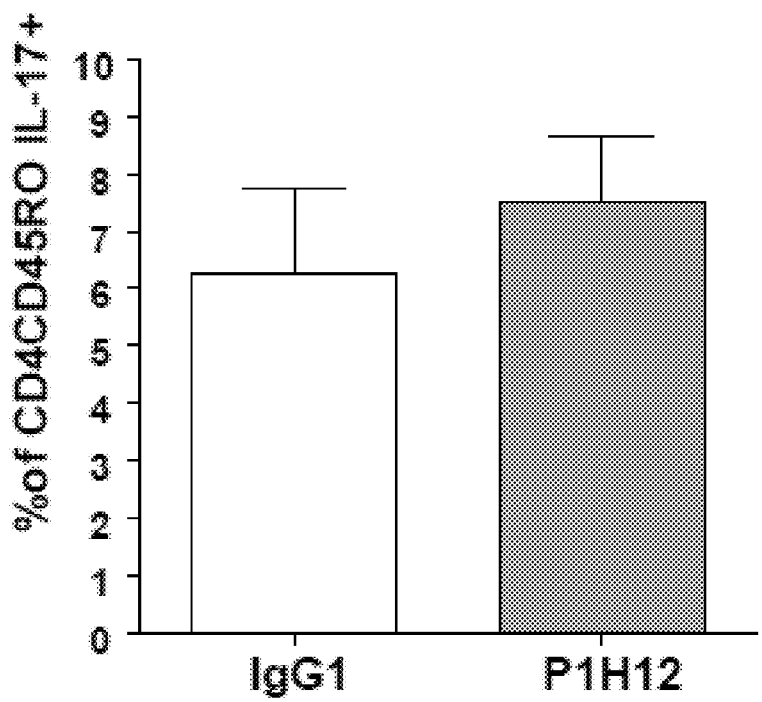
Figure 26C:
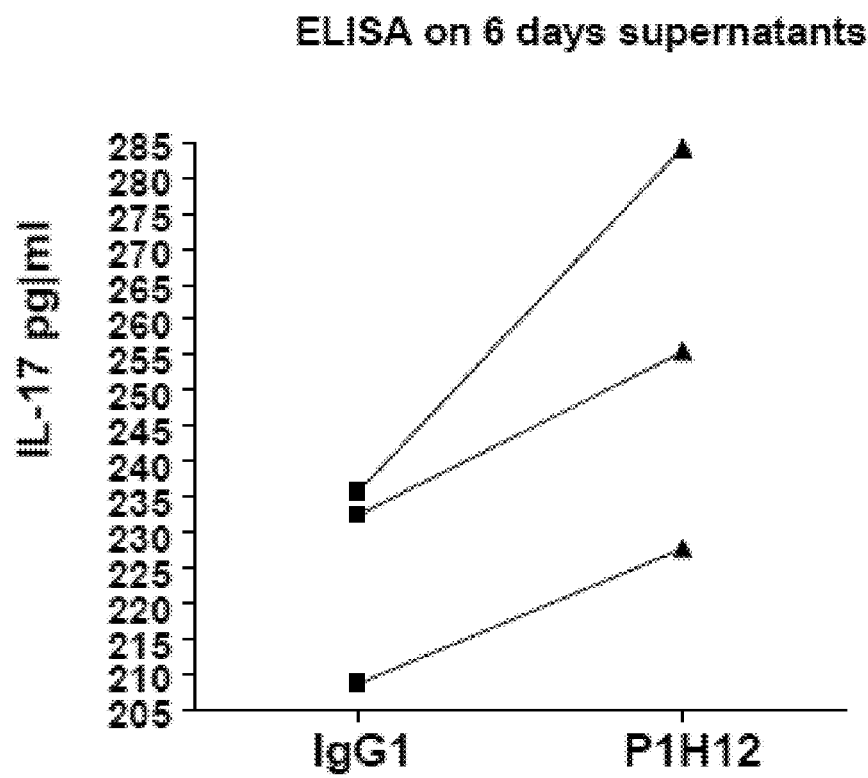
Figure 26D:
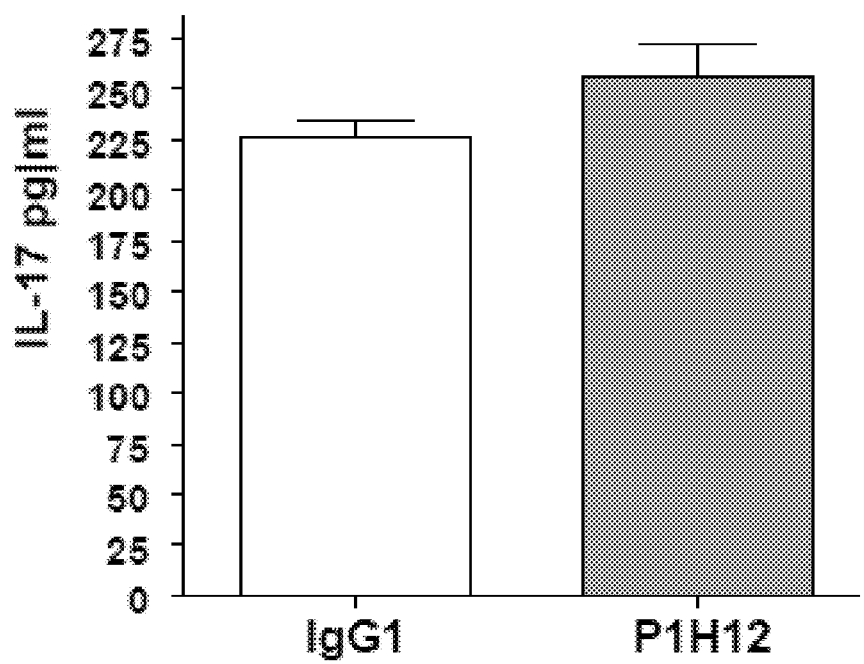

As shown in FIGS. 24A and B, cross-linking of MCAM in the absence of extracellular calcium and magnesium results in a brief calcium influx (bottom panel), whereas a greater intracellular calcium influx is detected in the presence of extracellular calcium and magnesium (top panel). Cross-linking of MCAM on Th17 in the presence of OKT3 (anti-CD3) and in the absence of extracellular calcium and magnesium results in an increased intracellular $Ca^{2+}$ mobilization (relative to OKT3 alone and isotype₊OKT3 control). Also, MCAM cross-linking during in vitro suboptimal stimulation of Th17 cells leads to a slight increase in the number of IL-17-positive cells and in the levels of IL-17 in the supernatants, as compared to cells cultured in the presence of an isotype control (FIG. 26).

EXAMPLE 10

Co-Localization of MCAM and IL-17 in MS Lesions

Figure 27:
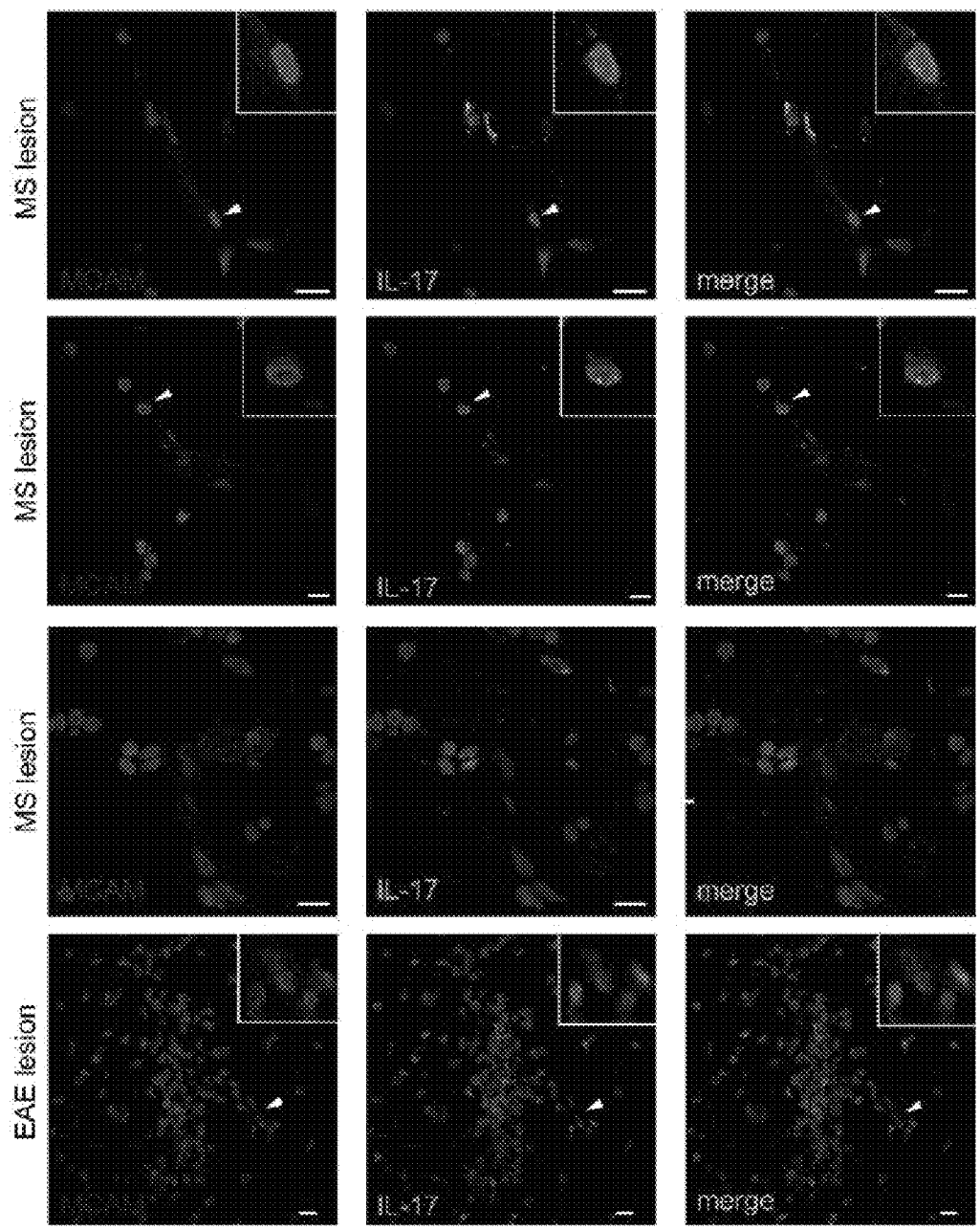
FIG. 27 shows a representative immunohistofluorescence staining on frozen sections from MS brains (n=3 patients, 8 lesions) and from EAE brains (n=2 animals, 10 lesions). Scale bar=10 μm. Insets show MCAM and IL-17 co-localization in mononuclear cells.

FIG. 27 shows that MCAM and IL-17 co-localized in mononuclear cells from MS and EAE lesions.

Although the present invention has been described hereinabove by way of specific embodiments thereof, it can be modified, without departing from the spirit and nature of the subject invention as defined in the appended claims.

---

The invention claimed is:

1. A method of identifying a compound for preventing or treating a neuroinflammatory condition, said method comprising determining whether a level of MCAM polypeptide activity is decreased in the presence of a test compound relative to in the absence of said test compound; wherein said decrease is indicative that said test compound may be used for preventing or treating a neuroinflammatory condition.

2. The method of claim 1, wherein said neuroinflammatory condition is multiple sclerosis (MS).

3. The method of claim 1, wherein said MCAM polypeptide comprises the amino acid sequence of SEQ ID NO:2.

4. The method of claim 3, wherein said MCAM polypeptide is encoded by a nucleic acid comprising the coding sequence of SEQ ID NO:1.

5. The method of claim 1, further comprising determining whether said test compound prevents or treats neuroinflammation in an animal model.

6. The method of claim 5, wherein said animal model is an Experimental Autoimmune Encephalomyelitis (EAE) mouse model.

7. The method of claim 1, wherein said MCAM activity is MCAM-mediated cell adhesion.

8. The method of claim 7, wherein said MCAM-mediated cell adhesion is adhesion of an MCAM-expressing immune cell to an endothelial cell of the blood-brain barrier.

9. The method of claim 8, wherein said MCAM-expressing immune cell is an MCAM-expressing T lymphocyte.

* * * * *

UNITED STATES PATENT AND TRADEMARK OFFICE
CERTIFICATE OF CORRECTION

| | | |
|---|---|---|
| PATENT NO. | : 8,293,468 B2 | Page 1 of 1 |
| APPLICATION NO. | : 12/797055 | |
| DATED | : October 23, 2012 | |
| INVENTOR(S) | : Alexandre Prat, Romain Cayrol and Nathalie Arbour | |

It is certified that error appears in the above-identified patent and that said Letters Patent is hereby corrected as shown below:

On the Title pg, item (75) Inventors: Remove "Catherine Larochelle, Montreal (CA)"

Signed and Sealed this

Twenty-second Day of January, 2013

David J. Kappos
*Director of the United States Patent and Trademark Office*